US009381420B2

(12) United States Patent
Burroughs

(10) Patent No.: US 9,381,420 B2
(45) Date of Patent: Jul. 5, 2016

(54) WORKOUT USER EXPERIENCE

(71) Applicant: NIKE, Inc., Beaverton, OR (US)

(72) Inventor: Brandon S Burroughs, Portland, OR (US)

(73) Assignee: NIKE, INC., Beverton, OR (US)

( * ) Notice: Subject to any disclaimer, the term of this patent is extended or adjusted under 35 U.S.C. 154(b) by 0 days.

(21) Appl. No.: 13/771,261

(22) Filed: Feb. 20, 2013

(65) Prior Publication Data

US 2014/0135955 A1 May 15, 2014

Related U.S. Application Data

(63) Continuation-in-part of application No. 13/399,452, filed on Feb. 17, 2012.

(60) Provisional application No. 61/601,601, filed on Feb. 22, 2012, provisional application No. 61/601,618, filed on Feb. 22, 2012, provisional application No. 61/601,604, filed on Feb. 22, 2012, provisional application No. 61/443,808, filed on Feb. 17, 2011.

(51) Int. Cl.
*A63F 13/06* (2006.01)
*A63B 71/06* (2006.01)
*G06F 19/00* (2011.01)
*G09B 19/00* (2006.01)

(52) U.S. Cl.
CPC ........ *A63B 71/0622* (2013.01); *G06F 19/3481* (2013.01); *G09B 19/0038* (2013.01)

(58) Field of Classification Search
CPC ....................................... A63F 13/06
USPC ........................................... 463/2, 30, 31, 42
See application file for complete search history.

(56) References Cited

U.S. PATENT DOCUMENTS

| 3,270,564 | A | 9/1966 | Evans |
| 4,372,558 | A | 2/1983 | Shimamoto et al. |
| 4,373,651 | A | 2/1983 | Fanslow |
| 4,518,267 | A | 5/1985 | Hepp |
| 4,578,969 | A | 4/1986 | Larson |
| 4,647,918 | A | 3/1987 | Goforth |
| 4,703,445 | A | 10/1987 | Dassler |
| 4,745,930 | A | 5/1988 | Confer |

(Continued)

FOREIGN PATENT DOCUMENTS

| CA | 2668946 A1 | 5/2008 |
| CN | 200994779 Y | 12/2007 |

(Continued)

OTHER PUBLICATIONS

International Search Report from International Application No. PCT/US2012/025664 mailed Jun. 6, 2012, 4 pages.

(Continued)

*Primary Examiner* — Omkar Deodhar
(74) *Attorney, Agent, or Firm* — Banner & Witcoff, Ltd.

(57) ABSTRACT

Systems and methods for receiving input data at a touch sensitive display are provided. Athletic training data is displayed to a user. The user performs activities, such as attempting basketball shots. The user then uses a number of fingers to tap or swipe the touch sensitive display to input parameters. A tap with one finger may indicate a made one point shot and a swipe with two fingers may indicate a missed two point shot.

17 Claims, 42 Drawing Sheets

(56) References Cited

U.S. PATENT DOCUMENTS

| | | | |
|---|---|---|---|
| 4,814,661 A | 3/1989 | Ratzlaff et al. | |
| 5,033,291 A | 7/1991 | Podoloff et al. | |
| 5,047,952 A | 9/1991 | Kramer et al. | |
| 5,050,962 A | 9/1991 | Monnier et al. | |
| 5,150,536 A | 9/1992 | Strong | |
| 5,249,967 A * | 10/1993 | O'Leary et al. | 434/247 |
| 5,303,131 A | 4/1994 | Wu | |
| 5,323,650 A | 6/1994 | Fullen et al. | |
| 5,373,651 A | 12/1994 | Wood | |
| 5,374,821 A | 12/1994 | Muhs et al. | |
| 5,393,651 A | 2/1995 | Hoshi | |
| 5,408,873 A | 4/1995 | Schmidt et al. | |
| 5,419,562 A | 5/1995 | Cromarty | |
| 5,422,521 A | 6/1995 | Neer et al. | |
| 5,444,462 A | 8/1995 | Wambach | |
| 5,471,405 A | 11/1995 | Marsh | |
| 5,500,635 A | 3/1996 | Mott | |
| 5,636,146 A | 6/1997 | Flentov et al. | |
| 5,636,378 A | 6/1997 | Griffith | |
| 5,638,300 A | 6/1997 | Johnson | |
| 5,644,858 A | 7/1997 | Bemis | |
| 5,697,791 A | 12/1997 | Nashner et al. | |
| 5,702,323 A | 12/1997 | Poulton | |
| 5,720,200 A | 2/1998 | Anderson et al. | |
| 5,724,265 A | 3/1998 | Hutchings | |
| 5,764,786 A | 6/1998 | Kuwashima et al. | |
| 5,785,666 A | 7/1998 | Costello et al. | |
| 5,812,142 A | 9/1998 | Small et al. | |
| 5,813,142 A | 9/1998 | Demon | |
| 5,813,406 A | 9/1998 | Kramer et al. | |
| 5,844,861 A | 12/1998 | Maurer | |
| 5,903,454 A | 5/1999 | Hoffberg et al. | |
| 5,907,819 A | 5/1999 | Johnson | |
| 5,913,727 A | 6/1999 | Ahdoot | |
| 5,929,332 A | 7/1999 | Brown | |
| 5,960,380 A | 9/1999 | Flentov et al. | |
| 5,963,891 A | 10/1999 | Walker et al. | |
| 6,017,128 A | 1/2000 | Goldston et al. | |
| 6,018,705 A | 1/2000 | Gaudet et al. | |
| 6,050,962 A | 4/2000 | Kramer et al. | |
| 6,066,075 A | 5/2000 | Poulton | |
| 6,081,750 A | 6/2000 | Hoffberg et al. | |
| 6,122,340 A | 9/2000 | Darley et al. | |
| 6,148,280 A | 11/2000 | Kramer | |
| 6,174,294 B1 | 1/2001 | Crabb et al. | |
| 6,195,921 B1 | 3/2001 | Truong | |
| 6,198,394 B1 | 3/2001 | Jacobsen et al. | |
| 6,266,623 B1 | 7/2001 | Vock et al. | |
| 6,287,200 B1 | 9/2001 | Sharma | |
| 6,298,314 B1 | 10/2001 | Blackadar et al. | |
| 6,330,757 B1 | 12/2001 | Russell | |
| 6,336,365 B1 | 1/2002 | Blackadar et al. | |
| 6,356,856 B1 | 3/2002 | Damen et al. | |
| 6,357,147 B1 | 3/2002 | Darley et al. | |
| 6,360,597 B1 | 3/2002 | Hubbard, Jr. | |
| 6,426,490 B1 | 7/2002 | Storz | |
| 6,428,490 B1 | 8/2002 | Kramer et al. | |
| 6,430,843 B1 | 8/2002 | Potter et al. | |
| 6,496,787 B1 | 12/2002 | Flentov et al. | |
| 6,496,952 B1 | 12/2002 | Osada et al. | |
| 6,498,994 B2 | 12/2002 | Vock et al. | |
| 6,515,284 B1 | 2/2003 | Walle et al. | |
| 6,516,284 B2 | 2/2003 | Flentov et al. | |
| 6,536,139 B2 | 3/2003 | Darley et al. | |
| 6,539,336 B1 | 3/2003 | Vock et al. | |
| 6,544,858 B1 | 4/2003 | Beekman et al. | |
| 6,560,903 B1 | 5/2003 | Darley | |
| 6,611,789 B1 | 8/2003 | Darley | |
| 6,640,144 B1 | 10/2003 | Huang et al. | |
| 6,656,042 B2 | 12/2003 | Reiss et al. | |
| 6,718,200 B2 | 4/2004 | Marmaropoulos et al. | |
| 6,748,462 B2 | 6/2004 | Dubil et al. | |
| 6,778,973 B2 | 8/2004 | Harlan | |
| 6,785,579 B2 | 8/2004 | Huang et al. | |
| 6,785,805 B1 | 8/2004 | House et al. | |
| 6,808,462 B2 | 10/2004 | Snyder et al. | |
| 6,829,512 B2 | 12/2004 | Huang et al. | |
| 6,836,744 B1 | 12/2004 | Asphahani et al. | |
| 6,876,947 B1 | 4/2005 | Darley et al. | |
| 6,882,897 B1 | 4/2005 | Fernandez | |
| 6,885,971 B2 | 4/2005 | Vock et al. | |
| 6,889,282 B2 | 5/2005 | Schollenberger | |
| 6,892,216 B2 | 5/2005 | Coburn, II et al. | |
| 6,909,420 B1 | 6/2005 | Nicolas et al. | |
| 6,922,664 B1 | 7/2005 | Fernandez et al. | |
| 6,932,698 B2 | 8/2005 | Sprogis | |
| 6,959,259 B2 | 10/2005 | Vock et al. | |
| 6,963,818 B2 | 11/2005 | Flentov et al. | |
| 6,978,320 B2 | 12/2005 | Nonaka | |
| 7,030,861 B1 * | 4/2006 | Westerman et al. | 345/173 |
| 7,045,151 B2 | 5/2006 | Trant | |
| 7,046,151 B2 | 5/2006 | Dundon | |
| 7,054,784 B2 | 5/2006 | Flentov et al. | |
| 7,057,551 B1 | 6/2006 | Vogt | |
| 7,070,571 B2 | 7/2006 | Kramer et al. | |
| 7,072,789 B2 | 7/2006 | Vock et al. | |
| 7,092,846 B2 | 8/2006 | Vock et al. | |
| 7,152,343 B2 | 12/2006 | Whatley | |
| 7,162,392 B2 | 1/2007 | Vock et al. | |
| 7,171,331 B2 | 1/2007 | Vock et al. | |
| 7,200,517 B2 | 4/2007 | Darley et al. | |
| 7,245,898 B2 | 7/2007 | Van Bosch et al. | |
| 7,283,647 B2 | 10/2007 | McNitt | |
| 7,304,580 B2 | 12/2007 | Sullivan et al. | |
| 7,310,895 B2 | 12/2007 | Whittlesey et al. | |
| 7,383,728 B2 | 6/2008 | Noble et al. | |
| RE40,474 E | 9/2008 | Quellais et al. | |
| 7,426,873 B1 | 9/2008 | Kholwadwala et al. | |
| 7,428,471 B2 | 9/2008 | Darley et al. | |
| 7,433,805 B2 | 10/2008 | Vock et al. | |
| 7,457,724 B2 | 11/2008 | Vock et al. | |
| 7,498,856 B2 | 3/2009 | Lin et al. | |
| 7,498,956 B2 | 3/2009 | Baier et al. | |
| 7,513,852 B2 | 4/2009 | Wilkins et al. | |
| 7,522,970 B2 | 4/2009 | Fernandez | |
| 7,552,549 B2 | 6/2009 | Whittlesey et al. | |
| 7,579,946 B2 | 8/2009 | Case, Jr. | |
| 7,602,301 B1 | 10/2009 | Stirling et al. | |
| 7,607,243 B2 | 10/2009 | Berner, Jr. et al. | |
| 7,617,068 B2 | 11/2009 | Tadin et al. | |
| 7,620,466 B2 | 11/2009 | Neale et al. | |
| 7,623,987 B2 | 11/2009 | Vock et al. | |
| 7,625,314 B2 | 12/2009 | Ungari et al. | |
| 7,651,442 B2 | 1/2010 | Carlson | |
| 7,658,694 B2 | 2/2010 | Ungari | |
| 7,670,263 B2 | 3/2010 | Ellis et al. | |
| 7,739,076 B1 | 6/2010 | Vock et al. | |
| 7,771,320 B2 | 8/2010 | Riley et al. | |
| 7,805,150 B2 | 9/2010 | Graham et al. | |
| 7,816,632 B2 | 10/2010 | Bourke, III et al. | |
| 7,840,378 B2 | 11/2010 | Vock et al. | |
| 7,901,325 B2 | 3/2011 | Henderson | |
| 7,905,815 B2 | 3/2011 | Ellis et al. | |
| 7,909,737 B2 | 3/2011 | Ellis et al. | |
| 7,921,716 B2 | 4/2011 | Morris Bamberg et al. | |
| 7,927,253 B2 | 4/2011 | Vincent et al. | |
| 7,934,983 B1 | 5/2011 | Eisner | |
| 7,997,007 B2 | 8/2011 | Sanabria-Hernandez | |
| 8,056,268 B2 | 11/2011 | DiBenedetto et al. | |
| 8,061,061 B1 | 11/2011 | Rivas | |
| 8,099,258 B2 | 1/2012 | Alten et al. | |
| 8,142,267 B2 | 3/2012 | Adams | |
| 8,172,722 B2 | 5/2012 | Molyneux et al. | |
| 8,221,290 B2 | 7/2012 | Vincent et al. | |
| 8,251,930 B2 | 8/2012 | Ido | |
| 8,253,586 B1 | 8/2012 | Matak | |
| 8,333,643 B2 | 12/2012 | Eisner | |
| 8,467,979 B2 | 6/2013 | Sobolewski | |
| 8,474,153 B2 | 7/2013 | Brie et al. | |
| 8,484,654 B2 | 7/2013 | Graham et al. | |
| 8,676,541 B2 | 3/2014 | Schrock et al. | |
| 8,739,639 B2 | 6/2014 | Owings et al. | |
| 8,860,584 B1 | 10/2014 | Matak | |
| 2001/0054043 A1 | 12/2001 | Harlan | |

(56) References Cited

U.S. PATENT DOCUMENTS

| | | |
|---|---|---|
| 2002/0134153 A1 | 9/2002 | Grenlund |
| 2003/0009308 A1 | 1/2003 | Kirtley |
| 2003/0054327 A1 | 3/2003 | Evensen |
| 2003/0163287 A1 | 8/2003 | Vock et al. |
| 2003/0207718 A1 | 11/2003 | Perlmutter |
| 2004/0215413 A1 | 10/2004 | Weldum et al. |
| 2004/0218317 A1 | 11/2004 | Kawazu et al. |
| 2004/0226192 A1 | 11/2004 | Geer et al. |
| 2005/0032582 A1 | 2/2005 | Mahajan et al. |
| 2005/0046576 A1 | 3/2005 | Julian et al. |
| 2005/0106977 A1 | 5/2005 | Coulston |
| 2005/0183292 A1 | 8/2005 | DiBenedetto et al. |
| 2005/0188566 A1 | 9/2005 | Whittlesey et al. |
| 2005/0221403 A1 | 10/2005 | Gazenko |
| 2005/0282633 A1 | 12/2005 | Nicolas et al. |
| 2006/0017692 A1 | 1/2006 | Wehrenberg et al. |
| 2006/0025229 A1 | 2/2006 | Mahajan et al. |
| 2006/0025282 A1 | 2/2006 | Redmann |
| 2006/0026120 A1 | 2/2006 | Carolan et al. |
| 2006/0143645 A1 | 6/2006 | Vock et al. |
| 2006/0148594 A1 | 7/2006 | Saintoyant et al. |
| 2006/0205569 A1 | 9/2006 | Watterson et al. |
| 2006/0226843 A1 | 10/2006 | Al-Anbuky et al. |
| 2006/0248749 A1 | 11/2006 | Ellis |
| 2006/0262120 A1 | 11/2006 | Rosenberg |
| 2007/0006489 A1 | 1/2007 | Case et al. |
| 2007/0021269 A1 | 1/2007 | Shum |
| 2007/0032748 A1 | 2/2007 | McNeil et al. |
| 2007/0060408 A1 | 3/2007 | Schultz et al. |
| 2007/0063849 A1 | 3/2007 | Rosella et al. |
| 2007/0063850 A1 | 3/2007 | Devaul et al. |
| 2007/0067885 A1 | 3/2007 | Fernandez |
| 2007/0068244 A1 | 3/2007 | Billing et al. |
| 2007/0073178 A1 | 3/2007 | Browning et al. |
| 2007/0078324 A1 | 4/2007 | Wijisiriwardana |
| 2007/0094890 A1 | 5/2007 | Cho et al. |
| 2007/0118328 A1 | 5/2007 | Vock et al. |
| 2007/0143452 A1 | 6/2007 | Suenbuel et al. |
| 2007/0152812 A1 | 7/2007 | Wong et al. |
| 2007/0156335 A1 | 7/2007 | McBride et al. |
| 2007/0173705 A1 | 7/2007 | Teller et al. |
| 2007/0208544 A1 | 9/2007 | Kulach et al. |
| 2007/0232455 A1 | 10/2007 | Hanoun |
| 2007/0250286 A1 | 10/2007 | Duncan et al. |
| 2007/0260421 A1 | 11/2007 | Berner et al. |
| 2007/0283599 A1 | 12/2007 | Talbott |
| 2008/0027679 A1 | 1/2008 | Shklarski |
| 2008/0028783 A1 | 2/2008 | Immel et al. |
| 2008/0039203 A1 | 2/2008 | Ackley et al. |
| 2008/0048616 A1 | 2/2008 | Paul et al. |
| 2008/0056508 A1 | 3/2008 | Pierce et al. |
| 2008/0060224 A1 | 3/2008 | Whittlesey et al. |
| 2008/0066343 A1 | 3/2008 | Sanabria-Hernandez |
| 2008/0165140 A1* | 7/2008 | Christie et al. ............... 345/173 |
| 2008/0172498 A1 | 7/2008 | Boucard |
| 2008/0177507 A1 | 7/2008 | Mian et al. |
| 2008/0188353 A1 | 8/2008 | Vitolo et al. |
| 2008/0200312 A1 | 8/2008 | Tagliabue |
| 2008/0203144 A1 | 8/2008 | Kim |
| 2008/0218310 A1 | 9/2008 | Alten et al. |
| 2008/0221403 A1 | 9/2008 | Fernandez |
| 2008/0246629 A1 | 10/2008 | Tsui et al. |
| 2008/0255794 A1 | 10/2008 | Levine |
| 2008/0258921 A1 | 10/2008 | Woo et al. |
| 2008/0259028 A1 | 10/2008 | Teepell et al. |
| 2008/0269644 A1 | 10/2008 | Ray |
| 2008/0287832 A1 | 11/2008 | Collins et al. |
| 2008/0293023 A1 | 11/2008 | Diehl et al. |
| 2008/0297608 A1 | 12/2008 | Border et al. |
| 2008/0297832 A1 | 12/2008 | Otsuka |
| 2008/0300914 A1 | 12/2008 | Karkanias et al. |
| 2008/0306410 A1 | 12/2008 | Kalpaxis et al. |
| 2008/0318679 A1 | 12/2008 | Tran et al. |
| 2009/0018691 A1 | 1/2009 | Fernandez |
| 2009/0048538 A1 | 2/2009 | Levine et al. |
| 2009/0061837 A1 | 3/2009 | Chaudhri et al. |
| 2009/0075347 A1 | 3/2009 | Cervin et al. |
| 2009/0076341 A1 | 3/2009 | James et al. |
| 2009/0105047 A1 | 4/2009 | Guidi et al. |
| 2009/0107009 A1 | 4/2009 | Bishop et al. |
| 2009/0135001 A1 | 5/2009 | Yuk |
| 2009/0149299 A1 | 6/2009 | Tchao et al. |
| 2009/0150178 A1 | 6/2009 | Sutton et al. |
| 2009/0153369 A1 | 6/2009 | Baier et al. |
| 2009/0153477 A1 | 6/2009 | Saenz |
| 2009/0163287 A1 | 6/2009 | Vald'Via et al. |
| 2009/0167677 A1 | 7/2009 | Kruse et al. |
| 2009/0171614 A1 | 7/2009 | Damen |
| 2009/0233770 A1 | 9/2009 | Vincent et al. |
| 2009/0235739 A1 | 9/2009 | Morris Bamberg et al. |
| 2009/0259566 A1 | 10/2009 | White, III et al. |
| 2009/0262088 A1 | 10/2009 | Moll-Carrillo et al. |
| 2009/0297832 A1 | 12/2009 | Hatta et al. |
| 2010/0000121 A1 | 1/2010 | Brodie et al. |
| 2010/0004566 A1 | 1/2010 | Son et al. |
| 2010/0023531 A1 | 1/2010 | Brisebois et al. |
| 2010/0035688 A1 | 2/2010 | Picunko |
| 2010/0053867 A1 | 3/2010 | Ellis et al. |
| 2010/0056340 A1 | 3/2010 | Ellis et al. |
| 2010/0057951 A1 | 3/2010 | Ellis et al. |
| 2010/0059561 A1 | 3/2010 | Ellis et al. |
| 2010/0062740 A1 | 3/2010 | Ellis et al. |
| 2010/0063778 A1 | 3/2010 | Schrock et al. |
| 2010/0063779 A1 | 3/2010 | Schrock et al. |
| 2010/0072948 A1 | 3/2010 | Sun et al. |
| 2010/0082735 A1 | 4/2010 | Petersen et al. |
| 2010/0094147 A1 | 4/2010 | Inan et al. |
| 2010/0113160 A1 | 5/2010 | Belz et al. |
| 2010/0129780 A1 | 5/2010 | Homsi et al. |
| 2010/0152619 A1 | 6/2010 | Kalpaxis et al. |
| 2010/0184563 A1 | 7/2010 | Molyneux et al. |
| 2010/0184564 A1 | 7/2010 | Molyneux et al. |
| 2010/0191490 A1 | 7/2010 | Martens et al. |
| 2010/0201500 A1 | 8/2010 | Stirling et al. |
| 2010/0201512 A1 | 8/2010 | Stirling et al. |
| 2010/0204616 A1 | 8/2010 | Shears et al. |
| 2010/0225763 A1 | 9/2010 | Vock et al. |
| 2010/0231580 A1 | 9/2010 | Miyasaka |
| 2010/0277617 A1 | 11/2010 | Hollinger |
| 2010/0286601 A1 | 11/2010 | Yodfat et al. |
| 2010/0298659 A1 | 11/2010 | McCombie et al. |
| 2010/0312083 A1 | 12/2010 | Southerland |
| 2010/0332188 A1 | 12/2010 | Vock et al. |
| 2011/0003665 A1 | 1/2011 | Burton et al. |
| 2011/0021280 A1 | 1/2011 | Boroda et al. |
| 2011/0087445 A1 | 4/2011 | Sobolewski |
| 2011/0107369 A1 | 5/2011 | O'Brien et al. |
| 2011/0119027 A1 | 5/2011 | Zhu et al. |
| 2011/0136627 A1 | 6/2011 | Williams |
| 2011/0152695 A1 | 6/2011 | Granqvist et al. |
| 2011/0208444 A1 | 8/2011 | Solinsky |
| 2012/0041767 A1 | 2/2012 | Hoffman et al. |
| 2012/0050529 A1 | 3/2012 | Bentley |
| 2012/0234111 A1 | 9/2012 | Molyneux et al. |
| 2012/0277040 A1 | 11/2012 | Vincent et al. |
| 2013/0079907 A1 | 3/2013 | Homsi et al. |
| 2013/0213145 A1 | 8/2013 | Owings et al. |
| 2014/0033572 A1 | 2/2014 | Steier et al. |
| 2014/0174205 A1 | 6/2014 | Clarke et al. |

FOREIGN PATENT DOCUMENTS

| | | |
|---|---|---|
| CN | 101367011 A | 2/2009 |
| CN | 101367012 A | 2/2009 |
| CN | 101784230 A | 7/2010 |
| CN | 101894206 A | 11/2010 |
| CN | 102143695 A | 8/2011 |
| EP | 0160880 A1 | 11/1985 |
| EP | 0662600 A1 | 7/1995 |
| EP | 1707065 A1 | 10/2006 |
| EP | 2189191 A2 | 5/2010 |
| FR | 2929827 A1 | 10/2009 |
| GB | 251054 A | 4/1926 |
| GB | 2421416 A | 6/2006 |

(56) References Cited

FOREIGN PATENT DOCUMENTS

| | | |
|---|---|---|
| JP | 56-64301 | 5/1981 |
| JP | 05-161724 | 6/1993 |
| JP | 3036281 B2 | 4/2000 |
| JP | 2002163404 A | 6/2002 |
| JP | 2005156531 A | 6/2005 |
| JP | 2005270640 A | 10/2005 |
| JP | 200715117 | 6/2007 |
| JP | 2008-3752 A | 10/2008 |
| JP | 2009148338 A | 7/2009 |
| JP | 2010088886 A | 4/2010 |
| JP | 2010-517725 A | 5/2010 |
| KR | 20050032119 | 4/2005 |
| KR | 20060021632 | 3/2006 |
| KR | 10-2009-0102550 | 9/2009 |
| WO | 0033031 A1 | 6/2000 |
| WO | 02035184 A2 | 5/2002 |
| WO | 2006065679 A2 | 6/2006 |
| WO | 2007064735 A2 | 6/2007 |
| WO | 2007082389 A1 | 7/2007 |
| WO | 2008061023 A2 | 5/2008 |
| WO | 2008134583 A1 | 11/2008 |
| WO | 2009027917 A1 | 3/2009 |
| WO | 2009152456 A2 | 12/2009 |
| WO | 2010065836 A2 | 6/2010 |
| WO | 2010111705 A2 | 9/2010 |
| WO | 20100111705 A2 | 9/2010 |
| WO | 2012061804 A1 | 5/2012 |
| WO | 2012112931 A2 | 8/2012 |
| WO | 2012143274 A2 | 10/2012 |

OTHER PUBLICATIONS

International Bureau, "International Preliminary Report on Patentability," issued in connection with international application serial No. PCT/US2012/025664, mailed Aug. 29, 2013, 6 pages.

International Searching Authority, "International Search Report and Written Opinion," issued in connection with international application serial No. PCT/US2013/048157, mailed Oct. 1, 2013, 10 pages.

International Search Report from International Application No. PCT/US2012/025667 mailed Jul. 31, 2012, 3 pages.

International Search Report from International Application No. PCT/US2012/025701 mailed Jun. 29, 2012, 3 pages.

Morris, "A shoe-integrated sensor system for wireless gait analysis and real-time therapeutic feedback, " Harvard-MIT Division of Health Sciences and Technology, 2004,http://dspace.mitedu/handle/1721.1/28601 (3 pages).

Lovell, "A system for real-time gesture recognition and classification of coordinated motion," Massachusetts Institute of Technology, Dept. of Electrical Engineering and Computer Science, 2005, <http://dspace.mit.edu/handle/1721.1/33290> (2 pages).

Chee et al, "A low cost wearable wireless sensing system for upper limb home rehabilitation," Robotics Automation and Mechatronics (RAM) 2010 IEEE Conference on Jun. 28-30, 2010; Abstract printout (1 page).

Guraliuc et al., "Channel model for on the body communication along and around the human torso at 2.4Ghz and 5.8Ghz," Antenna Technology (IWAT), 2010 International Workshop on Mar. 1-3, 2010; Abstract printout (1 page).

Jun. 21, 2012—(WO) ISR—App No. PCT/US2012/025701.

Frazier, Karen, "How Many Calories to 1 Carb?" published Nov. 12, 2010, Livestrong.com, 3 pages.

Oct. 1, 2013—(WO) ISR and WO—App No. PCT/US2013/048157.

Llosa et al., "Design of a Motion Detector to Monitor Rowing Performance Based on Wireless Sensor Networks," Intelligent Networking and Collaborativge Systems, 2009, http://ieeexplore.ieee.org/xpl/freeabs_all.jsp?arnumber=5369324 (1 page).

Choquette et al., "Accelerometer-based wireless body area network to estimate intensity of therapy in post-acute rehabilitation," Journal of NeuroEngineering and Rehabilitation 2008, http://www.jneuroengrehab.com/content/5/1/20/abstract (1 page).

Morris, "A shoe-integrated sensor system for wireless gait analysis and real-time therapeutic feedback," Harvard-MIT Division of Health Sciences and Technology, 2004,http://dspace.mitedu/handle/1721.1/28601 (3 pages).

Lapinski, "A wearable, wireless sensor system for sports medicine," Massachusetts Institute of Technology, School of Architecture and Planning, Program in Media Arts and Sciences, 2008, http://dspace.mit.edulhandle/1721.1/46581(3 pages).

Aylward, "Sensemble : a wireless inertial sensor system for the interactive dance and collective motion analysis,"Massachusetts Institute of Technology, School of Architecture and Planning, Program in Media Arts and Sciences, 2006, http://dspace.mitedu/handle/1721.1/37391 (3 pages).

Danko; How to Work a Nike Sensor; Dec. 26, 2010; eHow website; 4 pages.

Coyne; Stout's Shoes on Mass Ave Oldest Shoe Store in the USA; Jun. 18, 2013; FunCityFinder website; 5 pages.

Aug. 7, 2013—(WO) ISR and WO—App. No. PCT/US2013/027397.

Aug. 29, 2013—(WO) International Preliminary Report on Patentability App No. PCT/US2012/025713.

Dec. 11, 2009—(WO) ISR and WO App No. PCT/2009/047246.

Aug. 21, 2012—(WO) ISR and WO—App. No. PCT/US2012/025717.

Jul. 11, 2012—(WO) ISR & WO App No. PCT/US2012/025709.

May 28, 2013—(WO) ISR & WO App No. PCT/US2013/027421.

Fleming et al, Athlete and Coach Perceptions of Technology Needs for Evaluating Running Performance, article, Aug. 14, 2010, 18 pages, 13:1-18, UK.

Salpavaara, et al. Wireless Insole Sensor System for Plantar Force Measurements during Sports Events, article, Sep. 6-11, 2009, XIX IMEKO World Congress, Fundamental and Applied Metrology, 6 pages, Lisbon, Portugal.

Mar. 7, 2012—(WO) ISR and WO—App. PCT/US2011/060187.

Jul. 15, 2013—(WO) Search Report and Written Opinion—App. No. PCT/US2013/022219.

Sep. 16, 2010—International Preliminary Report on Patentability for International Application No. PCT/US2009/035877.

Jul. 2, 2009—(WO) International Search Report and Written Opinion—App. No. PCT/US2009/35877.

Jun. 15, 2010—(WO) International Search Report—App. No. PCT/US2009/066745.

May 11, 2010—(WO) International Search Report—App. No. PCT/US2009/066819.

Apr. 25, 2012—(EP) European Search Report—App. No. 11 195 591.0.

* cited by examiner

| | TOTAL PLAY TIME | 48 MINUTES |
|---|---|---|
| | Total Activity Points | 932 POINTS |
| | Activity Points Rate | 48 PTS/MIN |
| | HUSTLE | ■ HIGH |
| | TOP VERTICAL | 26 INCHES |
| | AVERAGE VERTICAL | 8 INCHES |
| | TOTAL VERTICAL | 120 FEET |
| | TOP AIR TIME | 1.2 SECONDS |
| | AVERAGE AIR TIME | 0.4 SECONDS |
| | TOTAL AIR TIME | 42 SECONDS |

| | QUICKNESS | 45 STEPS/SEC |
|---|---|---|
| | DISTANCE | 3.2 MILES |
| | MOST POWER | 89 WATTS |
| | AVERAGE POWER | 33 WATTS |
| | TOTAL POWER | 542 WATTS |
| | BALANCE | 71 % ON TOES |
| | BALANCE | 👣 RIGHT |
| | PLAY STYLE | ■ AGGRESSIVE |
| | ENDURANCE | ■ HIGH |
| | TOTAL CALORIES | 345 CALORIES |

FIG. 9

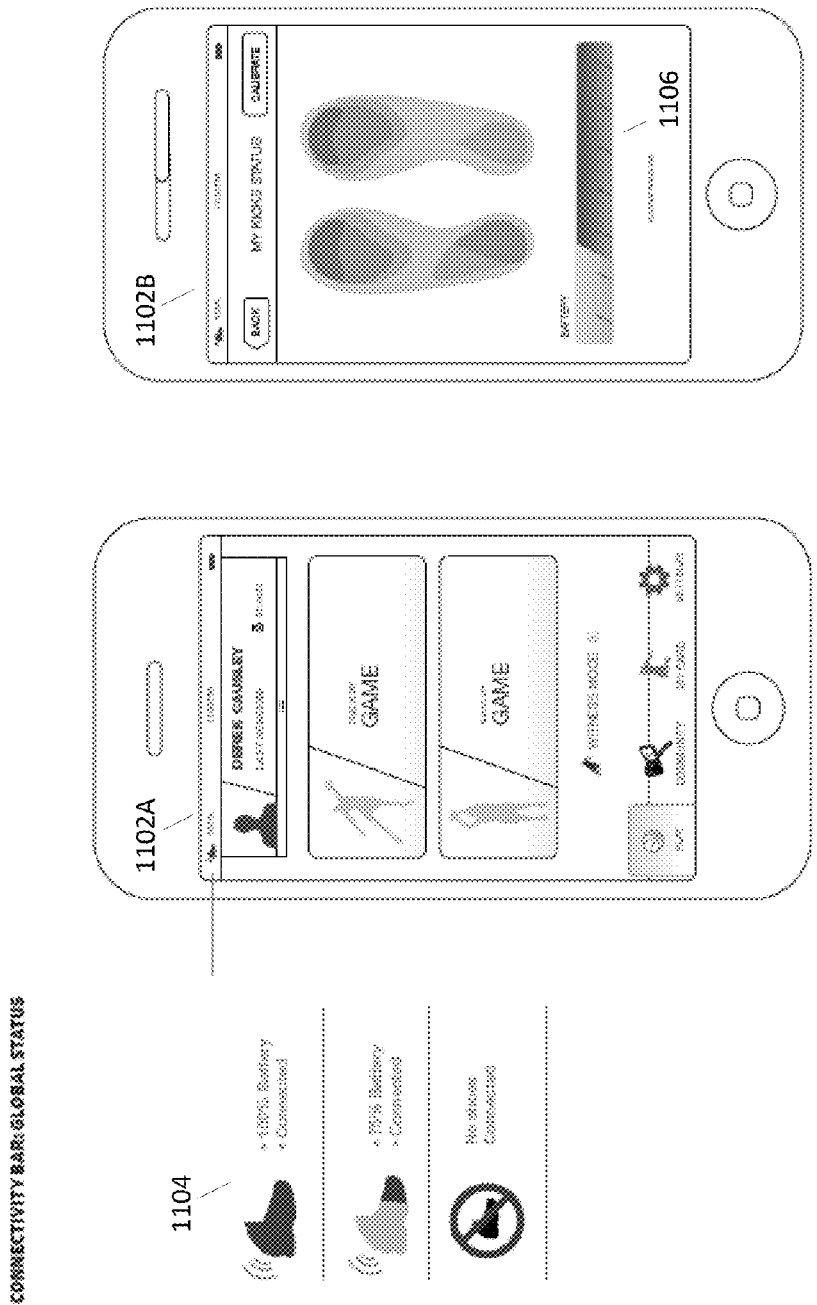

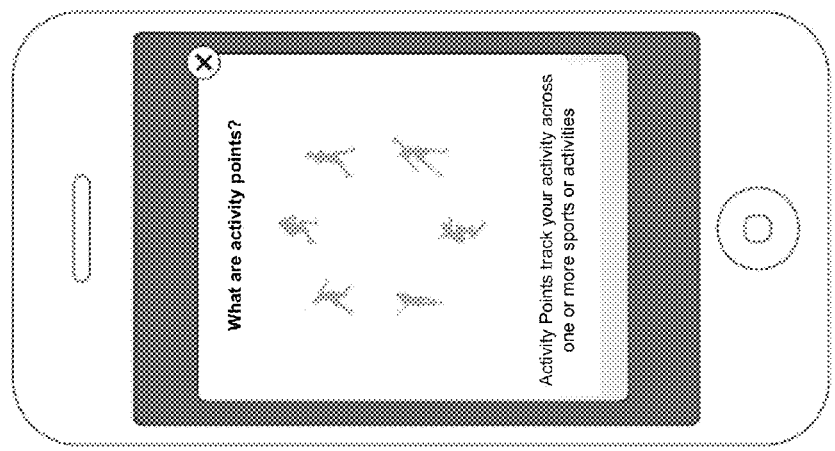
FIG. 20

| GAME TITLE | DESCRIPTION | METRICS |
|---|---|---|
| SHOOTING PRACTICE | Shoot around mode will allow players to use simple gestures on the device (tap/swipe) to keep track of every shot made or missed. | - Activity Points<br>- Play Time<br>- Made/Missed Shots<br>- Total Shots<br>- Shooting Percentage<br>- Hot Streak (Most shots made in a row)<br>- Vertical Sweet Spot (jump height of most shots made)<br>- Number of Balanced/Off-Balanced Shots |
| AROUND THE WORLD | Ballers practice quick transition jump shots by being prompted to shoot at a set number of specific spots around the mid-range or long-distance perimeter. The player can only advance to the next spot if the shot is made. The goal is to make all the shots in the least amount of time or with least amount of shot attempts. | - Activity Points<br>- Time Finished<br>- Made/Missed Shots<br>- Total Shots<br>- Shooting Percentage<br>- Hot Streak<br>- Quickness (Steps/Min)<br>- Average Vertical |
| BUZZER BEATERS | Ballers will begin by setting the shot clock time and increasing the level of distraction. Each level of the game will randomly pick a different type of shot that the user has to take: half-court, lay-ups, fade-away jumpers etc. Users may track made/missed shots using a gesture. | - Activity Points<br>- Made/Missed Shots<br>- Total Shots<br>- Shooting Percentage<br>- Quickness (Steps/Min)<br>- Fakes/Change of Direction<br>- Average Vertical |

FIG. 23

| GAME TITLE | DESCRIPTION | METRICS |
|---|---|---|
| PRO- PLAYER | In this inspirational game, players will be given a series of Pro classic movement videos and challenged to match the movements and stats of the Pro Player. If the player matches a high percentage of the Pro Player's stat, they will unlock a badge and exclusive content about the history of that shot. | - Activity Points<br>- Shot Accuracy: Percentage of Stats Matched to Pro)<br>- Vertical Jump (Pro vs Player)<br>- Airtime (Pro vs Player)<br>- Quickness (Pro vs Player)<br>- Fake/Change of Direction (Pro vs Player) |
| BASIC | This is a basic free mode feature within the app that allows users to quickly get statistics. Users will use this app to see how high they can jump or total airtime they can grab without having to go into the Track Games section. Ultimately, this feature can be used by ballers to create their own challenges and compare stats with their friends. | - Vertical Jump Height<br>- Airtime<br>- Quickness |
| AIR TIME | This non-shooting game allows players to strengthen the skill for rebounding and second hoops ability by keeping them to consistently throw a basketball against a backboard while in mid-air. The objective of the game is to max out their Total Airtime in a limited amount of time. | - Total Number of Jumps<br>- Total Airtime<br>- Top Airtime<br>- Second Jump Ability |

FIG. 24

| GAME TITLE | DESCRIPTION | METRICS |
|---|---|---|
| CONTINUOUS CROSSOVER | This game tests the user's ability to dribble between their legs as many times as possible in a set time period of time. Each dribble between the legs will be tracked by the player's feet movement (alternating split lunges). | - Total Number of Crossovers<br>- Quickness (lunges or steps per min)<br>- Hot Streak (top number of consecutive crossovers) |
| FREE THROW | To improve a player's free throw form consistency, this game tasks the user to shoot a predetermined number of free throw shots. The objective may not be to make the shots, but to shoot each shot with consistency of selected metrics (e.g., consistent balance). Meeting a specific gauge of balance (e.g., percentage) consistency may result in a higher score. Game levels may be integrated and with each advancement increases the level of noise and distraction. | - Balance Consistency (% of Shots Made with Consistent Balance)<br>- Percentage of Time on Toes<br>- Percentage of Time on Heels<br>- Balance Heat Map per Shot |
| SIGNATURE MOVES | This non-shooting game allows players to try and mimic the shots of Pro signature moves. This can be based on those signature moves that currently live on a website ; Similar to Pro-Moments, users can unlock exclusive tips and tricks from their favorite pros. | - Total Number of Jumps<br>- Total Airtime<br>- Top Airtime<br>- Second Jump Ability<br>- Fakes/Change of Direction |

FIG. 25

| GAME TITLE | DESCRIPTION | METRICS |
|---|---|---|
| PRO BATTLES | This shooting game allows users to choose a pro. to go into a shooting contest with. The player must shoot anywhere behind the 3-point line. If the player makes a shot, he or shy receives one point. If the player misses a shot, the pro receives 2 points. First player to 10 wins. Obviously, the object of the game is to make 10 3-pointers before you miss 5 3-pointers in order to win. | - Score (Player vs Pro)<br>- Made/Missed Shots<br>- Total Shots<br>- Shooting Percentage<br>- Vertical Sweet Spot (Jump height of most shots made)<br>- Number of Balanced/Off-Balanced Shots |
| H-O-R-S-E | This version of H.O.R.S.E can be played against a Pro or another player ___. For the Pro version, the user is challenged to makes a shot with specific ___ stats to match. If the user makes the shot, but does not match the ___ stats, the shot does not count. Similarly, for the multi-player version, users challenge each other with shots, but have to match the ___ stats as well. | - Total Number of Jumps<br>- Total Airtime<br>- Top Airtime<br>- Second Jump Ability<br>- Fakes/Change of Direction |

WORKOUT USER EXPERIENCE

CROSS REFERENCE TO RELATED APPLICATIONS

This application claims the benefit of, and priority to, U.S. Provisional Patent Application No. 61/601,601 filed Feb. 22, 2012, titled "Workout User Experience," 61/601,618 filed Feb. 22, 2012, titled "Basketball User Experience," and 61/601,604 filed Feb. 22, 2012, titled "Drill Challenges User Experience." The application also claims the benefit of, and priority to, U.S. patent application Ser. No. 13/399,452 filed Feb. 17, 2012, titled "Selecting and Correlating Physical Activity Data With Image Data," which claims priority to U.S. Provisional Patent Application No. 61/443,808 filed Feb. 17, 2011, titled "Tracking of User Performance Metrics During a Workout Session." The contents of all of the above listed applications are expressly incorporated herein by reference in their entirety for any and all non-limiting purposes.

BACKGROUND

Exercise and fitness have become increasingly popular and the benefits from such activities are well known. Various types of technology have been incorporated into fitness and other athletic activities. For example, a wide variety of portable electronic devices are available for use in fitness activity such as MP3 or other audio players, radios, portable televisions, DVD players, or other video playing devices, watches, GPS systems, pedometers, mobile telephones, pagers, beepers, etc. Many fitness enthusiasts or athletes use one or more of these devices when exercising or training to keep them entertained, provide performance data or to keep them in contact with others, etc. Such users have also demonstrated an interest in recording their athletic activities and metrics associated therewith. Accordingly, various sensors may be used to detect, store and/or transmit athletic performance information. Oftentimes, however, athletic performance information is presented in a vacuum or based on the overall athletic activity. Exercisers may be interested in obtaining additional information about their workouts.

SUMMARY

The following presents a general summary of example aspects to provide a basic understanding of example embodiments. This summary is not an extensive overview. It is not intended to identify key or critical elements or to delineate scope of the invention. The following summary merely presents some concepts of the invention in a general form as a prelude to the more detailed description provided below.

One or more aspects describe systems, apparatuses, computer readable media, and methods for tracking performance metrics of a user during an exercise session.

In some example aspects, the systems, apparatuses, computer readable media, and methods may be configured to process input specifying a user attribute, adjust a performance zone based on the user attribute, receive data generated by at least one of an accelerometer and a force sensor, determine whether the data is within the performance zone, and output the determination.

In some example aspects, the systems, apparatuses, computer readable media, and methods may include receiving data generated by a sensor (e.g., an accelerometer, a force sensor, temperature sensor, heart rate monitor, etc.) as a user performs an athletic movement, and comparing the data with comparison data of a plurality of playing styles to determine a particular one of the playing styles most closely matching the data.

In some example aspects, the systems, apparatuses, computer readable media, and methods may include receiving data generated by a force sensor indicating a weight distribution during a performance of a plurality of exercise tasks, processing first input indicating successful completion of an exercise task, associating a first weight distribution at a time preceding the first input with the successful completion of the exercise task, processing second input indicating unsuccessful completion of the exercise task, and associating a second weight distribution at a time preceding the second input with the unsuccessful completion of the exercise task.

In some example aspects, the systems, apparatuses, computer readable media, and methods may include receiving signature move data corresponding to acceleration and force measurement data measured by a first user performing a sequence of events, receiving player data from at least one of an accelerometer and a force sensor by monitoring a second user attempting to perform the sequence of events, and generating a similarity metric indicating how similar the player data is to the signature move data.

In some example aspects, the systems, apparatuses, computer readable media, and methods may include receiving data generated by at least one of an accelerometer and a force sensor, comparing the data to jump data to determine that the data is consistent with a jump, processing the data to determine a lift off time, a landing time, and a loft time, and calculating a vertical leap based on the loft time.

Other aspects and features are described throughout the disclosure.

BRIEF DESCRIPTION OF THE DRAWINGS

To understand the example embodiments, it will now be described by way of example, with reference to the accompanying drawings in which:

FIG. 9 illustrates example performance metrics for user selection in accordance with example embodiments.

FIGS. 10-11A illustrate an example of calibrating sensors in accordance with example embodiments.

FIG. 11B shows an example GUI showing shoe status that may be implemented in accordance with one embodiment.

FIGS. 23-26 illustrate example training sessions in accordance with example embodiments.

DETAILED DESCRIPTION

In the following description of the various embodiments, reference is made to the accompanying drawings, which form a part hereof, and in which is shown by way of illustration various embodiments in which the disclosure may be practiced. It is to be understood that other embodiments may be utilized and structural and functional modifications may be made without departing from the scope and spirit of the present disclosure. Further, headings within this disclosure should not be considered as limiting aspects of the disclosure. Those skilled in the art with the benefit of this disclosure will appreciate that the example embodiments are not limited to the example headings.

I. Example Personal Training System

A. Illustrative Computing Devices

Figure 1A:
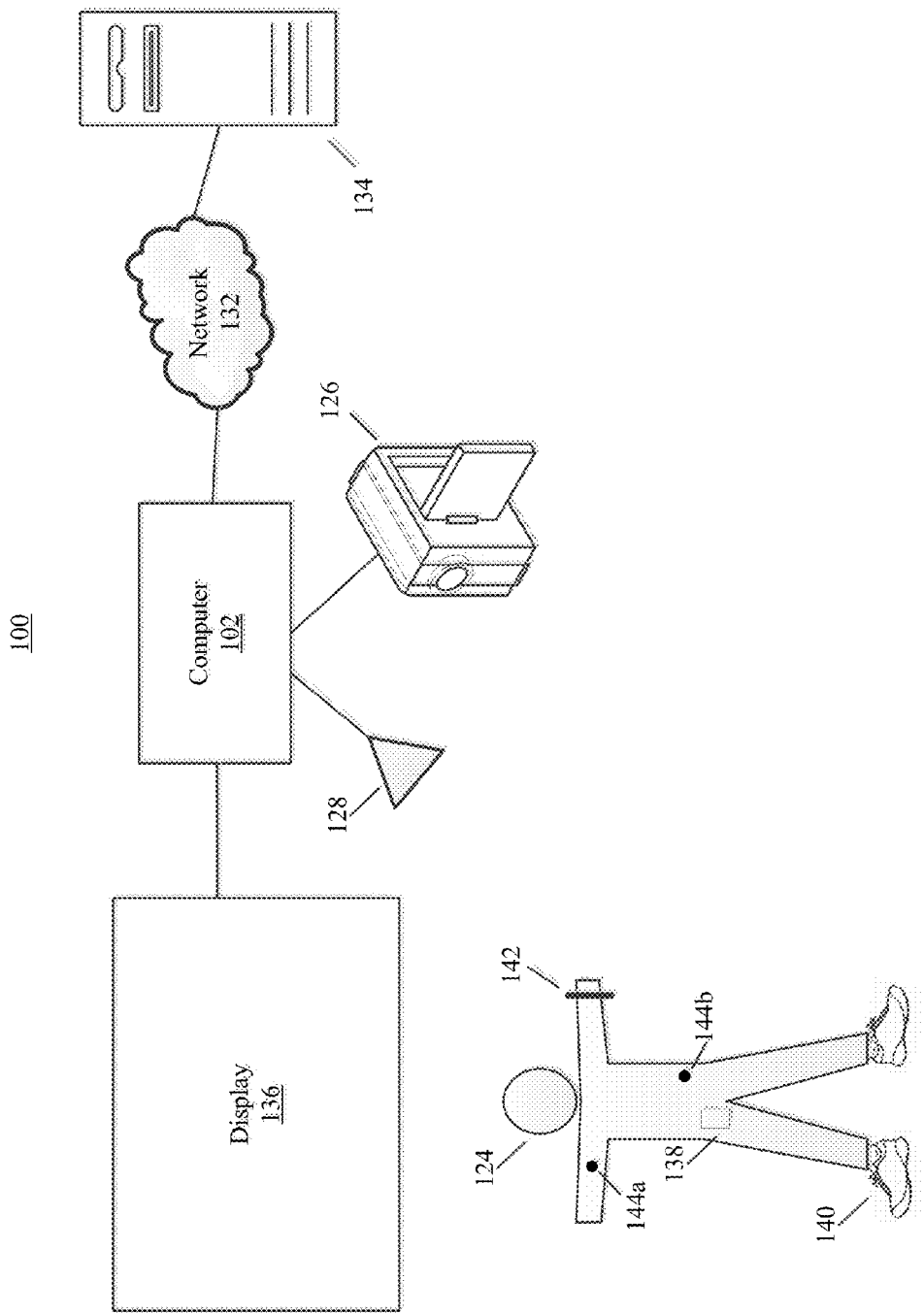
FIGS. 1A-B illustrate an example of a personal training system in accordance with example embodiments.

FIG. 1A illustrates an example of a personal training system 100 in accordance with example embodiments. Example system 100 may include one or more electronic devices, such as computer 102. Computer 102 may comprise a mobile terminal, such as a telephone, music player, tablet, netbook or any portable device. In other embodiments, computer 102 may comprise a set-top box (STB), desktop computer, digital video recorder(s) (DVR), computer server(s), and/or any other desired computing device. In certain configurations, computer 102 may comprise a gaming console, such as for example, a Microsoft® XBOX, Sony® Playstation, and/or a Nintendo® Wii gaming consoles. Those skilled in the art will appreciate that these are merely example consoles for descriptive purposes and this disclosure is not limited to any console or device.

Figure 1B:
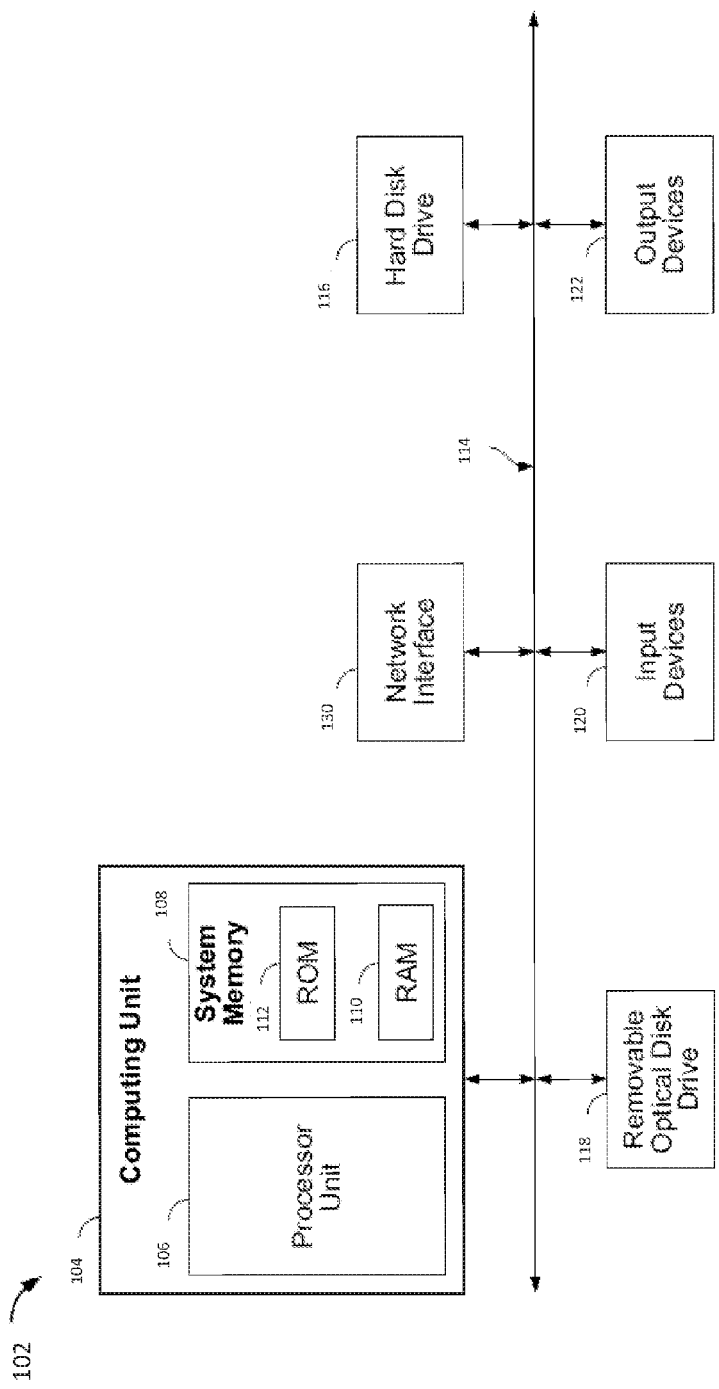

Turning briefly to FIG. 1B, computer 102 may include computing unit 104, which may comprise at least one processing unit 106. Processing unit 106 may be any type of processing device for executing software instructions, such as for example, a microprocessor device. Computer 102 may include a variety of non-transitory computer readable media, such as memory 108. Memory 108 may include, but is not limited to, random access memory (RAM) such as RAM 110, and/or read only memory (ROM), such as ROM 112. Memory 108 may include any of: electronically erasable programmable read only memory (EEPROM), flash memory or other memory technology, CD-ROM, digital versatile disks (DVD) or other optical disk storage, magnetic storage devices, or any other medium that can be used to store the desired information and that can be accessed by computer 102.

The processing unit 106 and the system memory 108 may be connected, either directly or indirectly, through a bus 114 or alternate communication structure to one or more peripheral devices. For example, the processing unit 106 or the system memory 108 may be directly or indirectly connected to additional memory storage, such as a hard disk drive 116, a removable magnetic disk drive, an optical disk drive 118, and a flash memory card. The processing unit 106 and the system memory 108 also may be directly or indirectly connected to one or more input devices 120 and one or more output devices 122. The output devices 122 may include, for example, a display device 136, television, printer, stereo, or speakers. In some embodiments one or more display devices may be incorporated into eyewear. The display devices incorporated into eyewear may provide feedback to users. Eyewear incorporating one or more display devices also provides for a portable display system. The input devices 120 may include, for example, a keyboard, touch screen, a remote control pad, a pointing device (such as a mouse, touchpad, stylus, trackball, or joystick), a scanner, a camera or a microphone. In this regard, input devices 120 may comprise one or more sensors configured to sense, detect, and/or measure athletic movement from a user, such as user 124, shown in FIG. 1A.

Looking again to FIG. 1A, image-capturing device 126 and/or sensor 128 may be utilized in detecting and/or measuring athletic movements of user 124. In one embodiment, data obtained from image-capturing device 126 or sensor 128 may directly detect athletic movements, such that the data obtained from image-capturing device 126 or sensor 128 is directly correlated to a motion parameter. Yet, in other embodiments, data from image-capturing device 126 and/or sensor 128 may be utilized in combination, either with each other or with other sensors to detect and/or measure movements. Thus, certain measurements may be determined from combining data obtained from two or more devices. Image-capturing device 126 and/or sensor 128 may include or be operatively connected to one or more sensors, including but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. Example uses of illustrative sensors 126, 128 are provided below in Section I.C, entitled "Illustrative Sensors." Computer 102 may also use touch screens or image capturing device to determine where a user is pointing to make selections from a graphical user interface. One or more embodiments may utilize one or more wired and/or wireless technologies, alone or in combination, wherein examples of wireless technologies include Bluetooth® technologies, Bluetooth® low energy technologies, and/or ANT technologies.

B. Illustrative Network

Computer 102, computing unit 104, and/or any other electronic devices may be directly or indirectly connected to one or more network interfaces, such as example interface 130 (shown in FIG. 1B) for communicating with a network, such as network 132. In the example of FIG. 1B, network interface 130, may comprise a network adapter or network interface card (NIC) configured to translate data and control signals from the computing unit 104 into network messages according to one or more communication protocols, such as the Transmission Control Protocol (TCP), the Internet Protocol (IP), and the User Datagram Protocol (UDP). These protocols are well known in the art, and thus will not be discussed here in more detail. An interface 130 may employ any suitable connection agent for connecting to a network, including, for example, a wireless transceiver, a power line adapter, a modem, or an Ethernet connection. Network 132, however, may be any one or more information distribution network(s), of any type(s) or topology(s), alone or in combination(s), such as internet(s), intranet(s), cloud(s), LAN(s). Network 132 may be any one or more of cable, fiber, satellite, telephone, cellular, wireless, etc. Networks are well known in the art, and thus will not be discussed here in more detail. Network 132 may be variously configured such as having one or more wired or wireless communication channels to connect one or more locations (e.g., schools, businesses, homes, consumer dwellings, network resources, etc.), to one or more remote servers 134, or to other computers, such as similar or identical to computer 102. Indeed, system 100 may include more than one instance of each component (e.g., more than one computer 102, more than one display 136, etc.).

Regardless of whether computer 102 or other electronic device within network 132 is portable or at a fixed location, it should be appreciated that, in addition to the input, output and storage peripheral devices specifically listed above, the computing device may be connected, such as either directly, or through network 132 to a variety of other peripheral devices, including some that may perform input, output and storage functions, or some combination thereof. In certain embodiments, a single device may integrate one or more components shown in FIG. 1A. For example, a single device may include computer 102, image-capturing device 126, sensor 128, display 136 and/or additional components. In one embodiment, sensor device 138 may comprise a mobile terminal having a display 136, image-capturing device 126, and one or more sensors 128. Yet, in another embodiment, image-capturing device 126, and/or sensor 128 may be peripherals configured to be operatively connected to a media device, including for example, a gaming or media system. Thus, it goes from the foregoing that this disclosure is not limited to stationary systems and methods. Rather, certain embodiments may be carried out by a user 124 in almost any location.

C. Illustrative Sensors

Computer 102 and/or other devices may comprise one or more sensors 126, 128 configured to detect and/or monitor at least one fitness parameter of a user 124. Sensors 126 and/or 128 may include, but are not limited to: an accelerometer, a gyroscope, a location-determining device (e.g., GPS), light sensor, temperature sensor (including ambient temperature and/or body temperature), sleep pattern sensors, heart rate monitor, image-capturing sensor, moisture sensor and/or combinations thereof. Network 132 and/or computer 102 may be in communication with one or more electronic devices of system 100, including for example, display 136, an image capturing device 126 (e.g., one or more video cameras), and sensor 128, which may be an infrared (IR) device. In one embodiment sensor 128 may comprise an IR transceiver. For example, sensors 126, and/or 128 may transmit waveforms into the environment, including towards the direction of user 124 and receive a "reflection" or otherwise detect alterations of those released waveforms. In yet another embodiment, image-capturing device 126 and/or sensor 128 may be configured to transmit and/or receive other wireless signals, such as radar, sonar, and/or audible information. Those skilled in the art will readily appreciate that signals corresponding to a multitude of different data spectrums may be utilized in accordance with various embodiments. In this regard, sensors 126 and/or 128 may detect waveforms emitted from external sources (e.g., not system 100). For example, sensors 126 and/or 128 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology. As a non-limited example, image-capturing devices configured to perform range phenomenology are commercially available from Flir Systems, Inc. of Portland, Oreg. Although image capturing device 126 and sensor 128 and display 136 are shown in direct (wirelessly or wired) communication with computer 102, those skilled in the art will appreciate that any may directly communicate (wirelessly or wired) with network 132.

1. Multi-Purpose Electronic Devices

User 124 may possess, carry, and/or wear any number of electronic devices, including sensory devices 138, 140, 142, and/or 144. In certain embodiments, one or more devices 138, 140, 142, 144 may not be specially manufactured for fitness or athletic purposes. Indeed, aspects of this disclosure relate to utilizing data from a plurality of devices, some of which are not fitness devices, to collect, detect, and/or measure athletic data. In one embodiment, device 138 may comprise a portable electronic device, such as a telephone or digital music player, including an IPOD®, IPAD®, or iPhone®, brand devices available from Apple, Inc. of Cupertino, Calif. or Zune® or Microsoft® Windows devices available from Microsoft of Redmond, Wash. As known in the art, digital media players can serve as both an output device for a computer (e.g., outputting music from a sound file or pictures from an image file) and a storage device. In one embodiment, device 138 may be computer 102, yet in other embodiments, computer 102 may be entirely distinct from device 138. Regardless of whether device 138 is configured to provide certain output, it may serve as an input device for receiving sensory information. Devices 138, 140, 142, and/or 144 may include one or more sensors, including but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. In certain embodiments, sensors may be passive, such as reflective materials that may be detected by image-capturing device 126 and/or sensor 128 (among others). In certain embodiments, sensors 144 may be integrated into apparel, such as athletic clothing. For instance, the user 124 may wear one or more on-body sensors 144a-b. Sensors 144 may be incorporated into the clothing of user 124 and/or placed at any desired location of the body of user 124. Sensors 144 may communicate (e.g., wirelessly) with computer 102, sensors 128, 138, 140, and 142, and/or camera 126. Examples of interactive gaming apparel are described in U.S. patent application Ser. No. 10/286,396, filed Oct. 30, 2002, and published as U.S. Pat. Pub, No. 2004/0087366, the contents of which are incorporated herein by reference in its entirety for any and all non-limiting purposes. In certain embodiments, passive sensing surfaces may reflect waveforms, such as infrared light, emitted by image-capturing device 126 and/or sensor 128. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Devices 138-144, as well as any other electronic device disclosed herein, including any sensory device, may communicate with each other, either directly or through a network, such as network 132. Communication between one or more of devices 138-144 may take place via computer 102. For example, two or more of devices 138-144 may be peripherals operatively connected to bus 114 of computer 102. In yet another embodiment, a first device, such as device 138 may communicate with a first computer, such as computer 102 as well as another device, such as device 142, however, device 142 may not be configured to connect to computer 102 but may communicate with device 138. Further, one or more electronic devices may be configured to communicate through multiple communication pathways. For example, device 140 may be configured to communicate via a first wireless communication protocol with device 138 and further communicate through a second wireless communication protocol with a different device, such as for example, computer 102. Example wireless protocols are discussed throughout this disclosure and are known in the art. Those skilled in the art will appreciate that other configurations are possible.

Some implementations of the example embodiments may alternately or additionally employ computing devices that are intended to be capable of a wide variety of functions, such as a desktop or laptop personal computer. These computing devices may have any combination of peripheral devices or additional components as desired. Also, the components shown in FIG. 1B may be included in the server 134, other computers, apparatuses, etc.

2. Illustrative Apparel/Accessory Sensors

In certain embodiments, sensory devices 138, 140, 142 and/or 144 may be formed within or otherwise associated with user's 124 clothing or accessories, including a watch, armband, wristband, necklace, shirt, shoe, or the like. Examples of shoe-mounted and wrist-worn devices (devices 140 and 142, respectively) are described immediately below, however, these are merely example embodiments and this disclosure should not be limited to such.

i. Shoe-Mounted Device

In certain embodiments, sensory device 140 may comprise footwear which may include one or more sensors, including but not limited to: an accelerometer, location-sensing components, such as GPS, and/or a force sensor system. FIG. 2A illustrates one example embodiment of a sensor system 202 in accordance with example embodiments. In certain embodiments, system 202 may include a sensor assembly 204. Assembly 204 may comprise one or more sensors, such as for example, an accelerometer, location-determining components, and/or force sensors. In the illustrated embodiment, assembly 204 incorporates a plurality of sensors, which may include force-sensitive resistor (FSR) sensors 206. In yet other embodiments, other sensor(s) may be utilized. Port 208 may be positioned within a sole structure 209 of a shoe. Port 208 may optionally be provided to be in communication with an electronic module 210 (which may be in a housing 211) and a plurality of leads 212 connecting the FSR sensors 206 to the port 208. Module 210 may be contained within a well or cavity in a sole structure of a shoe. The port 208 and the module 210 include complementary interfaces 214, 216 for connection and communication.

In certain embodiments, at least one force-sensitive resistor 206 shown in FIG. 2A may contain first and second electrodes or electrical contacts 218, 220 and a force-sensitive resistive material 222 disposed between the electrodes 218, 220 to electrically connect the electrodes 218, 220 together. When pressure is applied to the force-sensitive material 222, the resistivity and/or conductivity of the force-sensitive material 222 changes, which changes the electrical potential between the electrodes 218, 220. The change in resistance can be detected by the sensor system 202 to detect the force applied on the sensor 216. The force-sensitive resistive material 222 may change its resistance under pressure in a variety of ways. For example, the force-sensitive material 222 may have an internal resistance that decreases when the material is compressed, similar to the quantum tunneling composites described in greater detail below. Further compression of this material may further decrease the resistance, allowing quantitative measurements, as well as binary (on/off) measurements. In some circumstances, this type of force-sensitive resistive behavior may be described as "volume-based resistance," and materials exhibiting this behavior may be referred to as "smart materials." As another example, the material 222 may change the resistance by changing the degree of surface-to-surface contact. This can be achieved in several ways, such as by using microprojections on the surface that raise the surface resistance in an uncompressed condition, where the surface resistance decreases when the microprojections are compressed, or by using a flexible electrode that can be deformed to create increased surface-to-surface contact with another electrode. This surface resistance may be the resistance between the material 222 and the electrodes 218, 220 and/or the surface resistance between a conducting layer (e.g., carbon/graphite) and a force-sensitive layer (e.g., a semiconductor) of a multi-layer material 222. The greater the compression, the greater the surface-to-surface contact, resulting in lower resistance and enabling quantitative measurement. In some circumstances, this type of force-sensitive resistive behavior may be described as "contact-based resistance." It is understood that the force-sensitive resistive material 222, as defined herein, may be or include a doped or non-doped semiconducting material.

The electrodes 218, 220 of the FSR sensor 206 can be formed of any conductive material, including metals, carbon/ graphite fibers or composites, other conductive composites, conductive polymers or polymers containing a conductive material, conductive ceramics, doped semiconductors, or any other conductive material. The leads 212 can be connected to the electrodes 218, 220 by any suitable method, including welding, soldering, brazing, adhesively joining, fasteners, or any other integral or non-integral joining method. Alternately, the electrode 218, 220 and associated lead 212 may be formed of a single piece of the same material.

Other embodiments of the sensor system 202 may contain a different quantity and/or configuration of sensors and generally include at least one sensor. For example, in one embodiment, the system 202 includes a much larger number of sensors, and in another embodiment, the system 202 includes two sensors, one in the heel and one in the forefoot of a shoe or device to be close proximity to a user's foot. In addition, one or more sensors 206 may communicate with the port 214 in a different manner, including any known type of wired or wireless communication, including Bluetooth and near-field communication. A pair of shoes may be provided with sensor systems 202 in each shoe of the pair, and it is understood that the paired sensor systems may operate synergistically or may operate independently of each other, and that the sensor systems in each shoe may or may not communicate with each other. It is further understood that the sensor system 202 may be provided with computer-executable instructions stored on one or more computer-readable media that when executed by a processor control collection and storage of data (e.g., pressure data from interaction of a user's foot with the ground or other contact surface), and that these executable instructions may be stored in and/or executed by the sensors 206, any module, and/or an external device, such as device 128, computer 102, server 134 and/or network 132 of FIG. 1A.

ii. Wrist-Worn Device

Figure 2B:
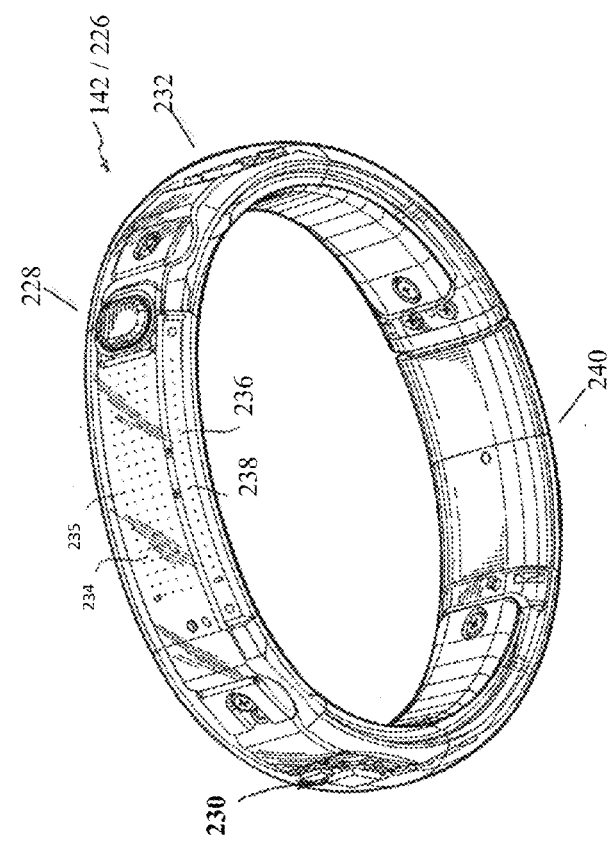
FIGS. 2A-B illustrate example embodiments of a sensor system in accordance with example embodiments.
Figure 2A:
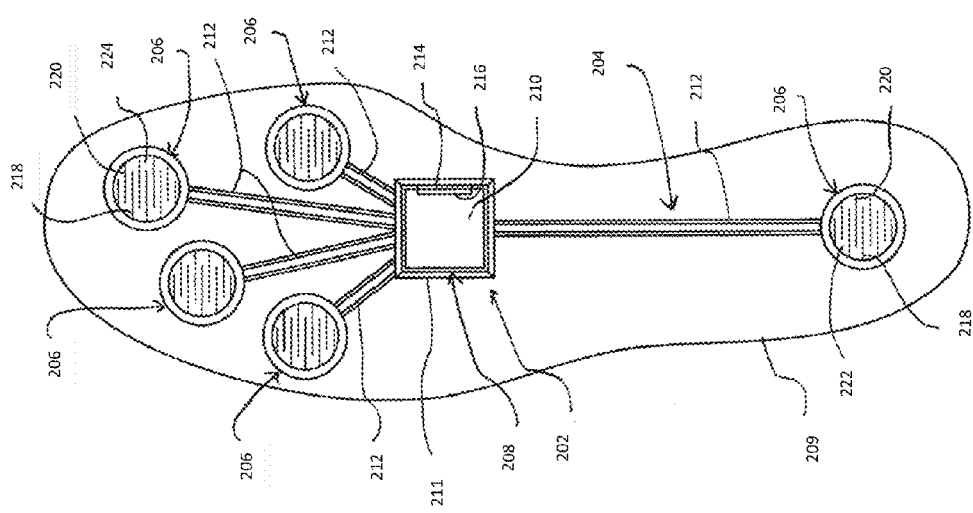

As shown in FIG. 2B, device 226 (which may resemble or be sensory device 142 shown in FIG. 1A) may be configured to be worn by user 124, such as around a wrist, arm, ankle or the like. Device 226 may monitor athletic movements of a user, including all-day activity of user 124. In this regard, device assembly 226 may detect athletic movement during user's 124 interactions with computer 102 and/or operate independently of computer 102. For example, in one embodiment, device 226 may be an-all day activity monitor that measures activity regardless of the user's proximity or interactions with computer 102. Device 226 may communicate directly with network 132 and/or other devices, such as devices 138 and/or 140. In other embodiments, athletic data obtained from device 226 may be utilized in determinations conducted by computer 102, such as determinations relating to which exercise programs are presented to user 124. In one embodiment, device 226 may also wirelessly interact with a mobile device, such as device 138 associated with user 124 or a remote website such as a site dedicated to fitness or health related subject matter. At some predetermined time, the user may wish to transfer data from the device 226 to another location.

As shown in FIG. 2B, device 226 may include an input mechanism, such as a depressible input button 228 assist in operation of the device 226. The input button 228 may be operably connected to a controller 230 and/or any other electronic components, such as one or more of the elements discussed in relation to computer 102 shown in FIG. 1B. Controller 230 may be embedded or otherwise part of housing 232. Housing 232 may be formed of one or more materials, including elastomeric components and comprise one or more displays, such as display 234. The display may be considered an illuminable portion of the device 226. The display 234 may include a series of individual lighting elements or light members such as LED lights 234 in an exemplary embodiment. The LED lights may be formed in an array and operably connected to the controller 230. Device 226 may include an indicator system 236, which may also be considered a portion or component of the overall display 234. It is understood that the indicator system 236 can operate and illuminate in conjunction with the display 234 (which may have pixel member 235) or completely separate from the display 234. The indicator system 236 may also include a plurality of additional lighting elements or light members 238, which may also take the form of LED lights in an exemplary embodiment. In certain embodiments, indicator system may provide a visual indication of goals, such as by illuminating a portion of lighting members 238 to represent accomplishment towards one or more goals.

A fastening mechanism 240 can be unlatched wherein the device 226 can be positioned around a wrist of the user 124 and the fastening mechanism 240 can be subsequently placed in a latched position. The user can wear the device 226 at all times if desired. In one embodiment, fastening mechanism 240 may comprise an interface, including but not limited to a USB port, for operative interaction with computer 102 and/or devices 138, 140.

In certain embodiments, device 226 may comprise a sensor assembly (not shown in FIG. 2B). The sensor assembly may comprise a plurality of different sensors. In an example embodiment, the sensor assembly may comprise or permit operative connection to an accelerometer (including in the form of a multi-axis accelerometer), heart rate sensor, location-determining sensor, such as a GPS sensor, and/or other sensors. Detected movements or parameters from device's 142 sensor(s), may include (or be used to form) a variety of different parameters, metrics or physiological characteristics including but not limited to speed, distance, steps taken, calories, heart rate, sweat detection, effort, oxygen consumed, and/or oxygen kinetics. Such parameters may also be expressed in terms of activity points or currency earned by the user based on the activity of the user.

Various examples may be implemented using electronic circuitry configured to perform one or more functions. For example, with some embodiments of the invention, a computing device such as a smart phone, mobile device, computer, server, or other computing equipment may be implemented using one or more application-specific integrated circuits (ASICs). More typically, however, components of various examples of the invention will be implemented using a programmable computing device executing firmware or software instructions, or by some combination of purpose-specific electronic circuitry and firmware or software instructions executing on a programmable computing device.

II. Monitoring System

Figure 3A:
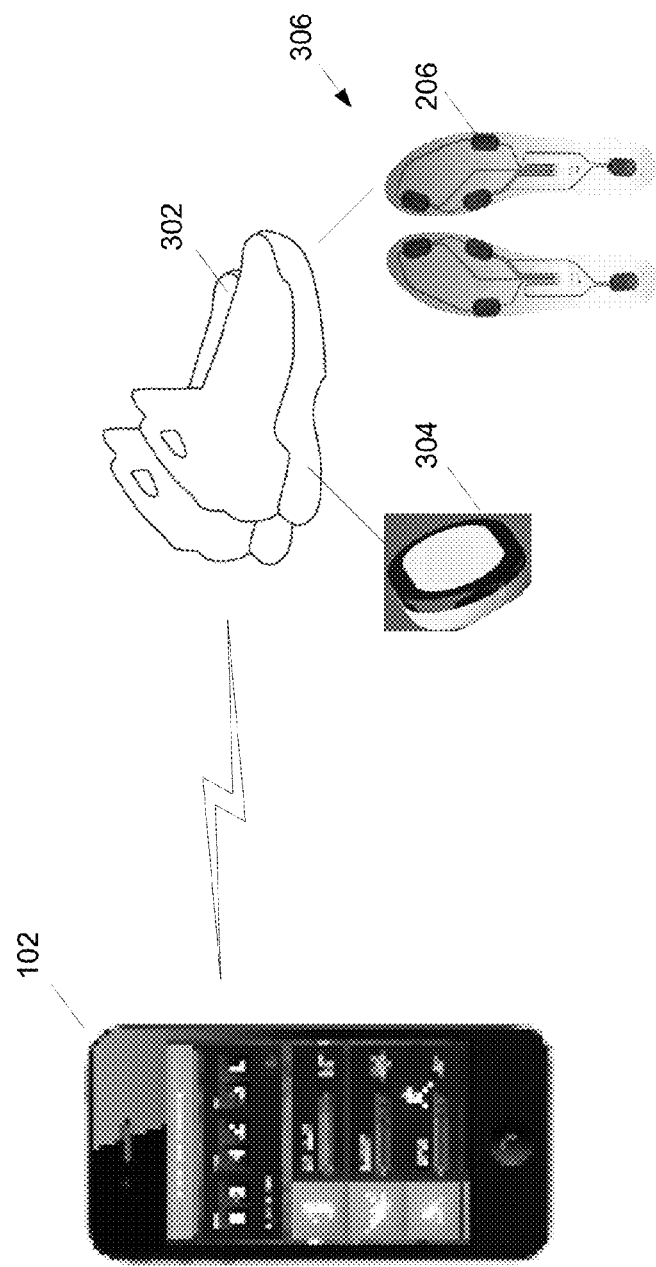
FIGS. 3A-B illustrate an example of a computer interacting with at least one sensor in accordance with example embodiments.
Figure 3B:
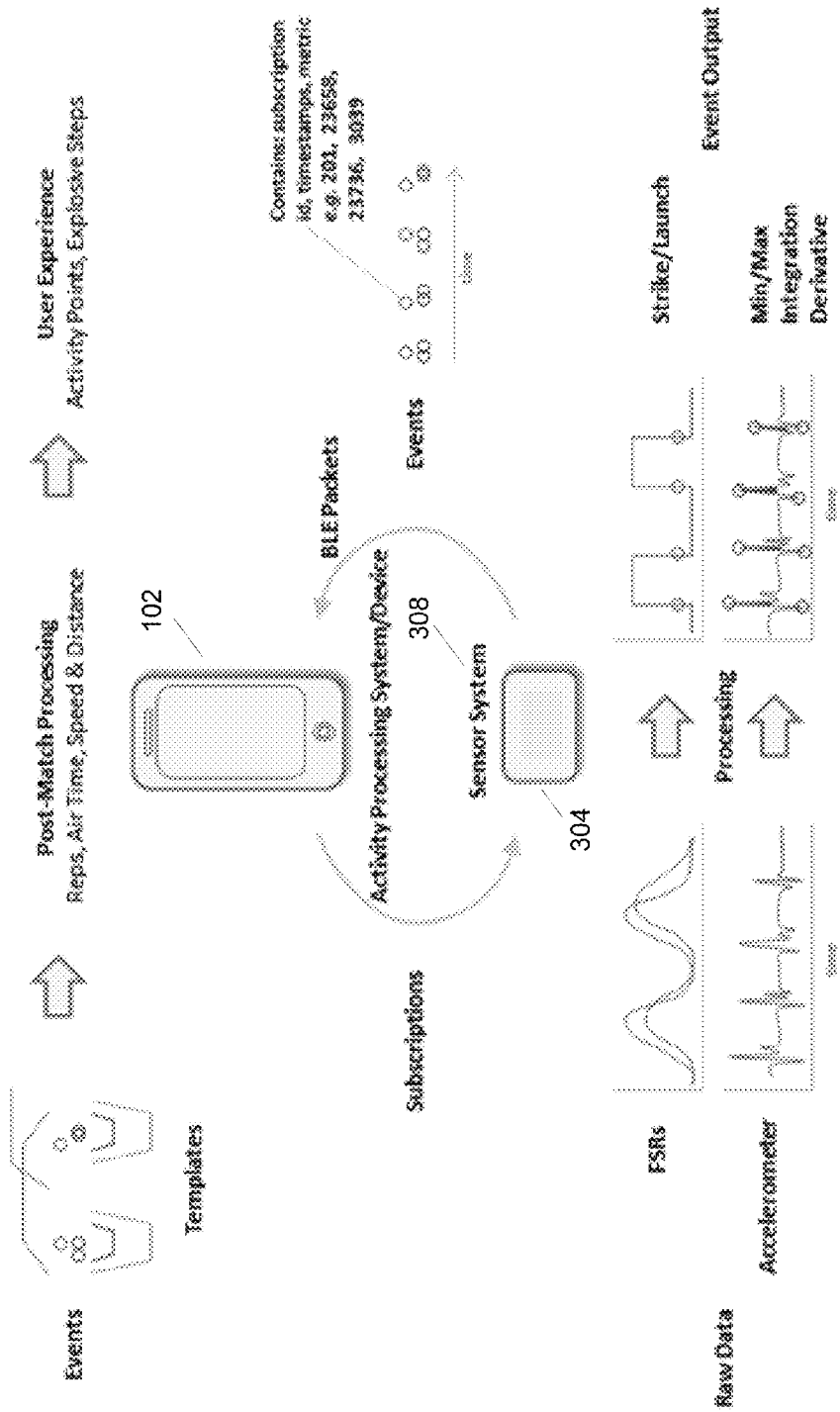

FIGS. 3A-B illustrate examples of a computer interacting with at least one sensor in accordance with example embodiments. In the depicted example, the computer 102 may be implemented as a smart phone that may be carried by the user. Example sensors may be worn on a user's body, be situated off-body, and may include any of the sensors discussed above including an accelerometer, a distributed sensor, a heart rate monitor, a temperature sensor, etc. In FIG. 3, a pod sensor 304 and a distributed sensor 306 (including, for example, sensor system 202 discussed above having one or more FSRs 206) is shown. The pod sensor 304 may include an accelerometer, a gyroscope, and/or other sensing technology. In some examples, pod sensor 304 may at least one sensor to monitor data that does not directly relate to user movement. For example, ambient sensors may be worn by the user or may be external to the user. Ambient sensors may include a temperature sensor, a compass, a barometer, a humidity sensor, or other type of sensor. Other types of sensors and combinations of sensors configured to measure user movement may also be used. Also, computer 102 may incorporate one or more sensors.

The pod sensor 304, the distributed sensor 206, as well as other types of sensors, may include a wireless transceiver to communicate with one another and the computer 102. For example, sensors 304 and 306 may communicate directly with the network 132, with other devices worn by the user (e.g., a watch, arm band device, etc.), with sensors or devices worn by a second user, an external device, etc. In an example, a sensor in a left shoe may communicate with a sensor in a right shoe. Also, one shoe may include multiple sensors that communicate with one another and/or with a processor of the shoe. Further, a pair of shoes may include a single processor that collects data from multiple sensors associated with the shoes, and a transceiver coupled to the single processor may communicate sensor data to at least one of computer 102, network 132, and server 134. In another example, one or more sensors of a shoe may communicate to a transceiver that communicates with at least one of computer 102, network 132, and server 134. Further, sensors associated with a first user may communicate with sensors associated with a second user. For example, sensors in the first user's shoes may communicate with sensors in a second user's shoes. Other topographies may also be used.

The computer 102 may exchange data with the sensors, and also may communicate data received from the sensors via the network 132 to the server 134 and/or to another computer 102. A user may wear head phones or ear buds to receive audio information from the computer 102, directly from one or more of the sensors, from the server 134, from the network 132, from other locations, and combinations thereof. The head phones may be wired or wireless. For example, a distributed sensor 306 may communicate data to head phones for audible output to the user.

In an example, a user may wear shoes that are each equipped with an accelerometer, a force sensor or the like, to allow the computer 102 and/or the server 134 to determine the individual movement and metrics of each foot or other body part (e.g., leg, hand, arm, individual fingers or toes, regions of a person's foot or leg, hips, chest, shoulders, head, eyes) alone or in combination with the systems described above with reference to FIGS. 1A-B and 2A-2B.

Processing of data may distributed in any way, or performed entirely at one shoe, at the computer 102, in the server 134, or combinations thereof. In the description below, computer 102 may be described as performing a function. Other devices, including server 134, a controller, another computer, a processor in a shoe or other article of clothing, or other device may performing the function instead of or in addition to computer 102. For example, one or more sensors of each shoe (or other peripheral sensor) could be mated with a respective, local controller that performs some or all processing of raw signal output by one or more sensors. The controller's processing, at any given time, may be subject to command and control of a higher tiered computing device (e.g., computer 102). That higher tiered device may receive and further process the processed sensor signals, from that one or plural controllers, e.g., via one or more transceivers. Comparisons and calculations may be made at one or more computing devices, including some or all of the above computing devices, with or without additional computing devices. Sensors may sense desired conditions and generate raw signals, the raw signals being processed so as to provide processed data. The processed data may then be used for determining current performance metrics (e.g., current speed of travel, etc.) and the determinations may change depending on user input (e.g., how high did I jump?) and/or programming (e.g., did the user do the indicated exercise and, if that is detected, how is it qualified/quantified in the user experience).

In an example, sensors 304 and 306 may process and store measurement data, and forward the processed data (e.g., average acceleration, highest speed, total distance, etc.) to the computer 102 and/or the server 134. The sensors 304 and 306 may also send raw data to the computer 102 and/or the server 134 for processing. Raw data, for example, may include an acceleration signal measured by an accelerometer over time, a pressure signal measured by a pressure sensor over time, etc. Examples of multi-sensor apparel and the use of multiple sensors in athletic activity monitoring are described in U.S. application Ser. No. 12/483,824, entitled "FOOTWEAR HAVING SENSOR SYSTEM," and published as U.S. Publication No. 2010/0063778 A1 and U.S. application Ser. No. 12/483,828, entitled "FOOTWEAR HAVING SENSOR SYSTEM," and published as U.S. Publication No. 2010/0063779 A1. The content of the above referenced applications are incorporated herein by reference in their entirety. In a particular example, an athlete may wear shoes 302 having one or more force sensing systems, e.g., that utilize force-sensitive resistor (FSR) sensors, as shown in FIG. 2A and described in the above noted patent publications. The shoe 302 may have multiple FSR sensors 206 that detect forces at different regions of the user's foot (e.g., a heel, mid-sole, toes, etc.). Computer 102 may process data from FSR sensors 206 to determine balance of a user's foot and/or between a user's two feet. For example, computer 102 may compare a force measurement by a FSR 206 from a left shoe relative to a force measurement by a FSR 206 from a right shoe to determine balance and/or weight distribution.

FIG. 3B is another example data flow diagram in which computer 102 interacts with at least one sensor processing system 308 to detect user actions. Sensor processing system 308 may be physically separate and distinct from computer 102 and may communicate with computer 102 through wired or wireless communication. Sensor processing system 308 may include sensor 304, as shown, as well as other sensors (e.g., sensor 306) instead of or in addition to sensor 304. In the depicted example, sensor system 308 may receive and process data from sensor 304 and FSR sensor 206. Computer 102 may receive input from a user about a type of activity session (e.g., cross training, basketball, running, etc.) the user desires to perform. Instead or additionally, computer 102 may detect a type of activity the user is performing or receive information from another source about the type of activity being performed.

Based on activity type, computer 102 may identify one or more predefined action templates and communicate a subscription to sensor system 308. Action templates may be used to identify motions or actions that a user may perform while performing the determined type of activity. For example, an action may correspond to a group of one or more events, such as detecting that a user has taken a step to the right followed by a step to the left or detecting that a user has jumped while flicking his or her wrist. Accordingly, different sets of one or more action templates may be defined for different types of activities. For example, a first set of action templates defined for basketball may include dribbling, shooting a basketball, boxing out, performing a slam dunk, sprinting and the like. A second set of action templates defined for soccer may include kicking a ball to make a shot, dribbling, stealing, heading the ball and the like. Action templates may correspond to any desired level of granularity. In some examples, a particular type of activity may include 50-60 templates. In other examples, a type of activity may correspond to 20-30 templates. Any number of templates may be defined as needed for a type of activity. In still other examples, the templates may be manually selected by a user rather than being selected by the system.

Sensor subscriptions may allow sensor system 308 to select the sensors from which data is to be received. The sensor processing system 308 may manage subscriptions that are used at any particular time. Types of subscriptions may include force sensitive resistance data from one or more force sensitive resistors, acceleration data from one or more accelerometers, summation information over multiple sensors (e.g., summation of acceleration data, summation of force resistance data over one or more sensors, etc.), pressure maps, mean centered data, gravity adjusted sensor data, force sensitive resistance derivatives, acceleration derivatives, and the like and/or combinations thereof. In some examples, a single subscription may correspond to a summation of data from multiple sensors. For example, if a template calls for a shift in force to the forefoot region of a user's foot, a single subscription may correspond to a summation of forces of all sensors in the forefoot region. Alternatively or additionally, force data for each of the forefoot force sensors may correspond to a distinct subscription.

For example, if sensor system 308 includes 4 force sensitive resistive sensors and an accelerometer, the subscriptions may specify which of those 5 sensors are monitored for sensor data. In another example, subscriptions may specify receiving/monitoring sensor data from a right shoe accelerometer but not a left shoe accelerometer. In yet another example, a subscription may include monitoring data from a wrist-worn sensor but not a heart rate sensor. Subscriptions may also specify sensor thresholds to adjust the sensitivity of a sensor system's event detection process. Thus, in some activities, sensor system 308 may be instructed to detect all force peaks above a first specified threshold. For other activities, sensor system 308 may be instructed to detect all force peaks above a second specified threshold. Use of different sensor subscriptions may help a sensor system to conserve power if some sensor readings are not needed for a particular activity. Accordingly, different activities and activity types may use different sensor subscriptions.

Sensor processing system 308 may be configured to perform initial processing of raw sensor data to detect various granular events. Examples of events may include a foot strike or launch when jumping, a maximum acceleration during a time period, etc. Sensor system 308 may then pass events to computer 102 for comparison to various templates to determine whether an action has been performed. For example, sensor system 308 may identify one or more events and wirelessly communicate BLUETOOTH® Low Energy (BLE) packets, or other types of data, to computer 102. In another example, sensor system 308 may instead or additionally send raw sensor data.

Subsequent to receipt of the events and/or the raw sensor data, computer 102 may perform post-match processing including determining various activity metrics such as repetitions, air-time, speed, distance and the like. Activity classification may be performed by identifying various events and actions represented within data received from any number and type of sensors. Accordingly, activity tracking and monitoring may include determining whether one or more expected or known actions within an activity type has been performed and metrics associated with those actions. In one example, actions may correspond to a series of one or more low-level or granular events and may be detected using predefined action templates.

For example, using action templates, computer 102 may automatically detect when a user has performed a particular activity or a particular motion expected during that activity. If a user is playing basketball, for instance, detecting that the user has jumped while flicking his or her wrist may indicate that the user has taken a shot. In another example, detecting that a user has moved both feet outward while jumping followed by moving both feet inward while jumping may register as a user performing one repetition of a jumping jack exercise. A variety of other templates may be defined as desired to identify particular types of activities, actions or movements within types of activities.

Figure 4:
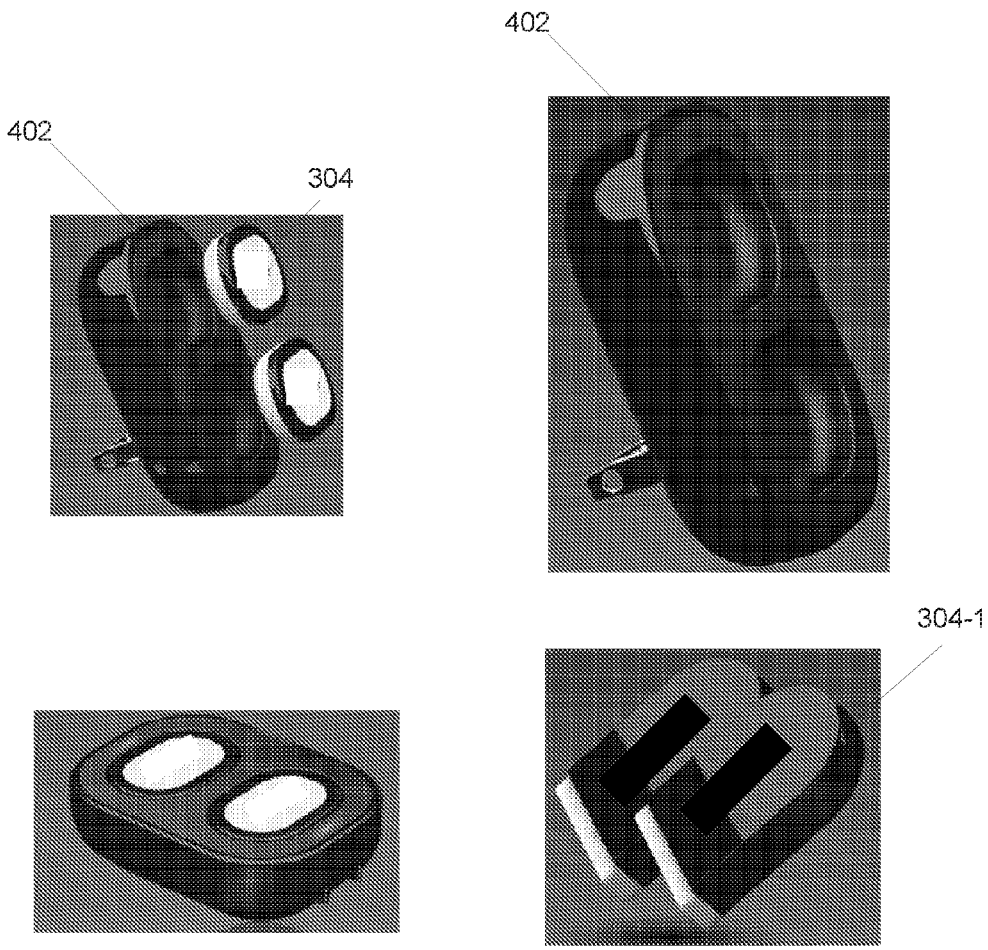
FIG. 4 illustrates examples of pod sensors that may be embedded and removed from a shoe in accordance with example embodiments.

FIG. 4 illustrates examples of pod sensors 304 that may be embedded and removed from a shoe in accordance with example embodiments. The pod sensor 304 may include a rechargeable battery that may be recharged when inserted into a wall adapter 402. Wired or wireless charging of the pod sensor 304 may be used. For example, the pod sensor 304 may be inductively charged. In some examples, a pod sensor 304-1 may be configured with an interface (e.g., Universal Serial Bus) permitting insertion into a computer or other device for downloading and/or receiving data. An interface of the pod sensor may provide for wired or wireless communication. For instance, software updates may be loaded onto the pod sensor when connected to a computer. Also, the pod sensor may wirelessly receive software updates. When physically coupled to a computer 102 (or other device having a port), the pod sensor may charge and communicate with the computer 102.

Figure 5:
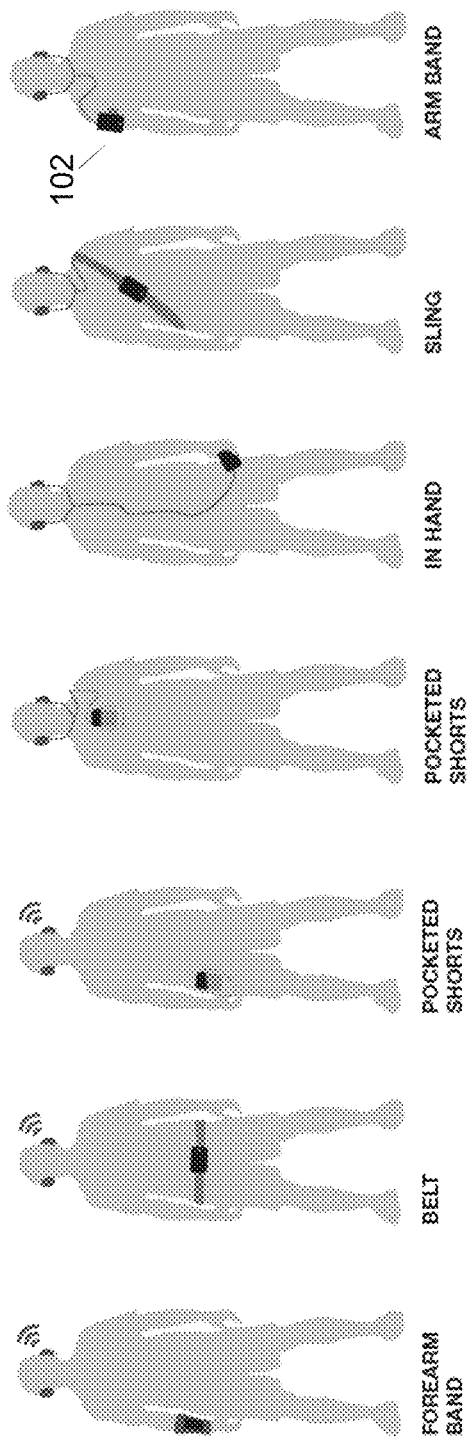
FIG. 5 illustrates example on-body configurations for a computer in accordance with example embodiments.

FIG. 5 illustrates example on-body configurations for the computer 102 in accordance with example embodiments. Computer 102 may be configured to be worn at desired locations on a user's body, such as, for example, a user's arm, leg, or chest, or otherwise integrated in clothing. For example, each article of clothing may have its own integrated computer. The computer may be a thin client, driven by the context, of what the user is doing and otherwise equipped/networked. Computer 102 may also be located apart from the user's body, as shown in FIGS. 6-7.

Figure 6:
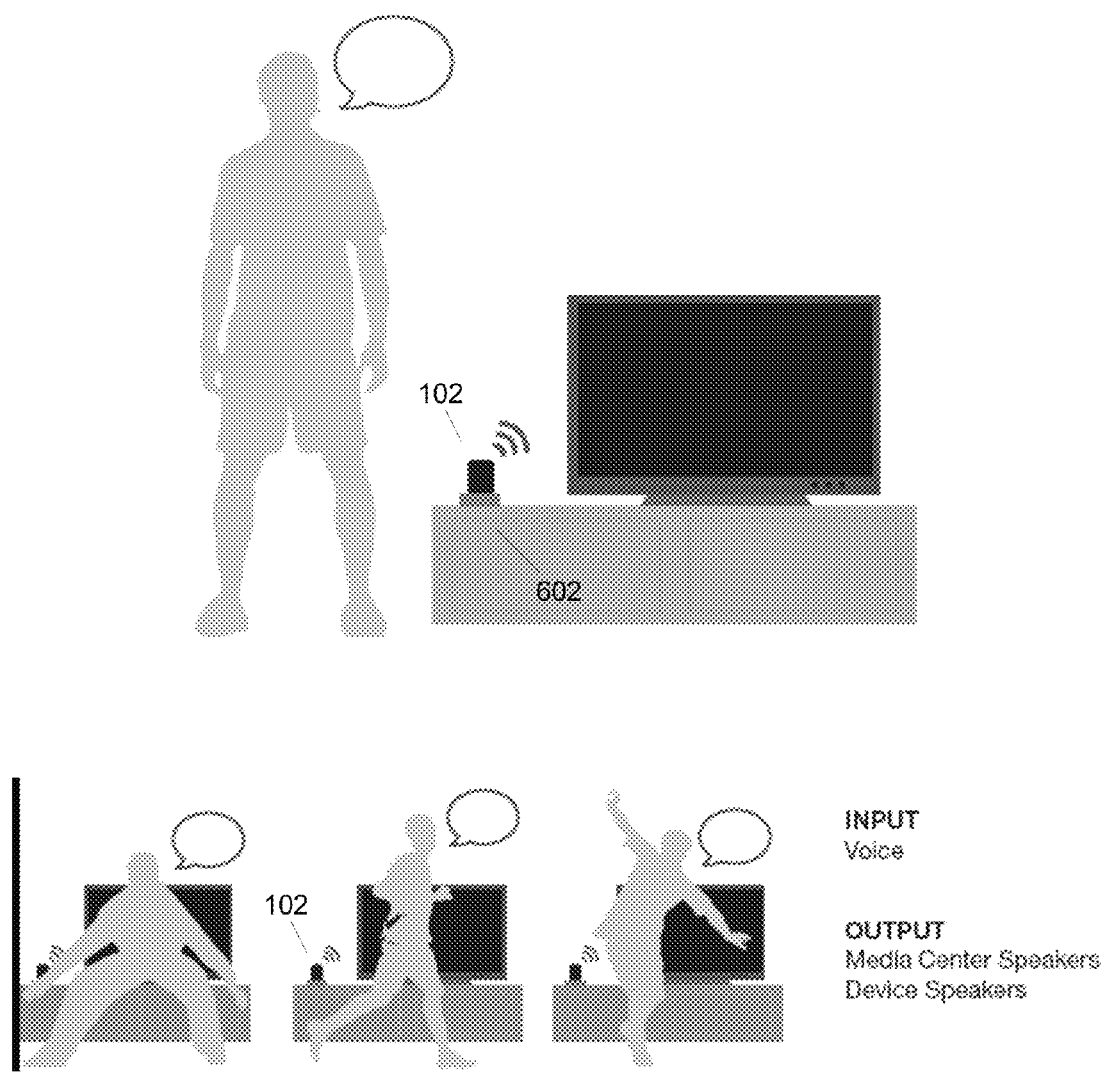
FIGS. 6-7 illustrates example various off-body configurations for a computer in accordance with example embodiments.
Figure 7:
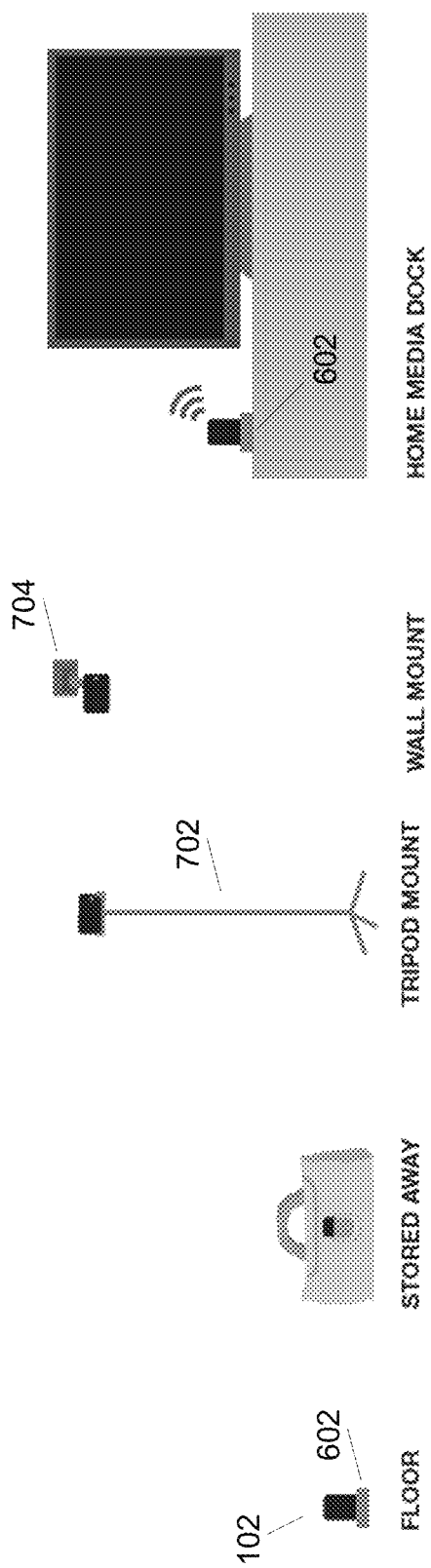

FIGS. 6-7 illustrates example various off-body configurations for the computer 102 in accordance with example embodiments. Computer 102 may be placed in a docking station 602 to permit display of the GUI on a larger screen and output of audio through a stereo system. As in other examples, computer 102 may respond to voice commands, via direct user input (e.g., using a keyboard), via input from a remote control, or other manners to receive user commands. Other off-body configurations may include placing the computer 102 on a floor or table nearby where a user is exercising, storing the computer 102 in a workout bag or other storage container, placing the computer 102 on a tripod mount 702, and placing the computer 102 on a wall mount 704. Other off-body configurations may also be used. When worn off-body, a user may wear head-phone, ear buds, a wrist-worn device, etc. that may provide the user with real-time updates. The pod sensor 304 and/or the distributed sensor 306 may wirelessly communicate with the computer 102 at the off-body locations when in range, at periodic time intervals, when triggered by the user, and/or may store data and upload the data to the computer 102 when in range or when instructed by the user at a later time.

Figure 8:
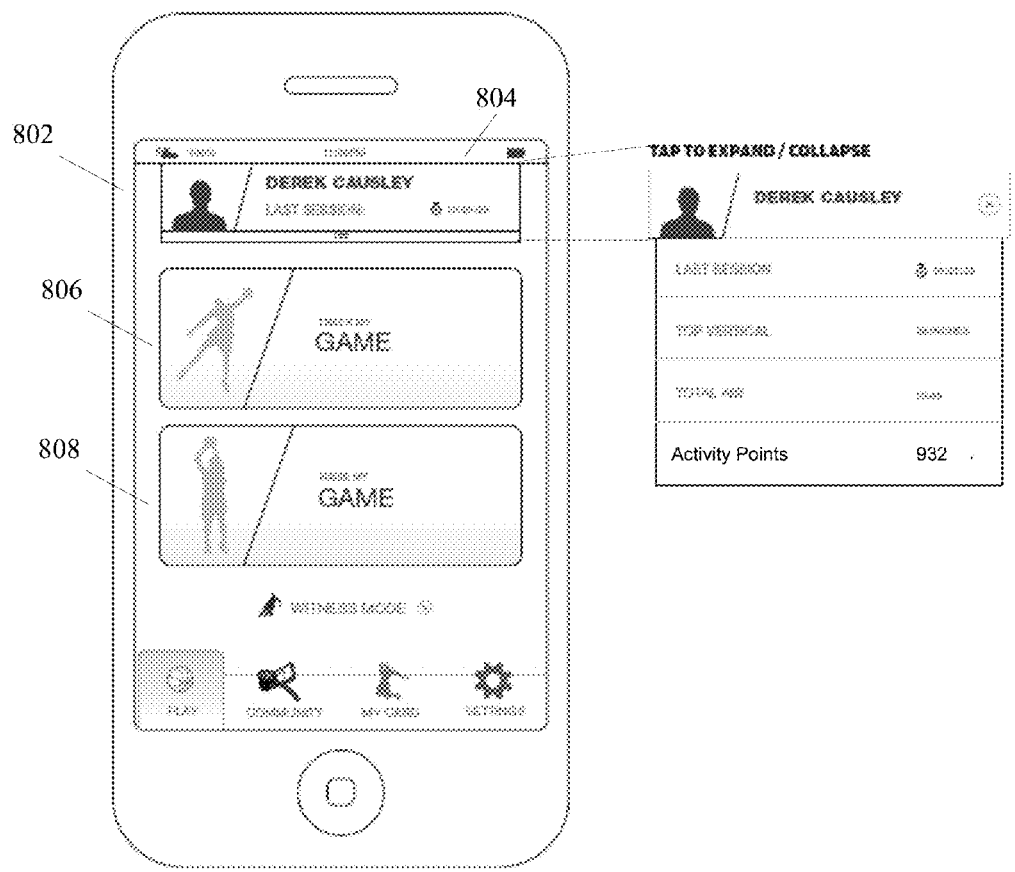
FIG. 8 illustrates an example display of a graphical user interface (GUI) presented by a display screen of a computer in accordance with example embodiments.

In an example, the user may interact with a graphical user interface (GUI) of the computer 102. FIG. 8 illustrates an example display of a GUI presented by a display screen of the computer 102 in accordance with example embodiments. Home page display 802 of the GUI may present a home page to provide the user with general information, to prompt the user to select what type of physical activity session the user is interested in performing, and to permit the user to retrieve information about previously completed sessions (e.g., basketball games, workouts, etc.). The display screen of the computer 102 may be touch sensitive and/or may receive user input through a keyboard or other input means. For instance, the user may tap a display screen or provide other input to cause the computer 102 to perform operations.

To obtain information about a previous session, the user may tap or otherwise select on a field 804 including the last session to cause the computer 102 to update the home page display 802 to display performance metrics (e.g., vertical leap, total air, activity points, etc.) from at least one previous session. For example, the selected field 804 may expand, as seen in FIG. 8, to display information about duration of the last session, the user's top vertical leap, a total amount of time a user was in the air during the last session, and incentive points (e.g., activity points) earned in the previous session. The computer 102 may determine performance metrics (e.g., speed, vertical leap, etc.) by processing data sensed by the sensors 304 and 306 or other sensing devices.

Home page display 802 may prompt a user to select whether they wish to have the computer 102 track one or more user performance metrics during a workout or athletic activity session (e.g., track my game) by selecting field 806 or assist the user in improving their athletic skills (e.g., raise my game) by selecting field 808. FIGS. 9-21 discuss the former and FIGS. 22-31 discuss the latter.

FIG. 9 illustrates example performance metrics for user selection in accordance with example embodiments. In an example, a user may be interested in monitoring their total play time, vertical leap, distance, and calories burned and/or other metrics, and may use the home page display 802 to select from the desired metrics shown in FIG. 9. The metrics may also vary based on type of athletic activity performed in a session. For example, home page display 802 may present certain default performance metric selections, depending on the activity of the session. The user may provide input to change the default performance metric selections.

Other performance metrics than the ones shown in FIG. 9 may include a total number of jumps, a number of vertical jumps above a certain height (e.g., above 3 inches), a number of sprints (e.g., speed above a certain rate, either user selected or specified by computer 102), a number of fakes (e.g., quick changes in direction), a jump recovery (e.g., a fastest time between two jumps), a work rate (e.g., may be a function of average power multiplied by time length of workout session), a work rate level (e.g., low, medium, high), total steps, steps per unit time (e.g., per minute), number of bursts (e.g., number of times a user exceeds a speed threshold), balance, weight distribution (e.g., compare weight measured by a FSR 206 in a user's left shoe to weight measured by a FSR 206 in a user's right shoe, as well as amount FRSs 206 in one shoe), average time duration of sessions, total session time, average number of repetitions per exercise, average number of points earned per session, total number of points, number of calories burned, or other performance metrics. Additional performance metrics may also be used.

In an example, computer 102 may prompt the use to indicate which metrics to monitor for each type of session (e.g., baseball, soccer, basketball, etc.) and store the identified metrics in a user profile. Computer 102 may also prompt the user for desired metrics at the beginning of each session. Further, computer 102 may track all of the performance metrics, but may only display the selected metrics to the user in the GUI. For example, computer 102 may only monitor certain base metrics (e.g., based on battery life may be extended, to vary responsiveness, to avoid data overload, etc.). If the user desires to review metrics other than the ones currently displayed by the GUI, the user may input the desired metrics and the computer 102 may update the GUI accordingly. The metrics being displayed may be changed at any time. The default metrics may be presented once the session resumes or another session begins.

If computer 102 monitors more metrics than can be displayed, computer 102 may later go into a lower level of monitoring (e.g., as resources are consumed together with warnings to user), down to and through base and ultimately to one or no metrics being monitored. In an example, computer 102 may only display base metrics for a user, unless/until configured otherwise by user. Based on resources, computer 102 may reduce what is being displayed to only present the base performance metrics or fewer metrics. Sensors may continue to monitor the other performance metrics, and data from these sensors may be later available (e.g., via web experience, etc.).

Prior to beginning a session, sensors (e.g., sensors 304 and 306) are paired with computer 102. If the sensors still have data from activities that took place while the sensors were paired with another computer, the user may be prompted to delete the data before pairing is completed. During the pairing process computer 102 may try to identify one sensor in a right shoe and one sensor in a left shoe. Each shoe may include a memory device that provides left or right information to the sensor. The user may be provided error messages when multiple left or right shoes are found, multiple pairs of sensors are in range or when no sensors are in range. The paring process may be performed once per session. For example, computer 102 may execute various applications or modes without repairing sensors. If computer 102 becomes out of range of one or more sensors, the user may be alerted when the devices are back in range and data may be transmitted from the sensors to computer device 102.

Figure 10:
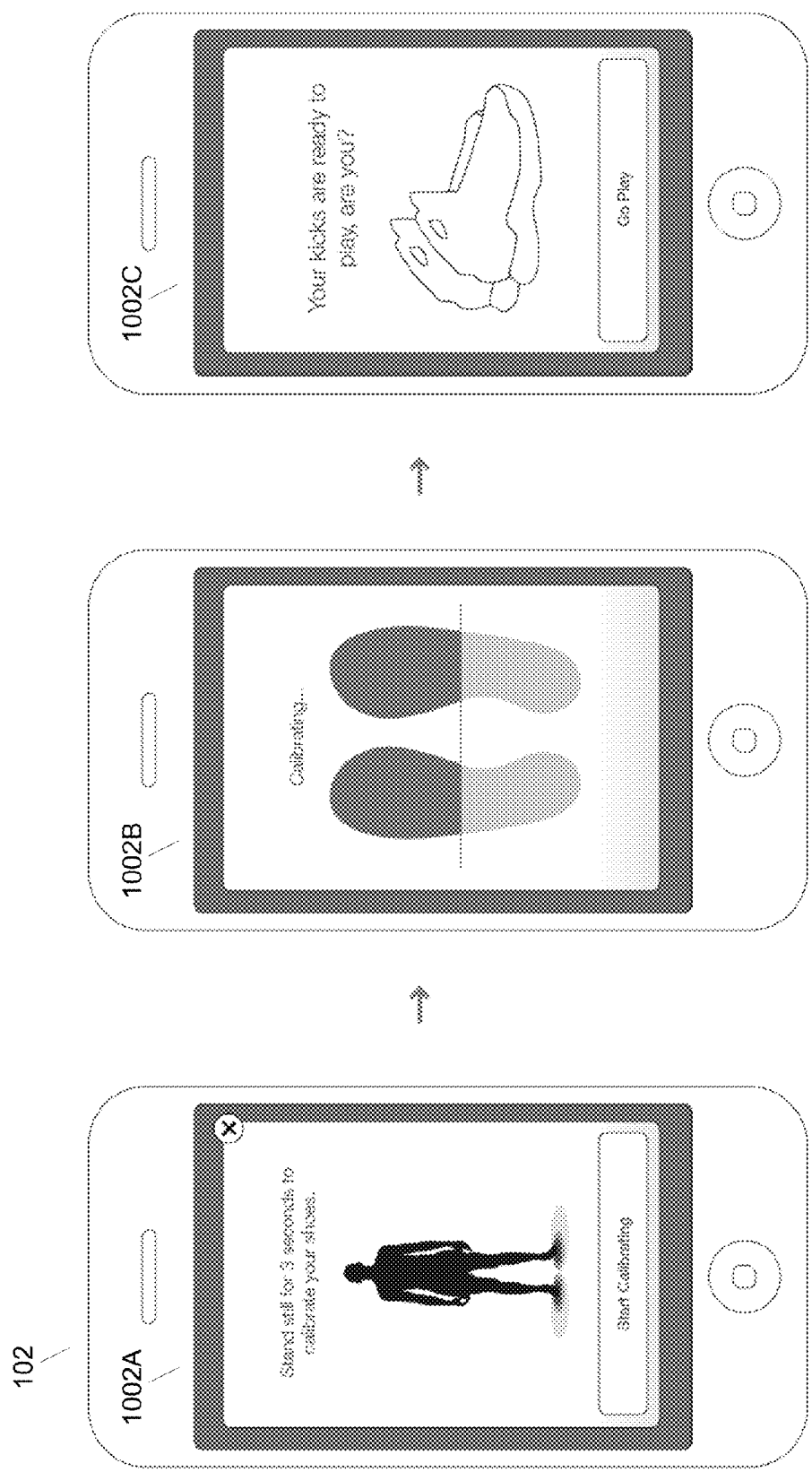

At the beginning of a session, computer 102 may calibrate the sensors of the shoes. FIGS. 10-11 illustrate an example of calibrating sensors in accordance with example embodiments. Calibration may involve computer 102 confirming ability to communicate directly or indirectly with the sensors (e.g., sensors 304 and 306), that the sensors are functioning properly, that the sensors have adequate battery life, and to establish baseline data. For example, computer 102 may communicate with (e.g., send a wireless signal) pod sensor 304 and distributed sensor 306 contained with a user's shoes. The pod sensor and the distributed sensor may reply with the requested data. Calibration may also occur at other time instances (e.g., mid-session, at the end of a session, etc.).

Figure 11D:
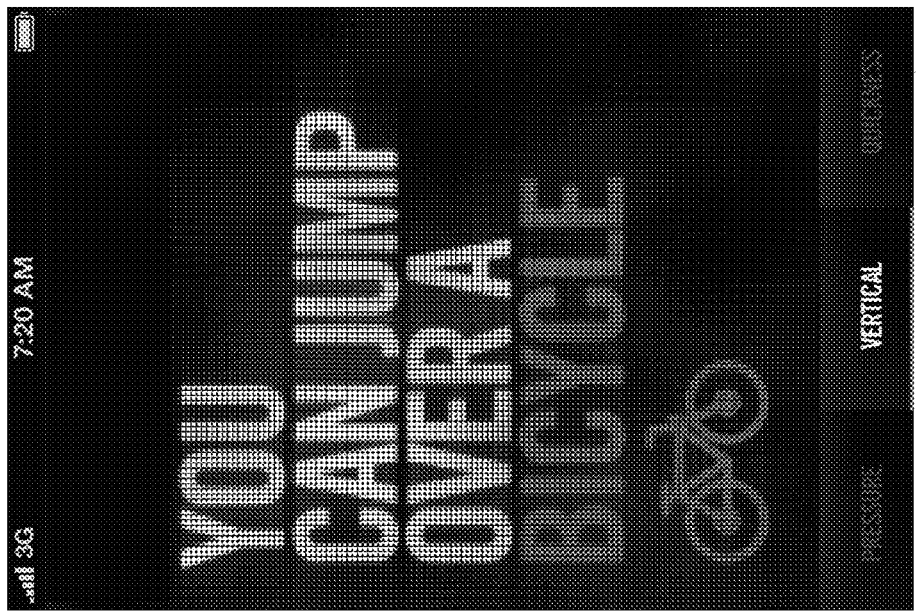
FIG. 11D shows an example GUI showing how high a user can jump in accordance with an embodiment of the invention.
Figure 11C:
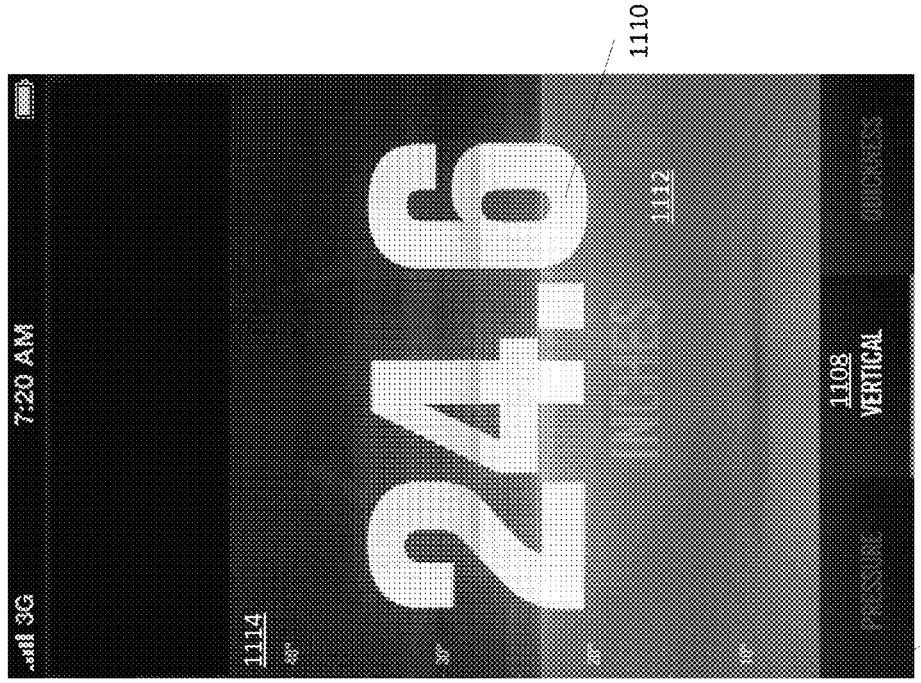
FIG. 11C shows an example GUI showing vertical height in accordance with an embodiment of the invention.

During calibration, the GUI may prompt the user to stand still to take baseline data measurements with pod sensor 304 and distributed sensor 306 (e.g., acceleration, weight distribution, total weight, etc.), as seen in displays 1002A-B. Calibration may also prompt the user to individually lift their feet to permit computer 102 to determine which foot is associated with which sensor data. Distributed sensor 306 may also be encoded with footwear information, such as, for example, shoe type, color, size, which foot (e.g., left or right), etc., that the computer 102 obtains during calibration. The computer 102 (or server 134) may process the reply from the sensors 304 and 306, and update the GUI to inform the user of any issues and how to address those issues (e.g., change battery, etc.) or if the calibration was successful, as seen in display 1002C. In FIG. 11A, for instance, field 1104 shown to the left of display 1102A includes example displays of battery life as well as connectivity status (e.g., connected, not connected). Calibration may also occur at certain events, such as detecting removal of a pod 304. Based on the calibration, the display 1102B (shown in FIG. 11B) presents a weight distribution for the user and a gauge 1106 representing remaining battery life. Either as part of calibrating one or more sensors and/or as a separate feature or function, a GUI may be configured to display performance data in substantially real-time (e.g., as fast as may be permitted to capture (and/or process) and transmit the data for display). FIG. 11C shows example GUIs that may be implemented in accordance with one embodiment. As seen in FIG. 11C, display 1102C may provide one or more selectable activity parameters for displaying captured values relating to that selectable parameter. For example, a user desiring to view values relating to their vertical height during a jump may select the "vertical" icon (see icon 1108); yet other icons may include, but are not limited to: quickness (which may display values relating to steps per second and/or distance per second), pressure, and/or any other detectable parameter. In other embodiments, a plurality of different parameters may be selected for simultaneous display. Yet in further embodiments, the parameters are not required to be selected. Default parameters may be displayed absent a user input. Data relating to the parameter(s) may be provided on display 1102C in real-time. For example, output 1110 indicates that the user has jumped "24.6 INCHES". Values may be provided graphically, such as for example represented by graph 1112 indicating the value is 24.6 inches. In certain embodiments, outputting of values, such as through outputs 1110 and/or 1112, may show the real-time data, in yet other embodiments, at least one of the outputs 1110/1112 may show other values, such as historical values, desired goal values, and/or a maximum or minimum value. For example, graph 1112 may fluctuate depending on the user's current (e.g., real-time) height; however, output 1110 may display the user's highest recorded jump during that session or an all-time best. Outputting of values or results may be correlated to physical objects and/or actions. For example, upon a user jumping a vertical height within a first range, such as between 24 inches to 30 inches, they may receive an indication that they could jump over a bicycle (see, e.g., display 1102D of FIG. 11D). As another example, values relating to a user's quantity of steps per second may be correlated to those of actual animals and displayed. Those skilled in the art will appreciate that other physical objects may be utilized in accordance with different embodiments.

Figure 12:
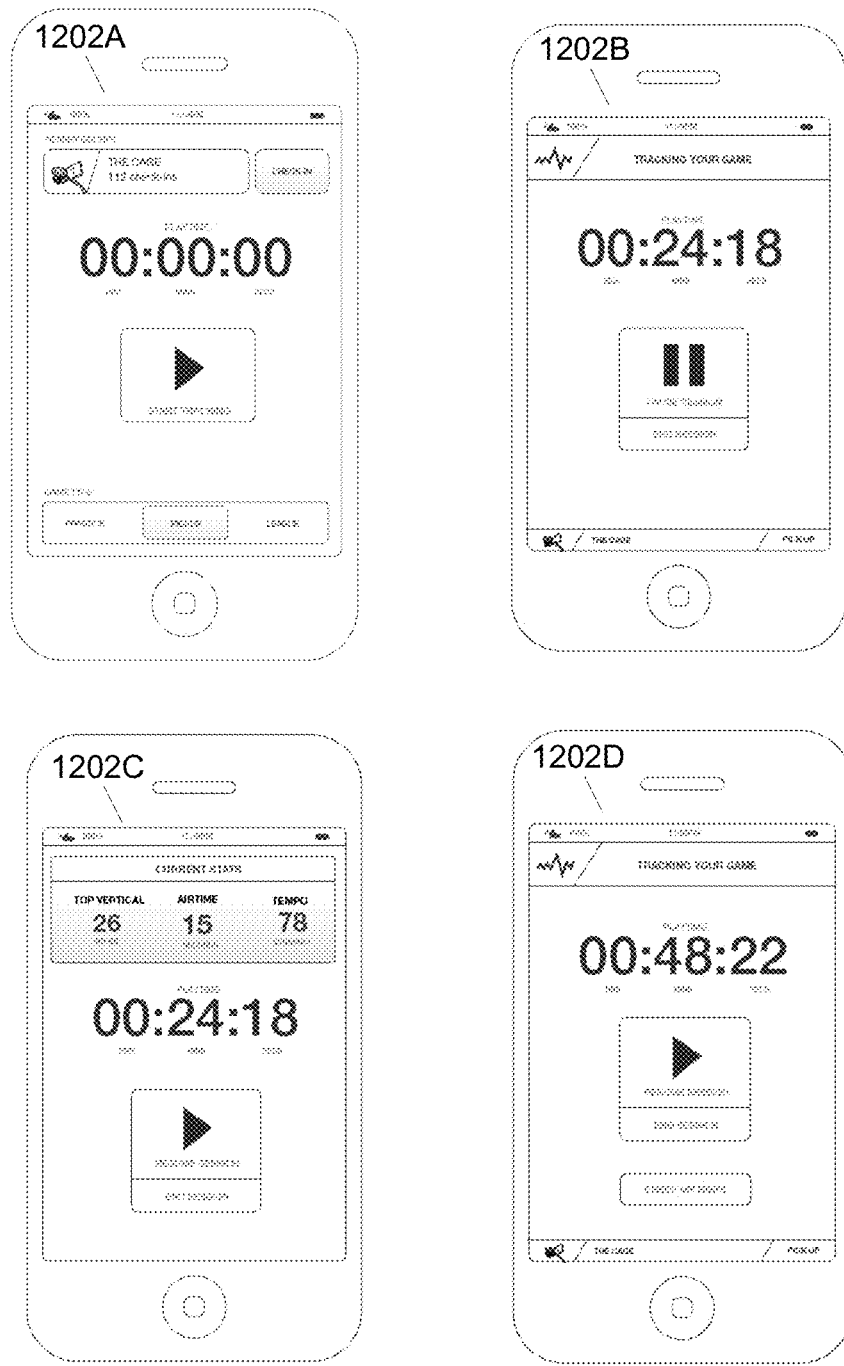
FIG. 12 illustrates example displays of a GUI presenting information relative to a session in accordance with example embodiments.

Computer 102 may prompt the user to start a session. FIG. 12 illustrates example displays of the GUI presenting information relative to a session in accordance with example embodiments. Display 1202A may initially prompt the user to check in to a court and to start a session. The user may also input a type of the session (e.g., practice, pickup game, league, half-court game, full court game, 3 on 3, 5 on 5, etc.). Display 1202B may inform the user of a duration of the session as well as prompting the user to pause and/or end their session. Display 1202C may present current performance metrics of the user (e.g., top vertical, air time, tempo, etc.). For viewing purposes, display 1202 may present default or user-selected statistics, but a swipe or other gesture may trigger a scroll, sequencing groups of predetermined number of performance metrics (e.g., 3 or other number, based on the performance metrics that can be shown on the screen in portrait versus landscape orientation) or otherwise brings up other performance metrics.

Computer 102 may also update display 1202 when a particular event is identified. For example, if a new record (e.g., personal best) is identified (e.g., new vertical max leap), computer 1202 may at least one of update the display (e.g., color, information presented, etc.), vibrate, sound a noise indicative of the specific record (e.g., based on color change placement on shoe corresponding to a specific metric), or prompt the user that some record (e.g., any metric) has been reached. Display 1202 may also present a button for the user to select signifying that a record has been achieved. Display 1202B may prompt the user to check their performance metrics (e.g., check my stats), as further described in FIG. 13.

Figure 13:
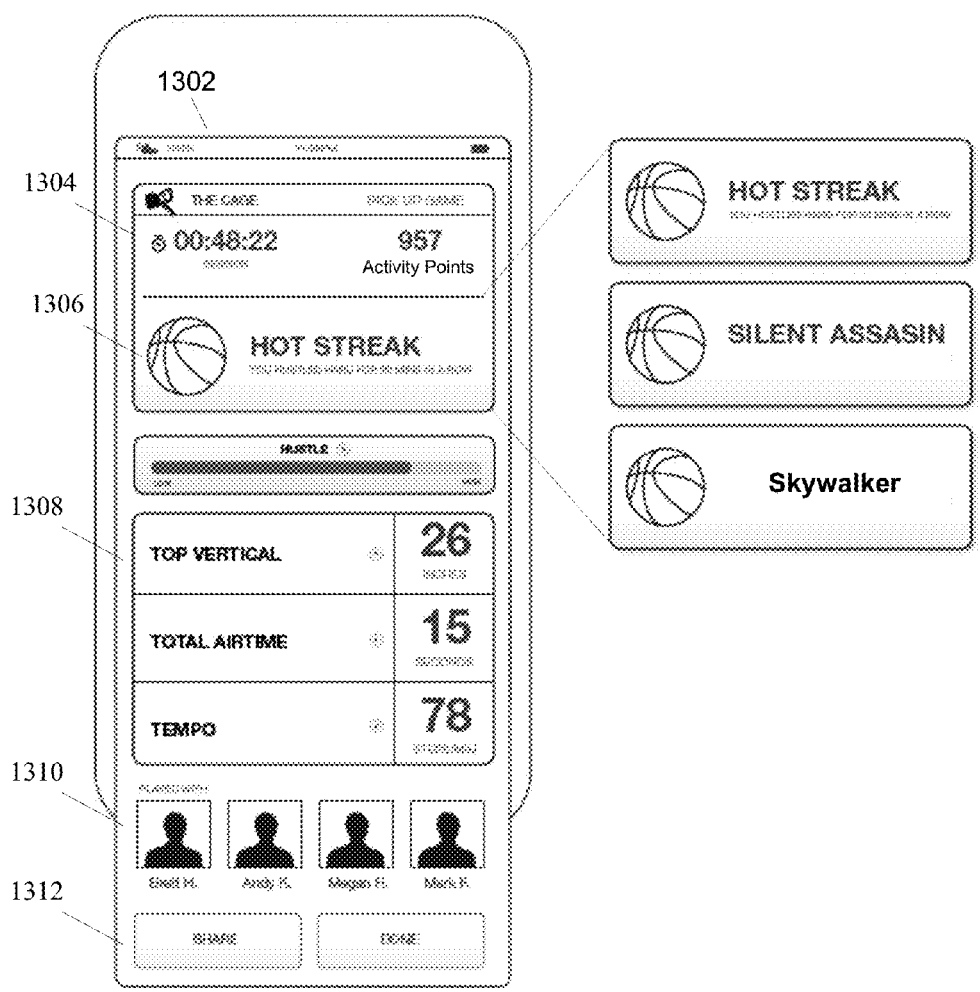
FIG. 13 illustrates an example display of a GUI providing a user with information about their performance metrics during a session in accordance with example embodiments.

FIG. 13 illustrates an example display of a GUI providing a user with information about their performance metrics during a session in accordance with example embodiments. Display 1302 may present information about a length of a current or previous session in field 1304, various performance metrics (e.g., top vertical, total airtime, tempo, etc.) for the user in field 1308, as well as who the user played with during the session in field 1310. For example, computer 102, sensor 304 or 306, or other device associated with a first user may exchange a first user identifier with a computer 102, sensor 304 or 306, or other device associated with a second user to that each computer may be aware of who participated in a session.

The computer 102 may also process the performance metrics to assign a playing style to the user as indicated in field 1306. Field 1306 may indicate that the user is a "hot streak" in response to determining that the user hustled hard for thirty minutes in a row. The box to the right of field 1306 may indicate alternative playing styles. The computer 102 may identify other types of playing styles. For example, the computer 102 may assign a 'silent assassin' playing style when identifying periods of inactivity followed by explosive bursts, a 'vortex' playing style when a user exhibits little movement or jumping during the session, a 'cobra' playing style when a user exhibits perpetual easy movement with huge bursts and jumps, a 'track star' playing style when a user is fast, has good stamina, and has a high peak speed, and a 'skywalker' playing style when a user has a big vertical leap and a long hang time. In some examples, more than one style may be assigned to the user, with a different style associated with one individual session as compared with another session. Plural styles may be assigned and displayed for a single session.

The computer 102 may assign a particular playing style based on receiving user data from at least one of pod sensor 304 (e.g., accelerometer data), distributed sensor 306 (e.g., force data), or other sensors. The computer 102 may compare the user data with playing style data for a plurality of different playing styles to determine which of the playing styles most closely matches the data. For example, the computer 102 may set performance metric thresholds for each of the playing styles. Some playing styles may require that, at least once during the session, the user jumped a certain height, ran at a certain speed, played for a certain amount of time, and/or performed other tasks. Other playing styles may require that the user data indicate that the user performed certain sequences of events (e.g., little movement followed by quick acceleration to at least a certain top speed). Some playing styles may require that the user data indicate that the user maintained thresholds for a certain amount of time (e.g., maintained average speed over a threshold throughout a game).

In an example, a playing style may be assigned based on a data set obtained from a set of sensors including sensors worn at various locations on a user's body (e.g., accelerometers at the gluteus and or upper body to identify a "BANGER" playing style). Also, other, non-activity data may come into determining a playing style, such as user profile data (e.g., user age, height, gender, etc.). For example, some playing styles may be gender specific or based on ambient conditions (e.g., a "POSTMAN" style because use plays in rain, sleet, snow, etc.).

A user or user group may define their own playing styles, based on a combination of metrics and analytics. The users or user groups may change a name of the playing style, without changing the associated metrics and analytics. Playing styles may be updated automatically. For example, personal training system 100 may periodically update a playing style specified by system 100. In another example, system 100 may automatically update a playing style when the name of the playing style is associated with a particular location (e.g., state, city, court), and that playing style is referred to by a different name at another location (e.g., keep the designation consistent with local lingo).

In FIG. 13, display 1302 permits the user to share their performance metrics with other users and/or to post to a social networking website by selecting field 1312. The user may also input a message (e.g., "check out my vertical leap") to accompany the performance metrics being sent. The computer 102 may distribute performance metric data of a current and/or previous session and the message to the server 134 in response to a user request to share. The server 134 may incorporate the data and/or message in the social networking website and/or may distribute the data/message to other desired or all users.

Figure 14:
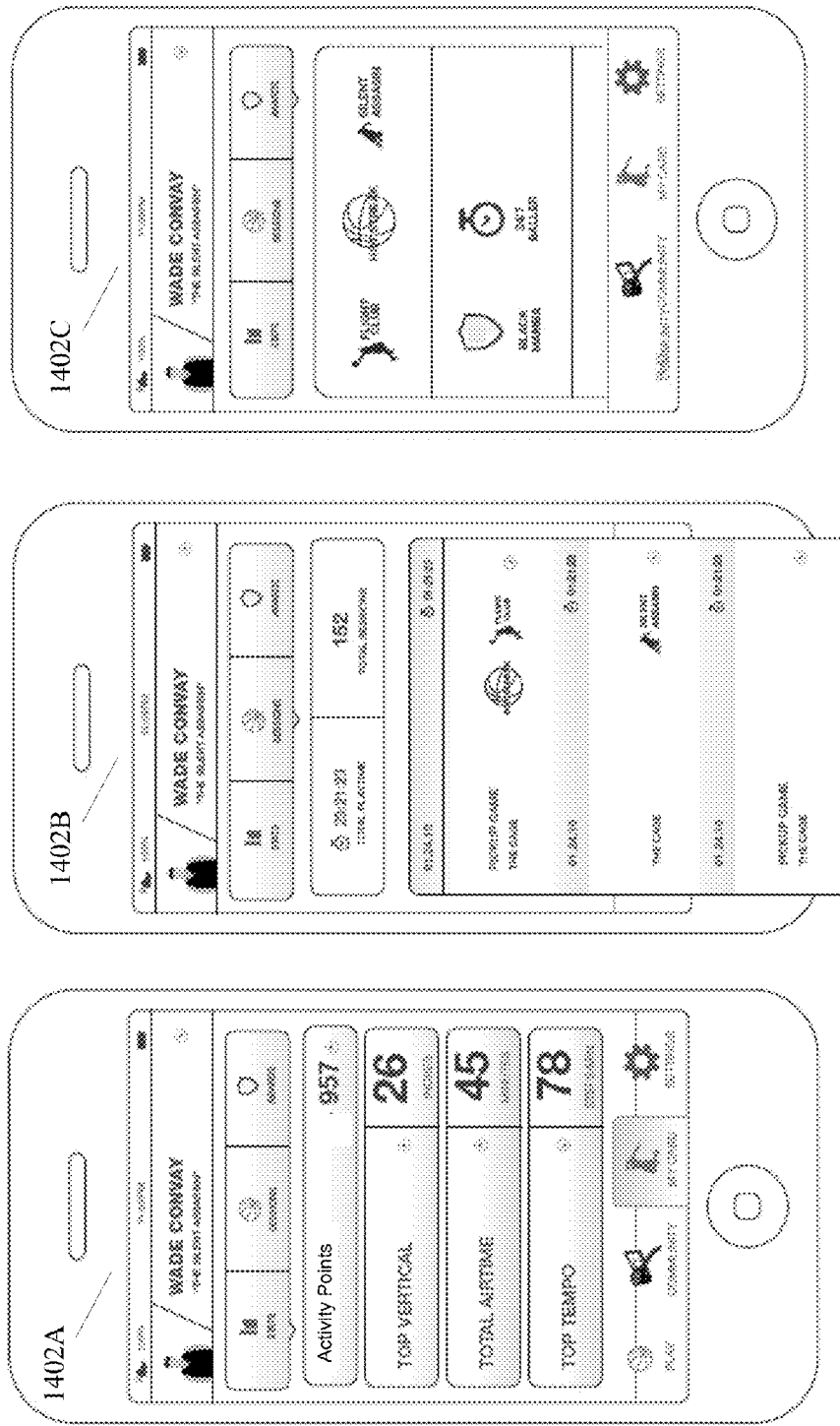
FIG. 14 illustrates example displays of a GUI presenting information about a user's virtual card (vcard) in accordance with example embodiments.

FIG. 14 illustrates example displays of the GUI presenting information about a user's virtual card (vcard) in accordance with example embodiments. The vcard may include information about a user's athletic history. The vcard may include data on a user's performance metrics, sessions, and awards at individual sessions as well as averages of the performance metrics. The vcard statistics display 1402A may indicate a number of points a user has acquired (e.g., activity points or metrics), as well as running totals and/or top performances by the user. The activity points may a statistic indicating physical activity performed by a user. The server 134 and/or computer 102 may award activity points to the user upon achieving certain athletic milestones. The vcard sessions display 1402B may indicate a total amount of playtime and number of sessions a user has completed, as well as providing historical information about completed sessions. The vcard sessions display 1402B may also indicate a playing style the user exhibited for each session as well as a session length and date of the session. The vcard awards display 1402C may indicate awards the user has accrued over time. For example, the server 134 and/or computer 102 may award the user a flight club award after accruing a total amount of loft time during the sessions.

Other example awards may be a "king of the court" award for a user who has one or more top metrics at a specific court, a "flier mile" award earned with one mile of flight time (or for other quanta of time and distance), a "worldwide wes" award when a player participates in sessions in multiple countries, an "ankle-breaker" award to those having at least a certain top speed or quickest first step, a "jump king" award for a user having at least a certain vertical leap, a "24/7 bailer" award for a user who plays a certain number of days in a row or at a certain number of different courts, an "ice man" award if a certain number of rivals follow a user, a "black mamba" award if an even greater number of rivals follow a user (compared to an ice-man), a "prodigy" award for a young player achieving certain performance metric levels, and an "old school" award for older players achieving certain performance metric levels. Other types of awards may also be awarded. Performance and/or profile information may be used by server 134 and/or computer 102 to suggest courts or other locations to users. For example, server 134 may review a user's performance and/or profile information and recommend a court that currently has other users with similar performance and/or profile information.

Figure 15:
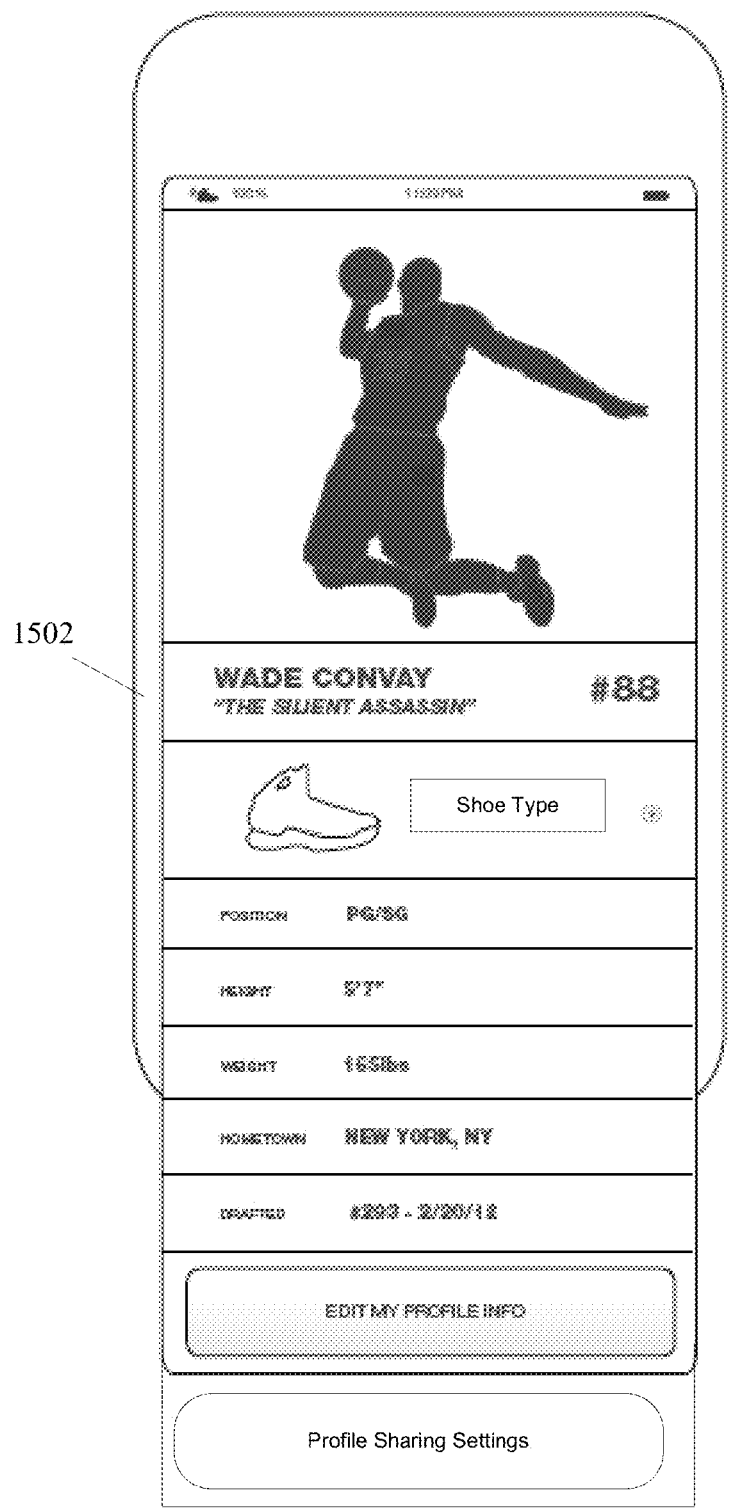
FIG. 15 illustrates an example user profile display of a GUI presenting a user profile in accordance with example embodiments.
Figure 16:
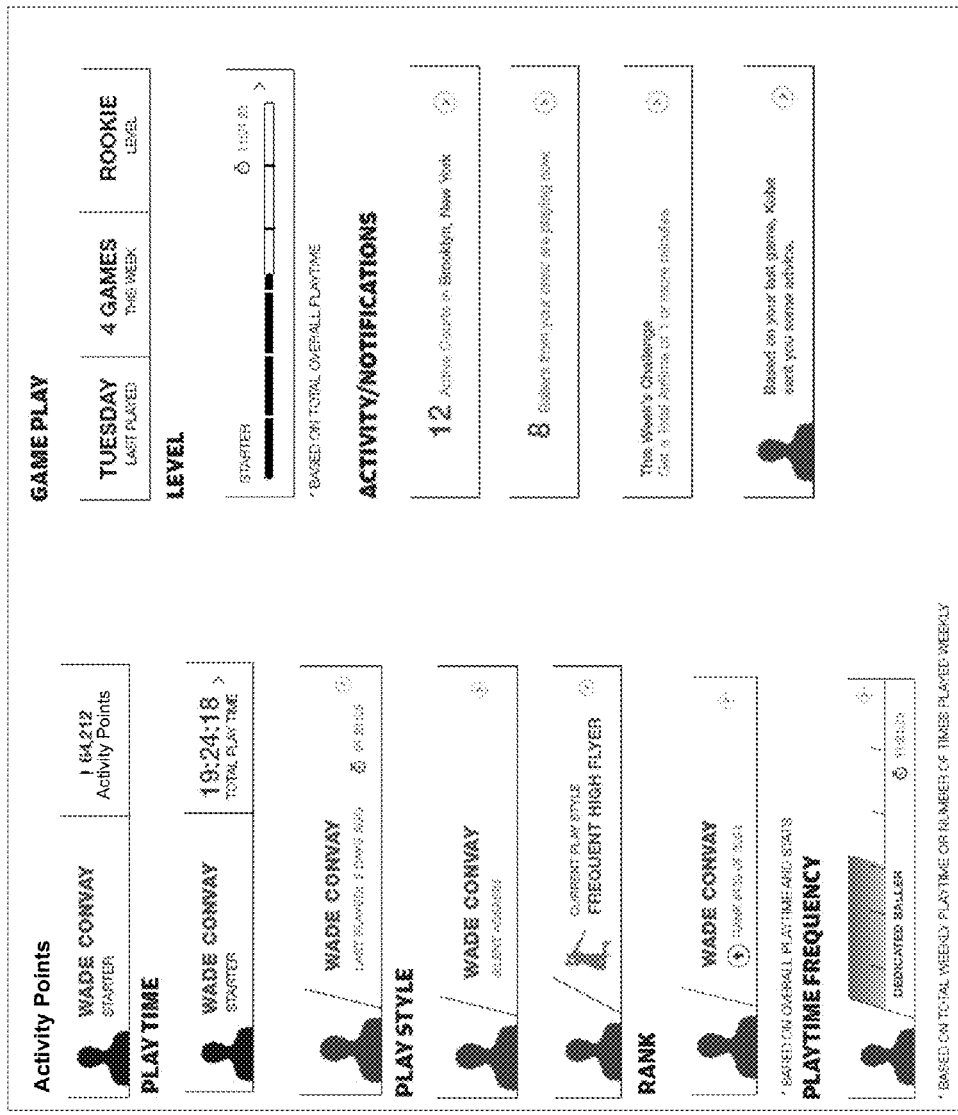
FIG. 16 illustrates a further example of user profile display presenting additional information about the user in accordance with example embodiments.

FIG. 15 illustrates an example user profile display of the GUI presenting a user profile in accordance with example embodiments. The user profile display 1502 may present information about the user, such as height, weight, and position, playing style (e.g., "The Silent Assassin"), as well as other information. The user profile display 1502 may also indicate one or more types of shoe worn by the user. The user profile display 1502 may present information about the user's activity, and may permit the user to control sharing this information with other users. For example, the user may specify which other users can view user profile information, or may make all of the user's information accessible to any other user. FIG. 16 illustrates further examples of information about the user that may be presented in user profile display 1502 in accordance with example embodiments.

Figure 17:
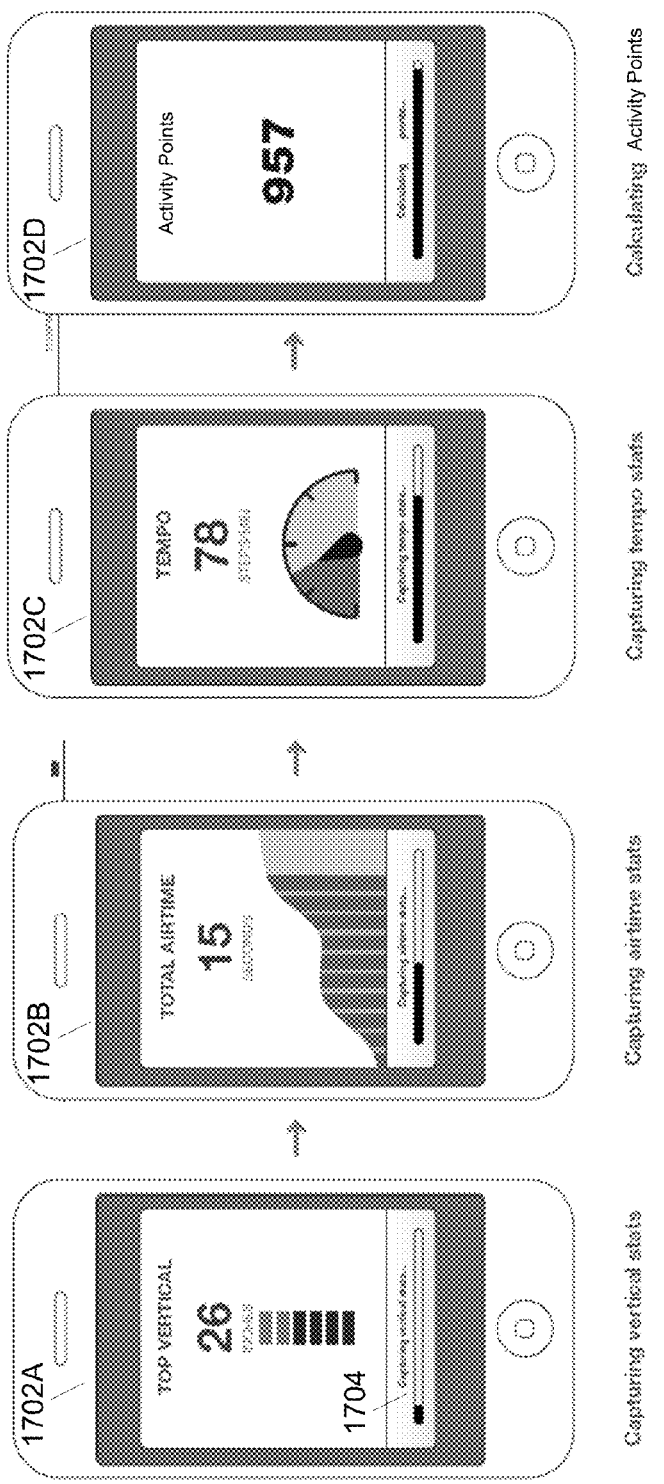
FIGS. 17-20 illustrate further example displays of a GUI for displaying performance metrics to a user in accordance with example embodiments.

FIGS. 17-20 illustrate further example displays of a GUI for displaying performance metrics to a user in accordance with example embodiments. During, at the end of a session, or both, the computer 102 may communicate with at least one of pod sensor 304, distributed sensor 306, or other sensor, to obtain data to generate the performance metrics. Example displays of the GUI while capturing data are shown in FIG. 17, such as top vertical in display 1702A, total airtime in display 1702B, tempo statistics in display 1702C, and points in display 1702D. Scroll bar 1704 represents the progress in transferring data from the sensors to computer 102.

Figure 18A:
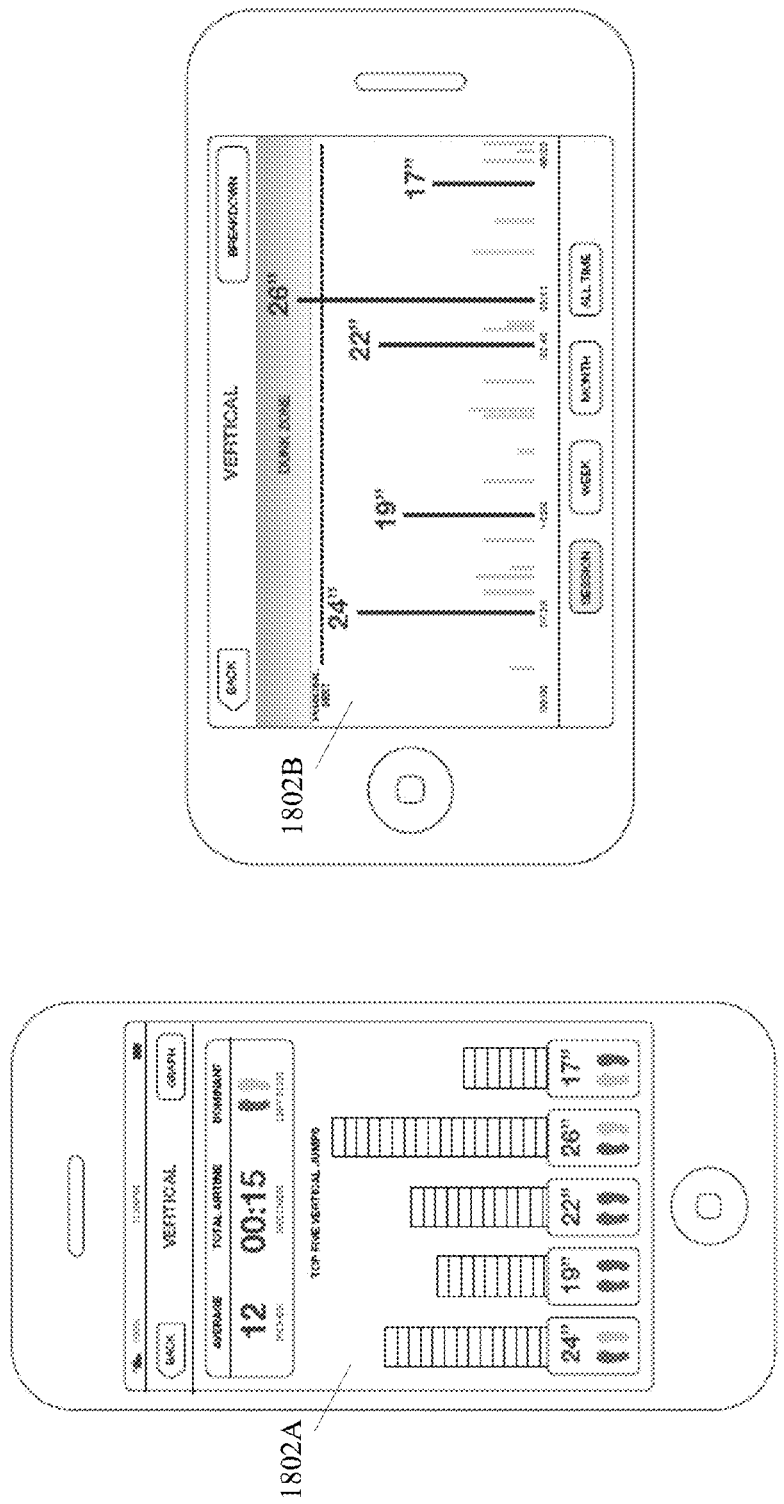

FIG. 18A illustrates example leap displays relating to a user's vertical leap in accordance with example embodiments. The computer 102 may track information on the user's vertical leap during an exercise session as well as at what times during the session the leaps occurred. The computer 102 may determine a user's vertical leap based on an amount of loft time between when both feet of a user leave the ground and when a first of the user's feet next contacts the ground. The computer 102 may process accelerometer data from pod sensor 304 and/or force data from distributed sensor 306 to determine a moment when both of the user's feet are off the ground and when a first of the feet next contacts the ground. The computer 102 may also compare user data from pod sensor 304 and distributed sensor 306 with jump data to confirm that the user actually jumped and landed, rather than merely lifted their feet off of the ground or hung on a basketball rim (or other object) for a predetermined time. The jump data may be data generated to indicate what a force profile and/or acceleration profile should look like for someone who actually jumped. The computer 102 may use a similarity metric when comparing the user data to the jump data. If the user data is not sufficiently similar to the jump data, the computer 102 may determine that the user data is not a jump and may not include the user data when determining a user's performance metrics (e.g., top or average vertical leap).

Provided that the computer 102 determines that the user data is for a jump, the computer 102 may process the user data to determine a vertical leap, a time of the vertical leap, a user's average vertical leap height, maintain a running total of loft time for jumps, and/or determine which foot is dominant, as well as other metrics. The computer 102 may identify a dominant foot based on the force data and/or accelerometer data associated with each shoe. The force data and/or accelerometer data may include timing information so that the computer 102 can compare events in each shoe. The computer 102 may process the force data and/or accelerometer data as well as the timing information to determine which foot was last on the ground prior to a jump. The computer 102 may identify a dominant foot based on the one that is last on the ground when a user jumps and/or the one associated with a user's largest vertical leap. The computer 102 may also present leap display 1802A including a user's top five vertical leaps and depict which foot, or both feet, was last on the ground immediately preceding the jump. Leap display 1802A may display any desired number of top leaps, which may be specified by the user or set by system 100. The number of top leaps may be based on an amount of time. For example, leap display 1802A may present the top five leaps over the full time of a session, top five in the most recent predetermined number of minutes or percentage of total session time, or based on the type of session (e.g., pick-up basketball game as compared to an organized game). The leap display 1802A or 1802B may also display vertical leaps over durations other than by session, and may include, for example, month, week, all time, or other time ranges. Leap display 1802A or 1802B may also present a total number of jumps, a cumulative amount of hang time, an average hang time, hang time corresponding to a highest vertical leap, or other information relating to jumping. Orientation of computer 102 may control which of leap display 1802A and leap display 1802B is currently being presented. For example, a user may rotate computer 102 (e.g., 90 degrees) to change from presenting leap display 1802A (e.g., a portrait orientation) to presenting leap display 1802B (e.g., a landscape orientation). A user may rotate computer 102 in the opposite direction to change from presenting leap display 1802B to presenting leap display 1802A. Similarly, rotation of computer 102 may be used to alternate between displays in other examples described herein.

In another example, leap display 1802B may display a user's jumps chronologically over a session and may indicate a time when each jump occurred as well as vertical height for each jump during the session. The leap display 1802B may also display a user's personal best vertical leap from a previous session or previously set during the session. In an example, a personal best line can be changed during a session, either via a step function, or by adding a new line of the new best to supplement the existing line (e.g., "new best" color) and showing lines for the session in which the new best occurs. Computer 102 may also update leap display 1802B by replacing the previous personal best line (e.g., in one color) with a new line (e.g., in a new personal best color, which may only be used during the session in which the personal best occurred). Further, the color may change as the user's personal best improves to indicate ability compared to other users (e.g., you jumped higher than 85% of other users).

The leap display 1802B may include a performance zone (e.g., dunk zone) indicating when a user may be able to perform an act (e.g., dunk a basketball). The computer 102 may tailor the performance zone to the user based on the user's physical attributes (e.g., height, arm length, leg length, torso length, body length, etc.). For example, a dunk zone may require a higher vertical leap for a shorter user than a taller user. The dunk zone may appear as a gradient instead of a hard threshold. The use of a gradient may account for errors associated with measurements, analysis and predictions.

A performance zone may correspond to a range of values, a minimum value, or a maximum value. The one or more values may correlate to when a user's athletic performance is expected that a user could perform a particular act. For example, a performance zone may be a minimum vertical leap that would permit a user to dunk a basketball. The user need not actually perform the act (e.g., dunking), but instead the performance zone may indicate when the computer 102 calculates that the user could perform the act.

Based on sensor data obtained from one or more sessions, computer 102 may provide a recommendation to help the user achieve the performance zone. For example, computer 102 analysis of sensor data associated with leaps by the user may enable more feedback to the user to enhance ability to get into the dunk zone or to improve personal bests in rare air. For instance, computer 102 may process sensor data and recommend that the user adjust certain body parts to increase the user's leaping ability. In another example, computer 102 may suggest that the user obtain greater acceleration of leading foot or more pressure on trailing foot by increasing upper body acceleration.

A performance zone may be established for any desired athletic movement. Example performance zones may correspond to a minimum amount of pressure measured by distributed sensor 306, a maximum amount of pressure, pressure falling within a particular range or pressures. Other example performance zones may correspond to a minimum amount of acceleration measured by the sensor 306, a maximum amount of pressure, pressure falling within a particular range or pressures. Also, a performance zone may be based on a combination of different measurements or a sequence of measurements. For example, a performance zone may specify at least a certain amount of acceleration, followed by at least a certain amount of loft time, followed by at least a certain amount of measured pressure.

In gymnastics, for example, acceleration and body rotation may be monitored. For instance, it may be desirable for a gymnast to have a specific amount of body rotation during a dismount from the uneven bars. If the gymnast rotates too quickly or slowly, he or she may not orient their body in a proper position when landing. The performance zone may be a "spin zone" specifying minimum and maximum rotational accelerations, and computer 102 may monitor for over and under rotation to provide the gymnast with feedback on whether they are within a performance zone during a dismount. Computer 102 may provide a recommendation to adjust certain body parts to adjust an amount of acceleration when dismounting to increase or decrease rotation by the user. A performance zone may be established for other sports (e.g., track and field, golf, etc.).

Computer 102 may tailor the performance zone based on feedback received form the user. In an example, computer 102 may receive input from a user indicating for which vertical leaps the user was able to perform the act (e.g., dunk a basketball), and the computer 102 may adjust a minimum required vertical leap for the user to be in the performance zone based on the user's feedback. Computer 102 may award one or more activity points to a user for being in the performance zone as well as for the amount of time the user maintained their performance within the performance zone. Computer 102 may also determine an amount of calories burned by the user while in the performance zone.

Figure 18B:
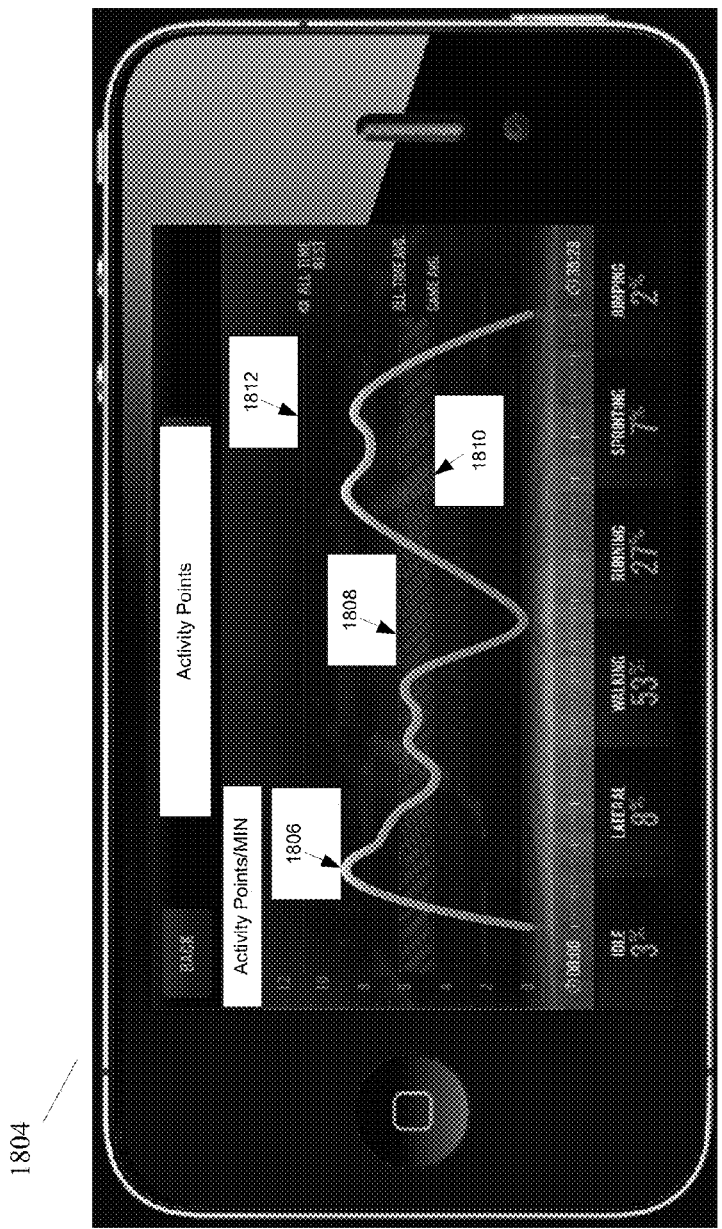

Computer 102 may present information indicating a rate of activity points earned by a user over the duration of an exercise session. FIG. 18B illustrates an example activity points display 1804 in accordance with example embodiments. Computer 102 may determine and award activity points to a user during the exercise session. To do so, computer 102 may compare measured user performance to any number of metrics to award activity points. For example, computer 102 may award a predetermined number of activity point for running a predetermined distance. As may be seen in FIG. 18B, line 1806 of activity points display 1804 may represent the rate at which a user earned activity points at various times during the exercise session, line 1806 may represent an all-time average rate at which a user has accrued activity points, line 1808 may represent the average rate at which the user accrued activity points during this particular session, and line 1812 may represent an all-time best rate for accruing activity points. In an example, line 1806 may represent how may activity points a user accrues per minute, or other interval of time (e.g., per millisecond, per second, per ten seconds, per thirty seconds, etc.). Activity points display 1804 may also present indicia, such as lines, indicating other matrices, such as averages, including but not limited to an average rate of accrued activity points for a predetermined number of previous session (e.g., last three sessions). Further, the lines may be of different colors. If a new all-time best is established, activity points display 1804 may flash or otherwise present an indication signifying the accomplishment.

Computer 102 may categorize activities performed by the user as well as a percentage of time during an exercise session a user was in a particular category, and present this information to the user in the activity points display 1804. For example, activity points display 1804 may indicate a percentage of time during a session that a user was idle, percentage of time that the user moved laterally, percentage of time that the user was walking, percentage of time that the user was running, percentage of time that the user was sprinting, and percentage of time that the user was jumping, etc. Other categories instead of or in addition to the ones shown in activity points display 1804 may also be presented. Further, activity points display 1804 may display a cumulative amount of time, rather than percentage of time, for each of these statistics. Computer 102 may determine that amount of activity points a user earned while in each category, as well as a total amount of activity points earned during an exercise session, and present such information via activity points display 1804. In an example, computer 102 may determine that a user earned 25 activity points while walking, 75 activity points while walking, and 150 activity points while sprinting, for a total of 250 activity points. Computer 102 may also determine a caloric burn rate for each of the categories instead of or in addition to determining activity points.

Figure 19:
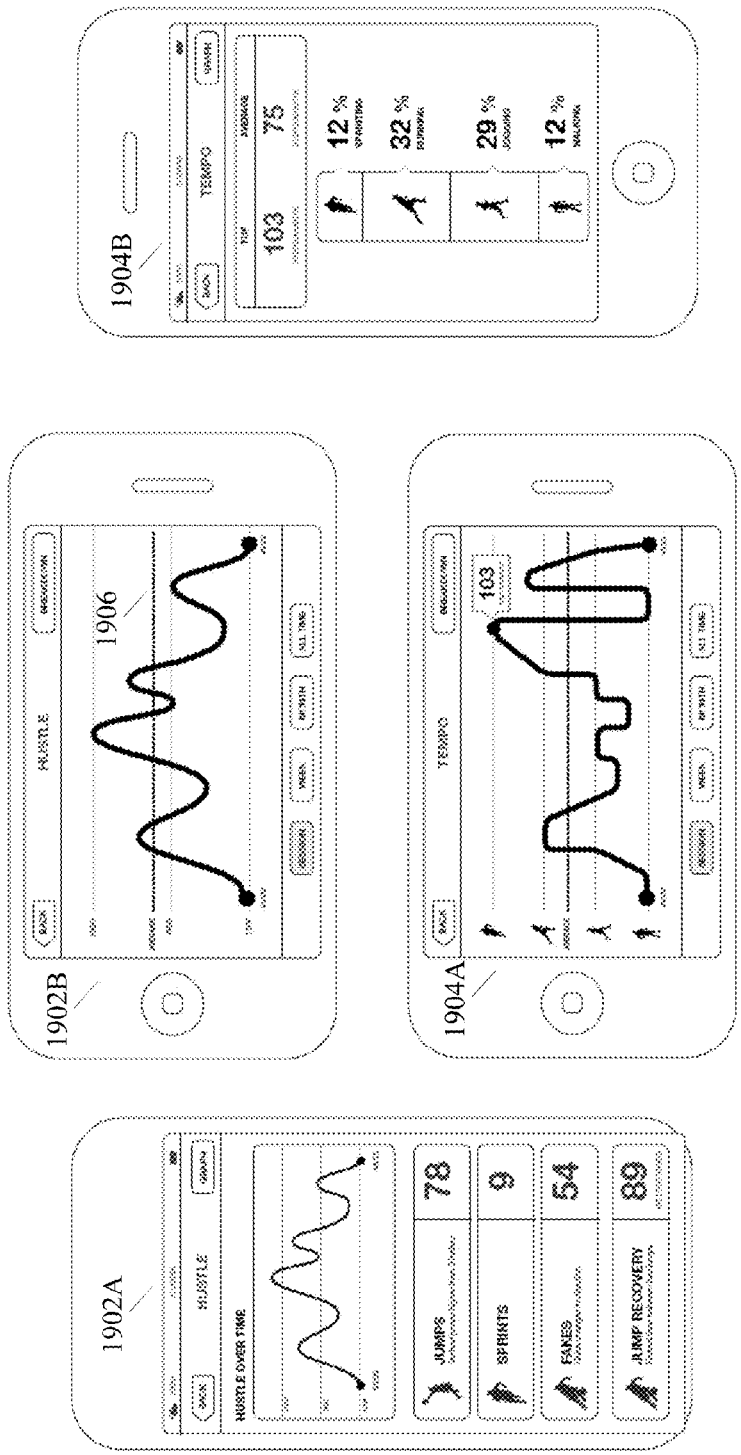

The computer 102 may also display performance metric data based on measurements of a user's hustle and tempo. FIG. 19 illustrates example hustle displays 1902A-B and tempo displays 1904A-B in accordance with example embodiments. Hustle display 1902A may present a user's hustle over time during a session, as well as other performance metrics. For example, computer 102 may track various performance metrics including a running total of jumps, sprints, fakes, and jump recovery (e.g., a shortest amount of time between consecutive jumps) during a session, and hustle may be a function of these metrics. With reference to hustle display 1902B, computer 102 may divide hustle into three categories: low, medium and high. More or fewer categories of hustle may be defined. Hustle display 1902B may also present line 1906 indicating an average hustle level over a session.

With reference to tempo display 1904A, computer 102 may present information on a user's tempo during a session. Tempo may be based on a rate of steps taken by a user per interval of time (e.g., steps per minute). The categories may be defined by ranges of step rates. For example, walking may be defined as one to 30 steps per minute, jogging may be 31-50 steps per minute, running may be defined as 51-70 steps per minute, and sprinting may be defined as 71 or more steps per minute. With reference to tempo display 1904B, computer 102 may indicate how often a user was in each category during a session. For example, tempo display 1904B may indicate what percentage of the time a user was in each category (e.g., 12% sprinting). Tempo display 1904 may also indicate a user's quickest number of steps per second (e.g., 4.1 steps/second) or any other time interval, a total number of steps, a total number of sprints, etc.

Figure 20A:
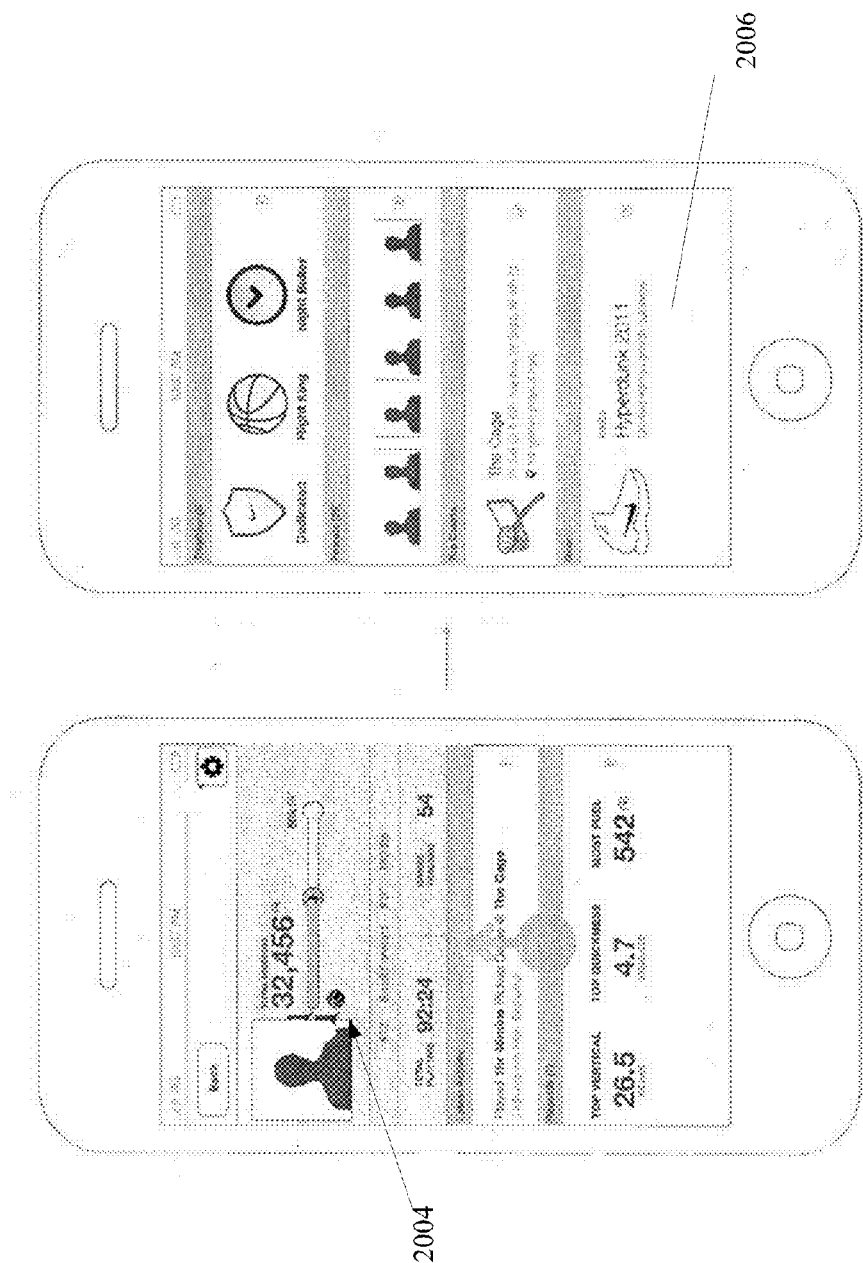

The computer 102 may also inform the user of activity points earned during the workout as well as total activity points accrued. FIG. 20 illustrates an example activity points display of a GUI informing a user of points earned during a session in accordance with example embodiments. The computer 102 may process data taken during a workout session to award points to a user. The points may track a user's activity across different sports and workout sessions. The points display 2002A-B may permit the user to determine points earned by date range, workout session, or other ranges. FIG. 20a illustrates example activity points displays that include icons identifying sports and a section that identifies equipment used to earn the points. Icon 2004 represents a basketball to identify the sport the user participated in to earn the activity points. Numerous other icons may be used to represent other sports. Section 2006 shows the products or equipment used by the user to earn activity points. In one embodiment, selecting a product or equipment may result in the display of other products or equipment used by the user to earn activity points. Server 134 may compare activity points earned by user different equipment so that the user can compare performance. For example, server 134 may compile activity points earned while playing basketball with different shoes. The information may be transmitted and displayed to the user so that the user can determine if he or she performs better with certain shoes. In some embodiments, server 134 is programmed to analyze performance and correlations of performance with equipment.

Figure 21:
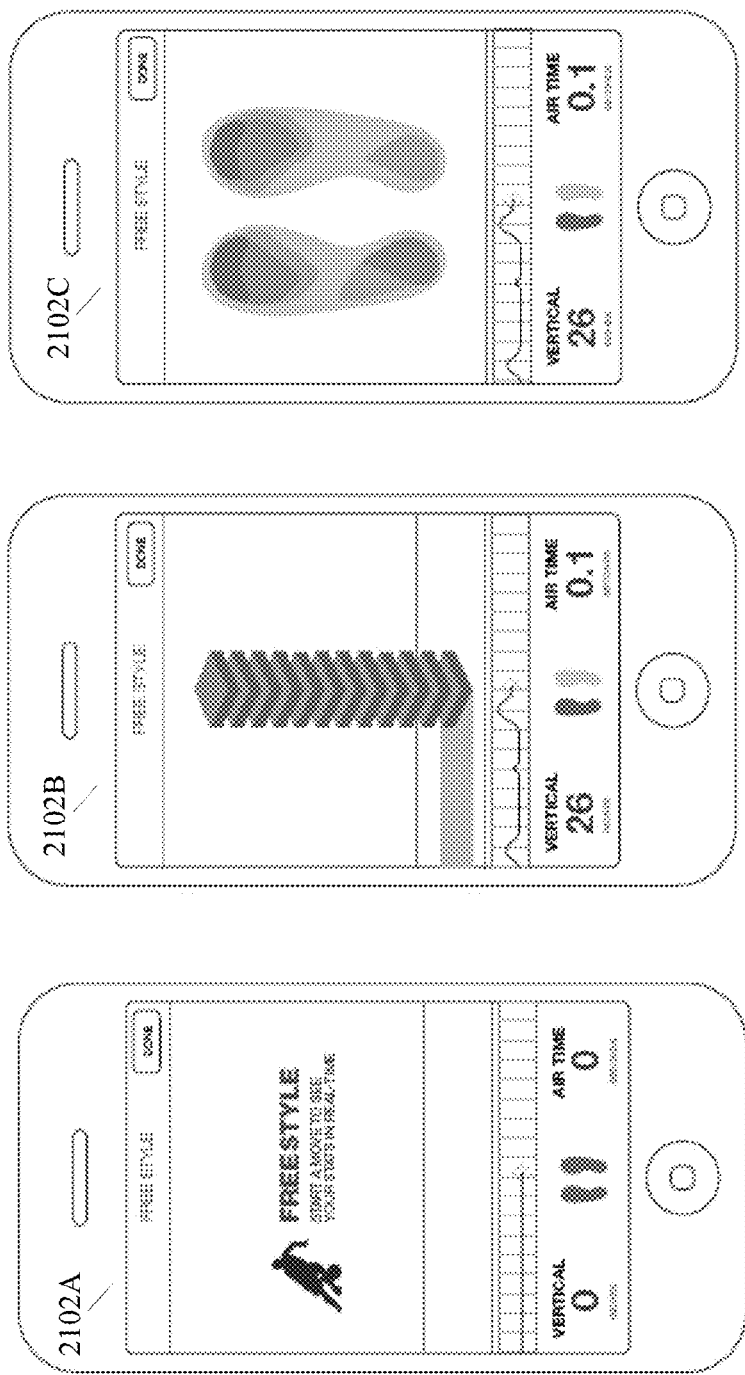
FIG. 21 illustrates example freestyle displays of a GUI providing information on freestyle user movement in accordance with example embodiments.

The computer 102 may also track user defined movement. FIG. 21 illustrates example freestyle displays of a GUI providing information on freestyle user movement in accordance with example embodiments. In freestyle display 2102A, computer 102 may prompt the user to start a movement for tracking. The user may perform any desired type of movement, denoted hereafter as "freestyle" movement. In freestyle display 2102B, computer 102 may display a user's vertical leap, airtime, and foot used for a jump during the freestyle movement. Freestyle display 2102B may display performance metrics deemed relevant by the system 100, by the user, or both. For example, performance metrics could be the vertical leap, airtime, foot, as shown in display 2102B, could be the weight distribution shown in display 2102C, or both with the user cycling through. In freestyle display 2102C, computer 102 may display a weight distribution measured by distributed sensor 306. The user may also review weight distributions over time to determine how the user's weight distribution may have affected a user's availability to move or leap. A user may, for example, slide their finger across display to move between displays 2102A-C.

Figure 22:
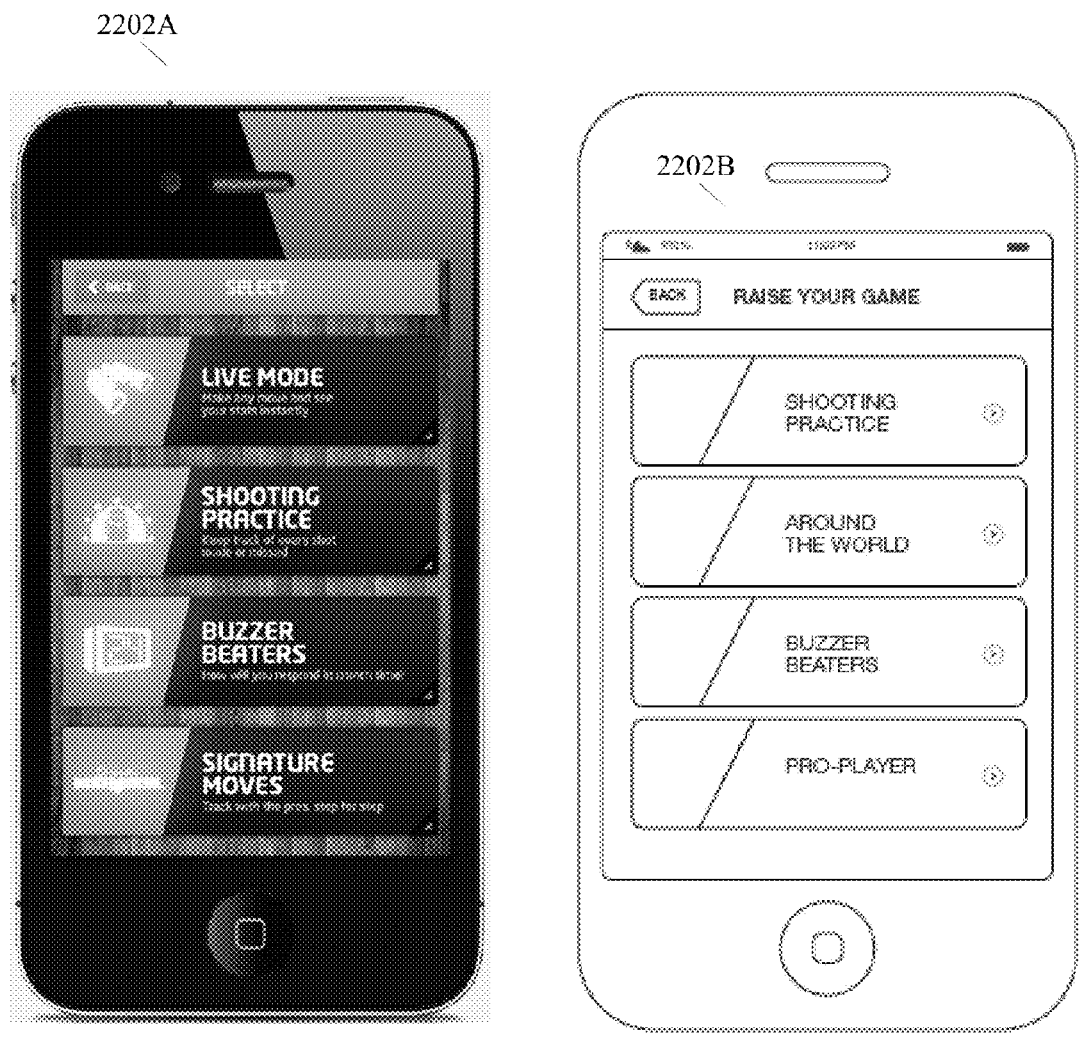
FIG. 22 illustrates example training displays presenting user-selectable training sessions in accordance with example embodiments.

In addition to monitoring a user's performance during a session, computer 102 may assist a user in improving their athletic skills FIG. 22 illustrates example training displays 2202A-B presenting user-selectable training sessions in accordance with example embodiments. The training sessions may guide the user through a set of movements designed to improve a user's athletic ability. Example training sessions may include a shooting practice, an all around the world game, a buzzer beater game, a pro-player game, a basic game, an air time game, a continuous crossover game, a free throw balance game, a signature moves game, a pro battles game, and a horse game. These training sessions are further described in FIGS. 23-26. For example, computer 102 may have a touchscreen permitting a user to scroll between and select the training sessions shown in FIGS. 23-26. FIG. 26, for example, illustrates a couple of exemplary games that may be played against professional athletes or others. Professional athlete shots may be selected at random from a collection of shots attempted in games or practices, pseudorandomly to make sure there is a desired distribution of shots or with some other criteria. In one embodiment a professional athlete may attempt numerous shots during a training session and the results of those shots are later used in a game.

Figure 27:
FIGS. 27-30 illustrate display screens for GUIs for a basketball shooting training session in accordance with example embodiments.
Figure 28:
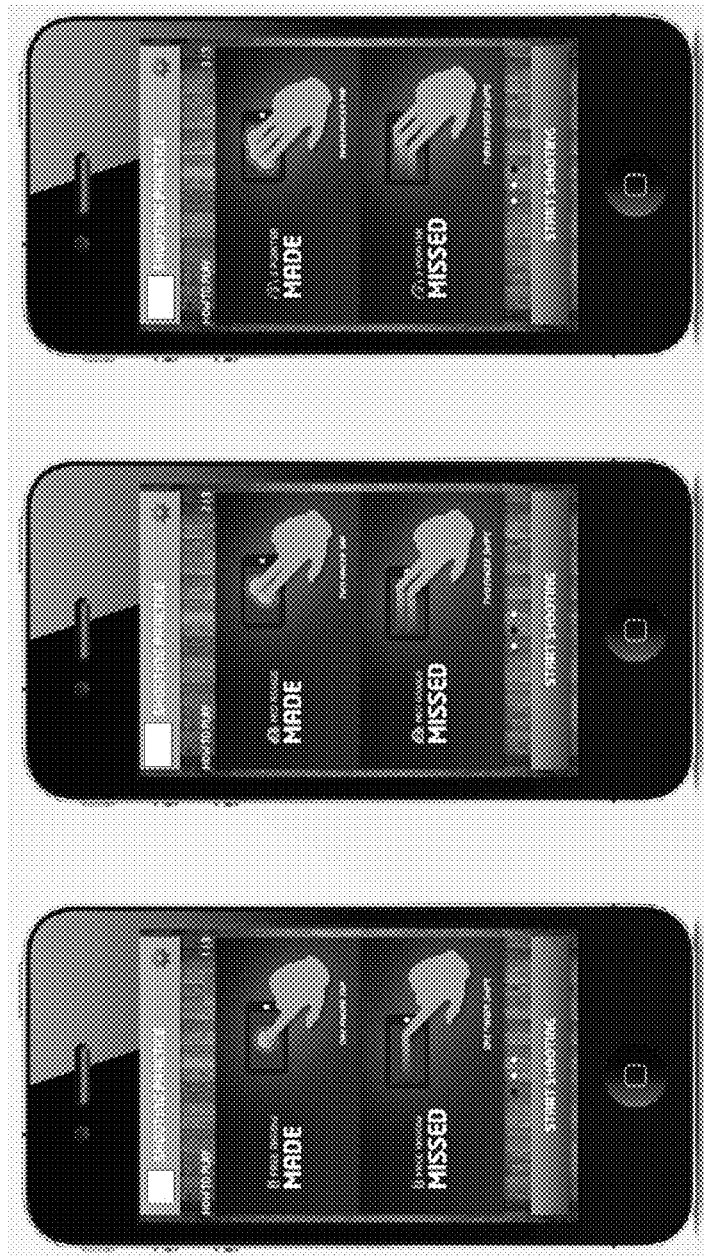

FIGS. 27-30 illustrate display screens for GUIs for a basketball shooting training session in accordance with example embodiments. In FIG. 27, training display 2702 may present the user with information on their last session (e.g., shooting percentage for free throws, three pointers, and jump shots) and prompt the user to begin a new session. The computer 102 may monitor touches on a pressure sensitive display screen to track makes and misses. To do so, the computer 102 may monitor how many fingers were used to distinguish between basketball shots. For example, three fingers may be used to indicate a three point shot in basketball, two fingers may be used to indicate a two point shot, and a single finger may be used to indicate a free throw, as seen in FIG. 28. A tap of one or more fingers on the display screen may indicate a made shot, and a swipe of one or more fingers across a portion of the display screen may indicate a miss. In other examples, a down swipe across a display screen of computer 102 with one or more fingers may indicate a make and an up swipe with one or more fingers may indicate a miss.

Figure 29:
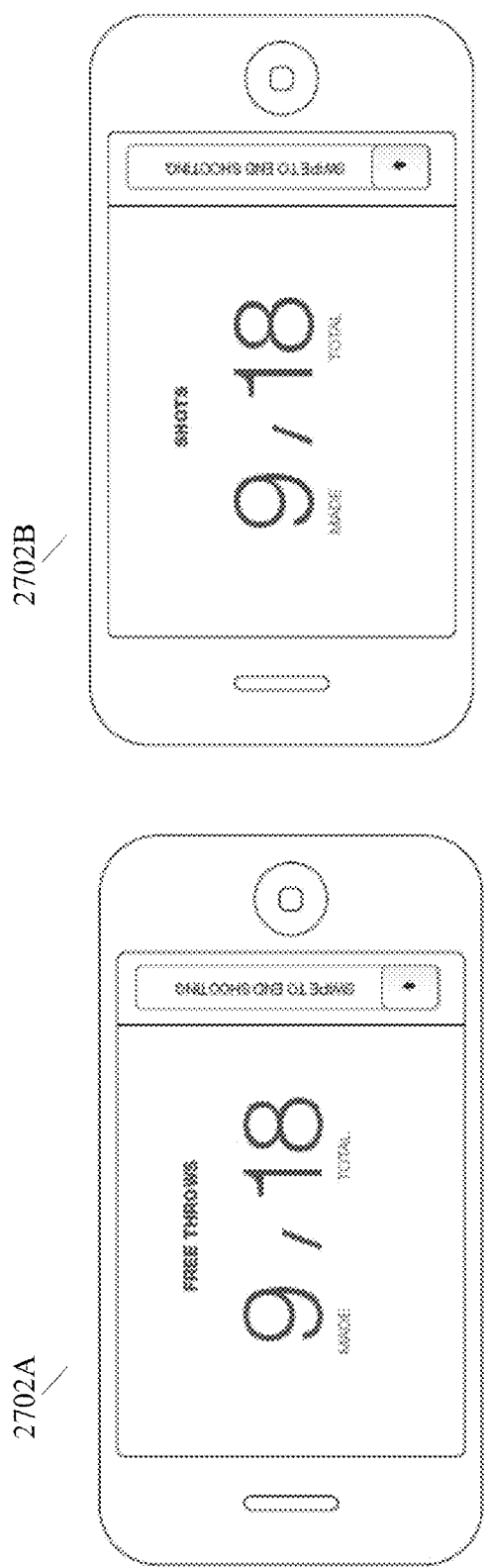

The computer 102 may process the user input to determine a number of fingers used as well as between a tap and a swipe. The computer 102 may determine an amount of area of the display screen covered by the fingers when tapping and/or swiping the display screen to distinguish between one, two, or three fingers. The computer 102 may also determine duration of the touch and if a region of the display screen initially contacted by the user differs from a region of the display screen at the end of the touch to distinguish between a tap and a swipe. At the end of a session, the training display 2702 may display information on makes and misses to the user, as seen in FIG. 29. The training display 2702 may display makes/misses by shot type as well as totals for all shot types. For example, training display 2702A may display makes and misses for free throws, and training display 2702B may display makes and misses for jump shots. Training display 2702B may aggregate 2 and 3 point basketball shots and may display makes and misses together, or separate displays may present makes and misses for each type of shot.

Figure 30:
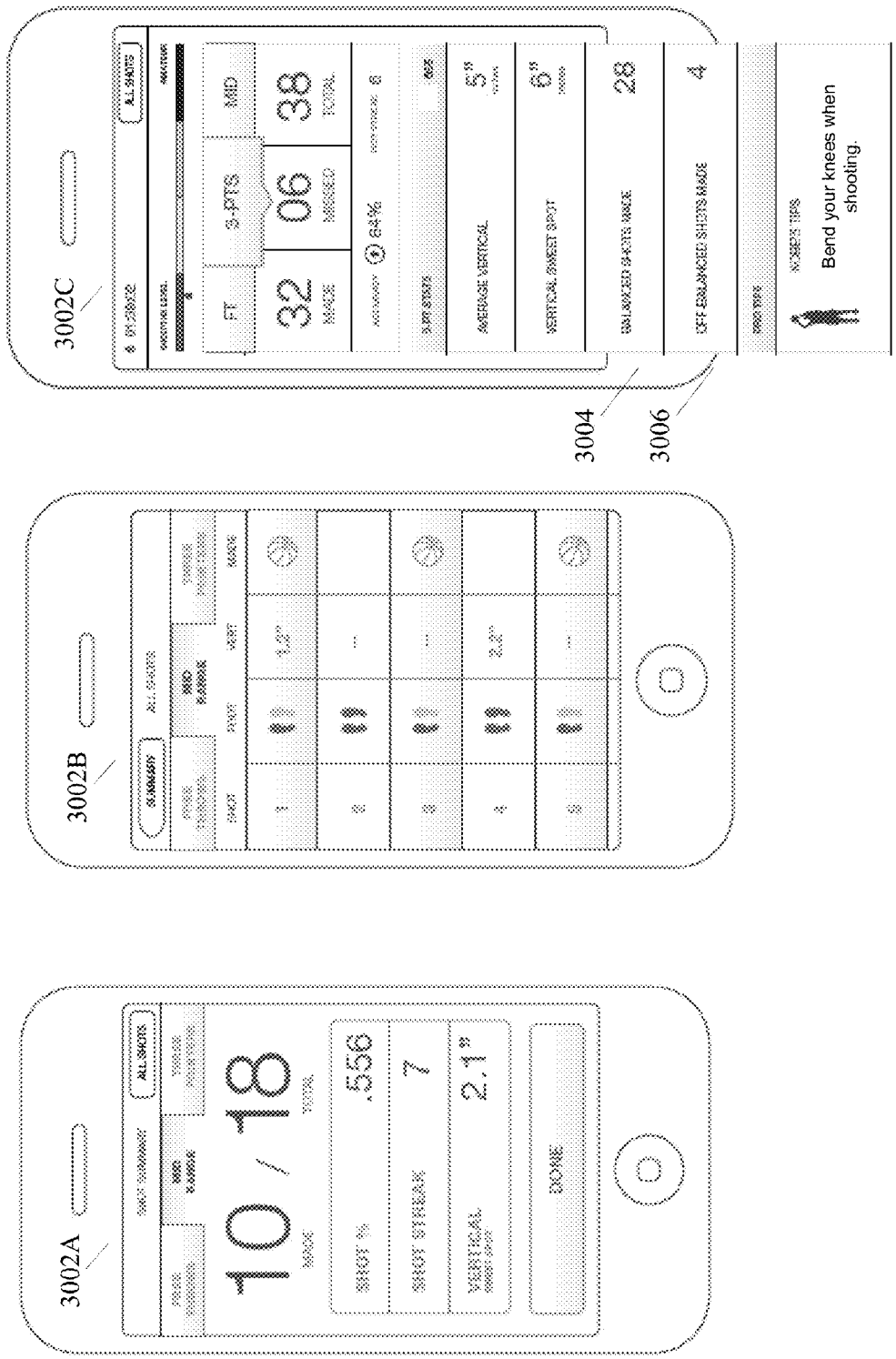

FIG. 30 illustrates example displays for a GUI providing the user with information on a shooting practice session in accordance with example embodiments. Shot summary display 3002A may permit the user to select all shots or a particular shot type to receive information on percentage of shots made (e.g., 55.6%), a streak of how many shots were made consecutively, and the user's vertical leap "sweet spot" for the makes. The sweet spot may indicate a vertical leap where a user's shooting percentage (e.g., percentage of made shots) exceeds a predetermined amount (e.g., 50%). The computer 102 may process data from the pod sensor 304 and/or from distributed sensor 306 to provide the user information about their makes and misses via the GUI. This information may include on average vertical leap for makes and misses to inform the user about how jump height affects their shooting performance. Shot summary display 3002B may inform the user which foot was used when jumping as part of a shot along with a height of a vertical leap, and whether a shot was made or missed. Shot summary display 3002C may provide the user with information about three point shots made and missed.

The shot summary display 3002 may provide the user with statistic information as to how their balance affects their shots by indicating how many balanced shots were made and how many off-balanced shots were made. The computer 102 may determine balance based on weight distribution measured by distributed sensor 306 while a user took a shot. If weight is relatively evenly distributed between a user's two feet (i.e., within a certain threshold), the computer 102 may identify a shot as being balanced. When weight is not relatively evenly distributed between a user's two feet (i.e., outside of a certain threshold), the computer 102 may identify a shot as being unbalanced. The shot summary display 3002C may also provide a user with feedback about their balance and tips to correct any issues with unbalanced weight distribution. For example, field 3004 may indicate how many shots were made when a user's weight was balanced and field 3006 may indicate how many shots were made when a user's weight was off-balance.

In an example, computer 102 may receive and process data generated by a force sensor to determine a weight distribution during a performance of an exercise task (e.g., shooting a jump shot in basketball). Computer 102 may process user input indicating successful completion of an exercise task (e.g., a make). Computer 102 may associate a detected weight distribution at a time preceding the user input indicating successful completion of the exercise task. For example, computer 102 may process sensor data to identify movement consistent with a basketball shot, and determine a weight distribution starting with detecting lift-off when a user jumps during a jump shot, a period of time prior to lift-off, landing, and a period of time after landing. Computer 102 may monitor weight distribution for these periods of time. At a subsequent time (e.g., second or subsequent jump shot), computer 102 may process additional user input indicating unsuccessful completion of the exercise task (e.g., a miss). Computer 102 may associate a detected weight distribution at a time preceding the user input with the unsuccessful completion of the exercise task. After or during the exercise session, computer 102 may present to the user information about their weight distribution and about how the distribution has affected the user's ability to complete the exercise task.

Figure 31:
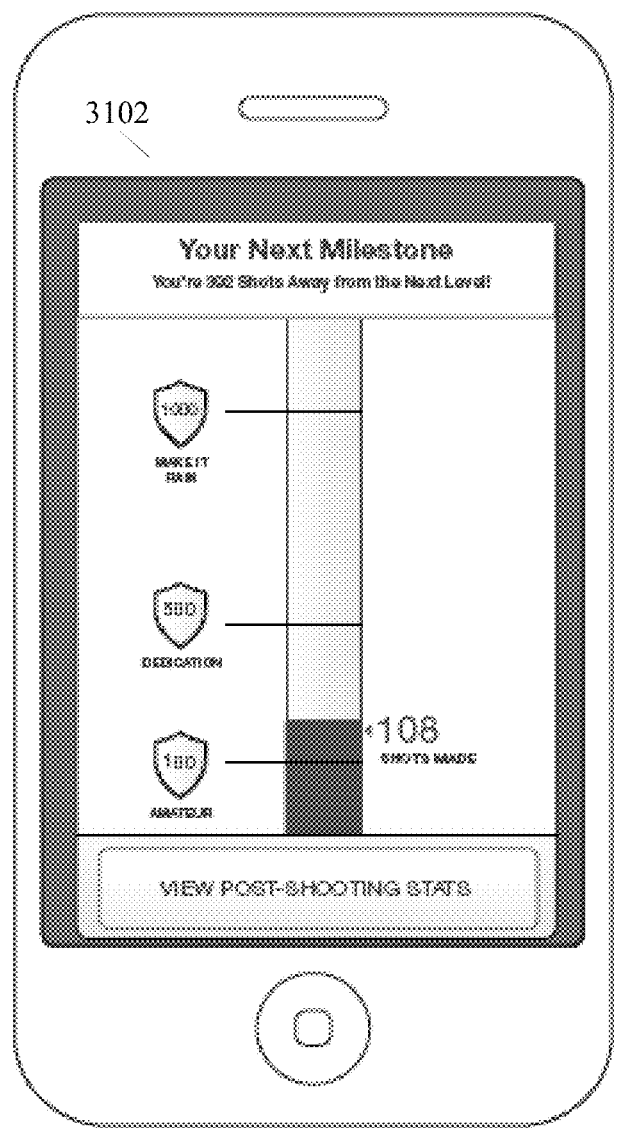
FIG. 31 illustrates an example display of a GUI informing the user of shooting milestones in accordance with example embodiments.

The GUI may also provide the user with incentives to working on their basketball shot. FIG. 31 illustrates an example display of a GUI informing the user of shooting milestones in accordance with example embodiments. Milestone display 3102 may inform the user of one or more shot thresholds and how many shots a user has made. For example, milestone display 3102 may indicate that a user has made 108 shots, such that the user has reached amateur status, and needs to make an additional 392 shots to achieve the next status level.

Figure 32:
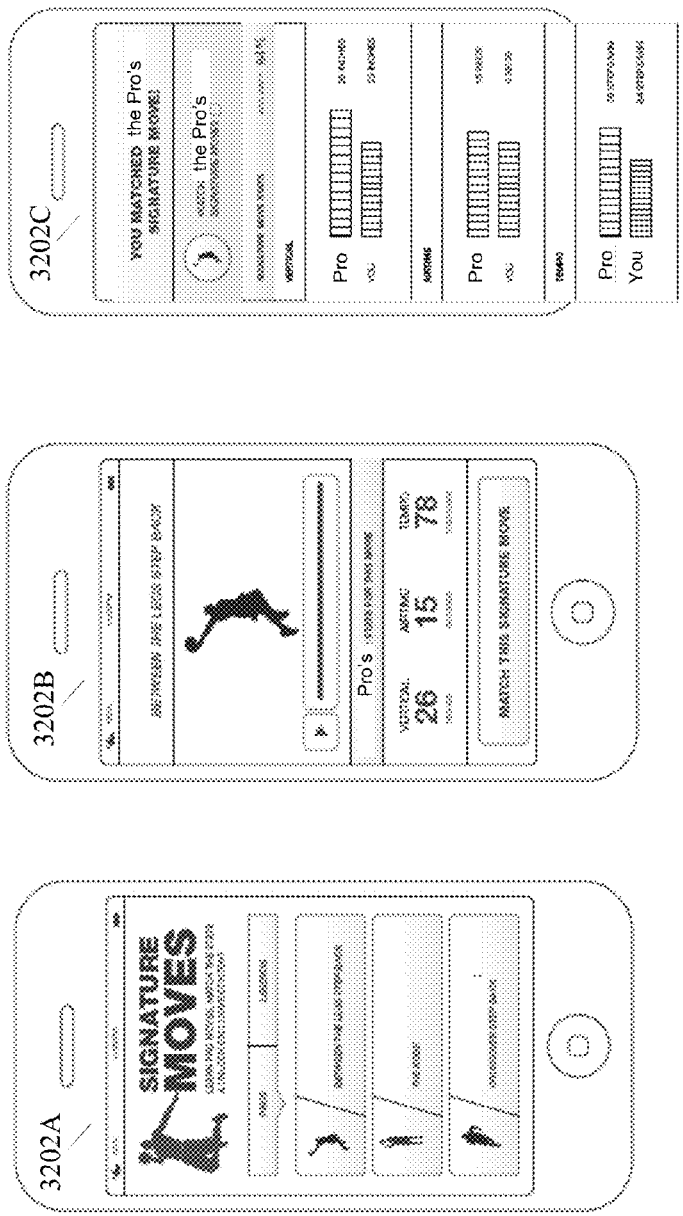
FIG. 32 illustrates example signature moves displays for a GUI prompting a user to perform a drill to imitate a professional athlete's signature move in accordance with example embodiments.

As a part of drills for enhancing a user's skills, computer 102 may prompt the user to perform moves similar to the ones used by professional athletes. FIG. 32 illustrates example signature moves displays for a GUI prompting a user to perform a drill to imitate a professional athlete's signature move in accordance with example embodiments. In addition to professional athlete signature moves, users may create and share signatures moves with other users.

In an example, a user may input a search query into signature moves display 3202A to initiate a search for a desired professional athlete. The computer 102 may forward the search query to the server 134, which may reply with query results. The server 134 may also provide the computer 102 with suggested signature moves for display prior to a user inputting a search query. As seen in signature moves display 3202A, computer 102 may display different signature moves for user selection. Upon selection of a particular move, signature moves display 3202B may present video of the signature move and provide the professional's performance metrics for the move. The computer 102 may, for instance, query the server 134 for signature move data in response to the user's selection to generate signature moves display 3202B. The signature move data may include data from pod sensor 304 and distributed sensor 306 of a professional athlete performing a signature move. The user may attempt to imitate the signature move and the computer 102 may process the user data to indicate the accuracy of the imitation.

After completion of an attempt of the signature move, the computer 102 may inform the user how well they successfully imitated the move. To identify a match, the computer 102 may compare data obtained from pod sensor 304 and/or distributed sensor 306 with the signature move data to determine if the two are similar. The computer 102 may monitor how long a user took to complete the signature move, a vertical leap of the user, airtime of the user, tempo of the user, or other information and compare this data to corresponding data from the professional athlete. The computer 102 may also indicate how accurately the user imitated the signature move of the professional athlete, as shown in signature moves display 3202C. Accuracy may be based on a combination of how similar each of the performance metrics is to the professional's. The computer 102 may weight certain metrics more highly than others, or may weight each metric equally. For example, the signature move data may provide information on three different metrics, and may compare the user's data to each of the three metrics. The computer 102 may determine a ratio of the user's performance metric to the professional's metric and may identify a match if the ratio is above a threshold (e.g., more than 80%). Accuracy also may be determined in other manners.

In an example, computer 102 may receive signature move data corresponding to acceleration and force measurement data measured by a first user (e.g., a professional athlete) performing a sequence of exercise tasks (e.g., cuts in basketball followed by a dunk). Computer 102 may receive and process user data generated by at least one of sensors 304 and 306 by monitoring a second user attempting to perform the same sequence of exercise tasks. Computer 102 may then generate a similarity metric indicating how similar the user data is to the signature move data.

Figure 33:
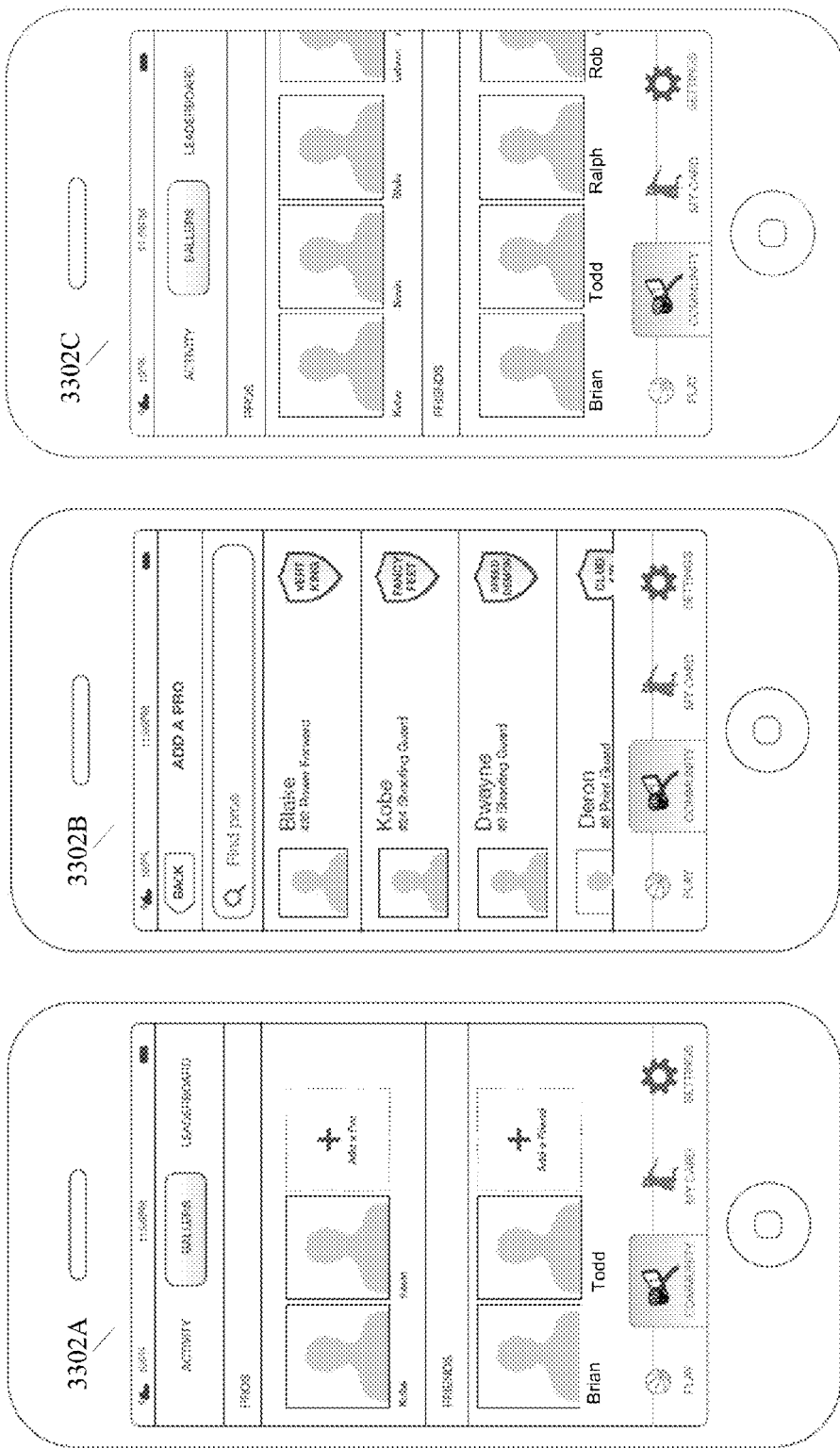
FIG. 33 illustrates example displays of a GUI for searching for other users and/or professional athletes for comparison of performance metrics in accordance with example embodiments.

Computer 102 may also provide the user with data on performance metrics from other users and/or professional athletes for comparison as part of a social network. FIG. 33 illustrates example displays of a GUI for searching for other users and/or professional athletes for comparison of performance metrics in accordance with example embodiments. Computer 102 may communicate with the server 134 to identify professional athletes or friends of the user, as seen in display 3302A. Each individual may be associated with a unique identifier. For example, the user may select to add a friend or a professional, as seen in the GUI display on the left. When a user elects to add a friend/professional, the user may input a search query into the computer 102 for communication to the server 134, which may respond with people and/or professional athletes matching the search query, as seen in display 3302B. The user may establish a user profile to identify their friends and/or favorite professional athletes so that the computer 102 may automatically load these individuals, as seen in display 3302C.

Figure 34:
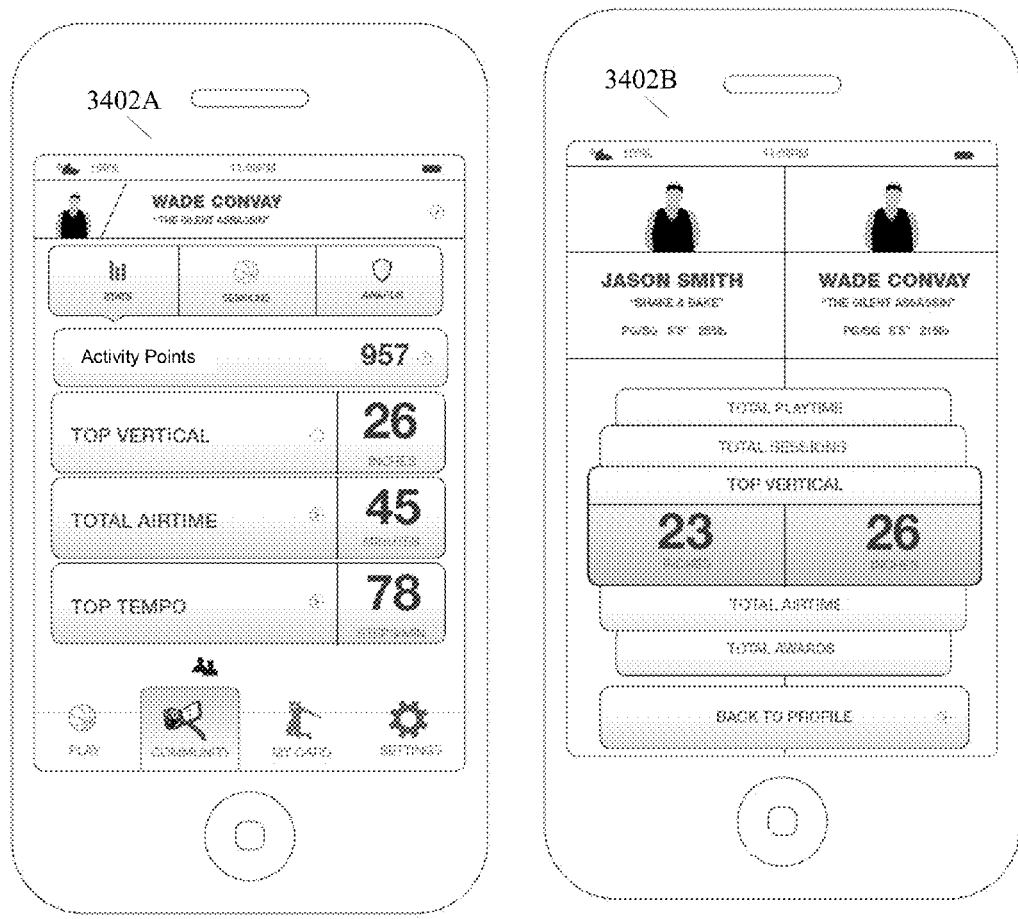
FIGS. 34-35 illustrate example displays for comparing a user's performance metrics to other individuals in accordance with example embodiments.

Computer 102 may present data for sharing with friends and/or posted to a social networking website. In FIG. 34, for example, display 3402A provides information for sharing, including points, top vertical, total airtime, and top tempo. Display 3402B, for instance, provides a side by side comparison of performance metrics of a user and an identified friend. In an example, the server 134 may store performance metric data on each user and may communicate the data with computer 102 of the other user upon request. In various embodiments a user can select other users or himself or herself with a GUI display such as the one shown in FIG. 33. In response to selecting other users, information for the user, such as the information shown in FIG. 34 may be displayed. When the user selects himself or herself, information about the user, such as the information shown in FIG. 14 may be displayed. Some users may not have activity corresponding to a particular sport, such as basketball. When an icon that represents such users is selected, more general activity information may be displayed.

Figure 35:
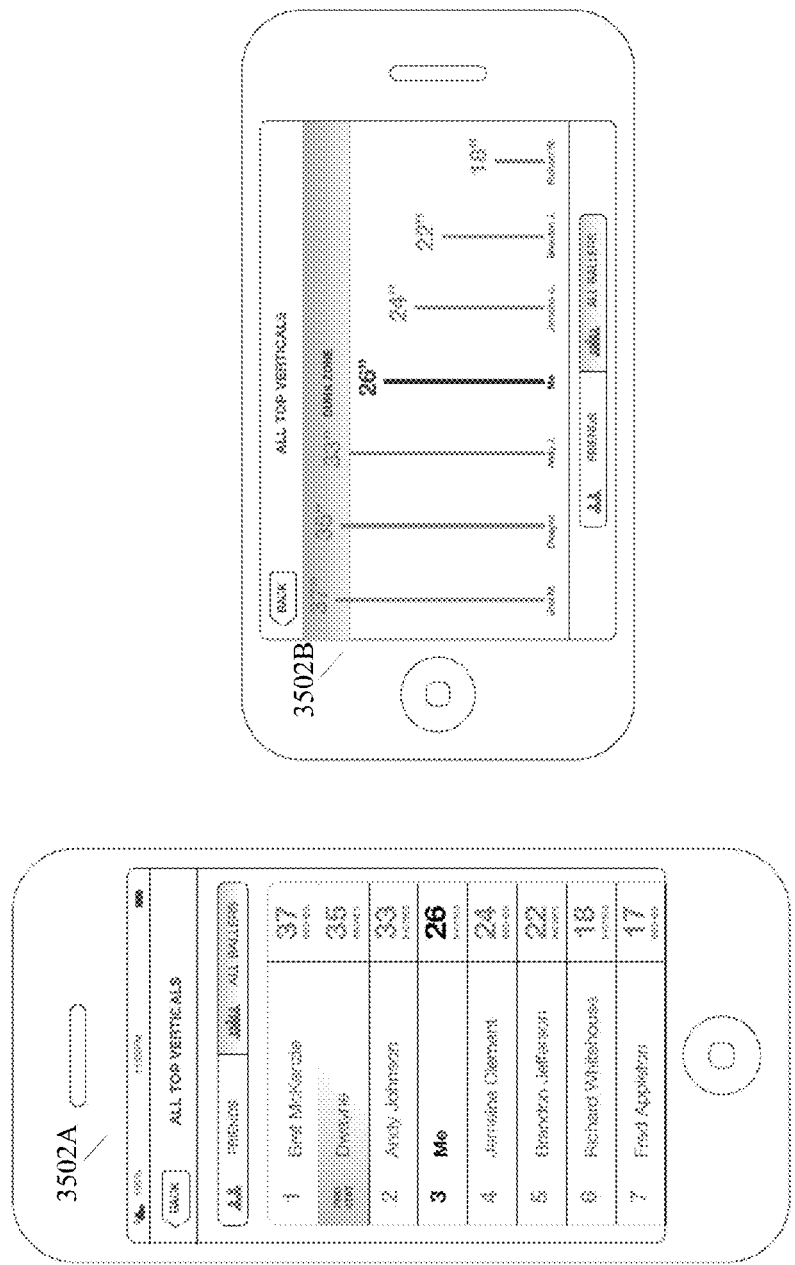

FIG. 35 illustrates example displays for comparing a user's performance metrics to other individuals in accordance with example embodiments. For example, display 3502A may provide a leader board for comparison of a user's performance metric to friends, selected professional athletes, or all other users including professional athletes. Example leader boards may be for a top vertical, a top tempo, a total airtime, total games played, total awards won, or for other performance metrics. Display 3502B permits a user to view individuals whose performance metrics indicate they are in and are not in a performance zone (e.g., dunk zone). Computer 102 may also permit the user to compare their performance metrics to a particular group (e.g., friends) or to all users.

The foregoing discussion was provided primarily in relation to basketball, but the above examples may be applied to other team sports as well as individual sports.

Figure 36:
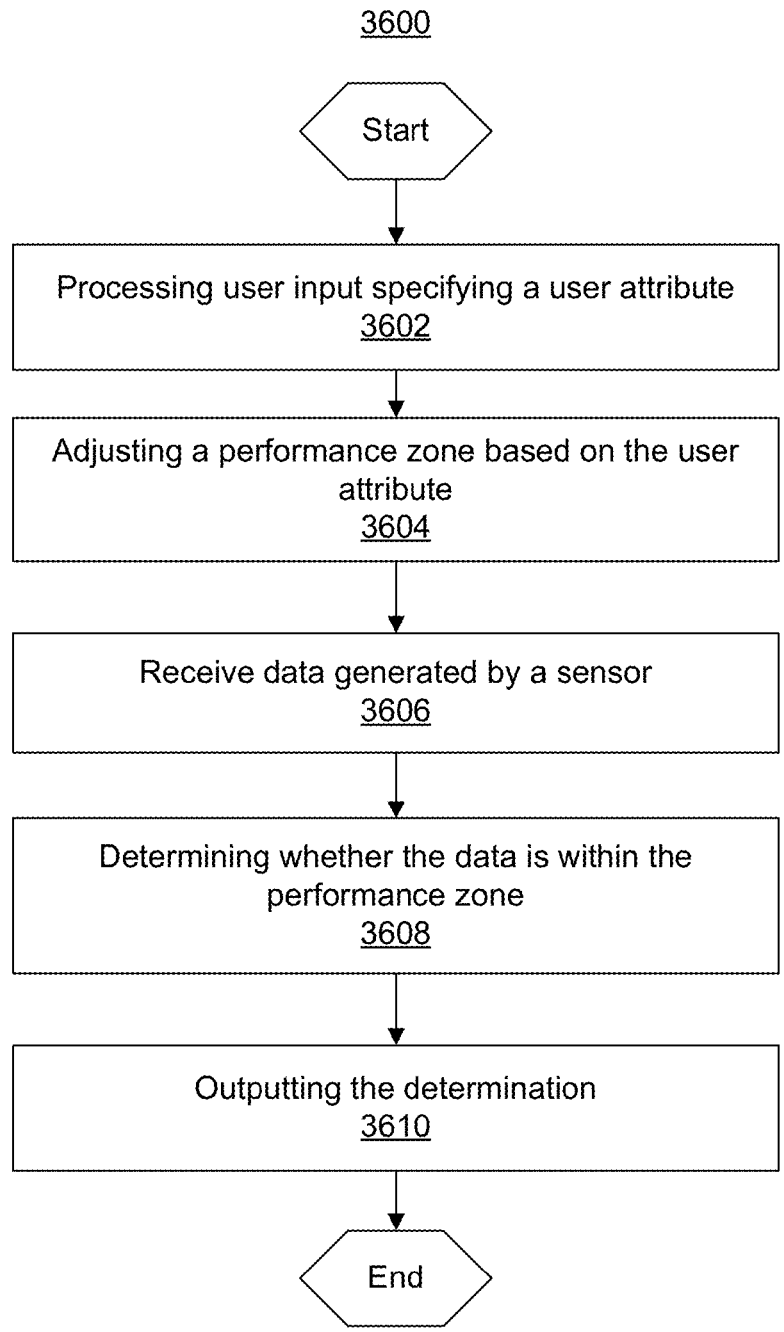
FIG. 36 illustrates a flow diagram of an example method for determining whether physical data obtained monitoring a user performing a physical activity is within a performance zone in accordance with example embodiments.

FIG. 36 illustrates a flow diagram of an example method for determining whether physical data obtained monitoring a user performing a physical activity is within a performance zone in accordance with example embodiments. The method of FIG. 36 may be implemented by a computer, such as, for example, the computer 102, server 134, a distributed computing system, a cloud computer, other apparatus, and combinations thereof. The order of the steps shown in FIG. 36 may also be rearranged, additional steps may be included, some steps may be removed, and some steps may be repeated one or more times. The method may begin at block 3602.

In block 3602, the method may include processing input specifying a user attribute. In an example, computer 102 may prompt the user to input on one or more user attributes. Example user attributes may include height, weight, arm length, torso length, leg length, wing span, etc. In an example, user may specify their body length. Body length may be a measurement of how high a user can reach one of their hands while keeping the opposite foot on the floor.

In block 3604, the method may include adjusting a performance zone based on the user attribute. In an example, computer 102 may adjust a performance zone relating to how high a user must jump to dunk a basketball based on one or more of user height, arm length, torso length, and leg length. For taller users, the performance zone may specify a lower minimum jump height to dunk a basketball as compared with a minimum jump height required for a smaller user to dunk or reach a basketball rim.

In block 3606, the method may include receiving data generated by a sensor. In an example, computer 102 may receive data from at least one of sensor 304 and 306 during an exercise session in which the user performs one or more jumps. As discussed above, the data may be raw signals or may be data processed by the sensors prior to sending to computer 102.

In block 3608, the method may include determining whether the data is within the performance zone. In an example, computer 102 may process data received from at least one of sensor 206 and 304 to determine if any jump performed by the user met or exceeded the minimum jump height of the performance zone tailored to the user's attributes. For example, computer 102 may determine that a minimum vertical leap of 30 inches would be required for a user to dunk a basketball, based on the user attributes. Computer 102 may process data received from at least one of sensor 304 and 306 to determine whether any jump performed by the user met or exceeded 30 inches. To determine a height of the vertical leap, computer 102 may process data generated by at least one of an accelerometer and a force sensor, and comparing the data to jump data to determine that the data is consistent with a jump (e.g., that a user sitting on a chair didn't merely lift their feet off of the ground for a predetermined amount of time). Computer 102 may, in response to the comparing, process data generated by at least one of an accelerometer and a force sensor to determine a lift off time, a landing time, and a loft time. Computer 102 may calculate vertical leap based on the loft time.

In block 3610, the method may include outputting the determination. In an example, computer 102 may output the determination of whether the user was within the performance zone. The output may be at least one of audible and visual. Computer 102 may provide the output immediately upon detecting the user is within the performance zone, or may output the determination at some later time (e.g., post workout). The method may then end, or may return to any of the preceding steps.

Further aspects relate to correlating image data with data relating to physical activity, such as including, but not limited to, any of the raw and/or processed data disclosed in any of the above embodiments. Data relating to physical activity (either raw or processed) may be obtained, directly or indirectly, and/or derived from one or more sensors, including those disclosed herein. In accordance with certain embodiments, physical activity data may be overlaid on an image (or sequence of images, e.g., video) of a user, such as user 124, that was captured during performance of the physical activity.

Figure 37:
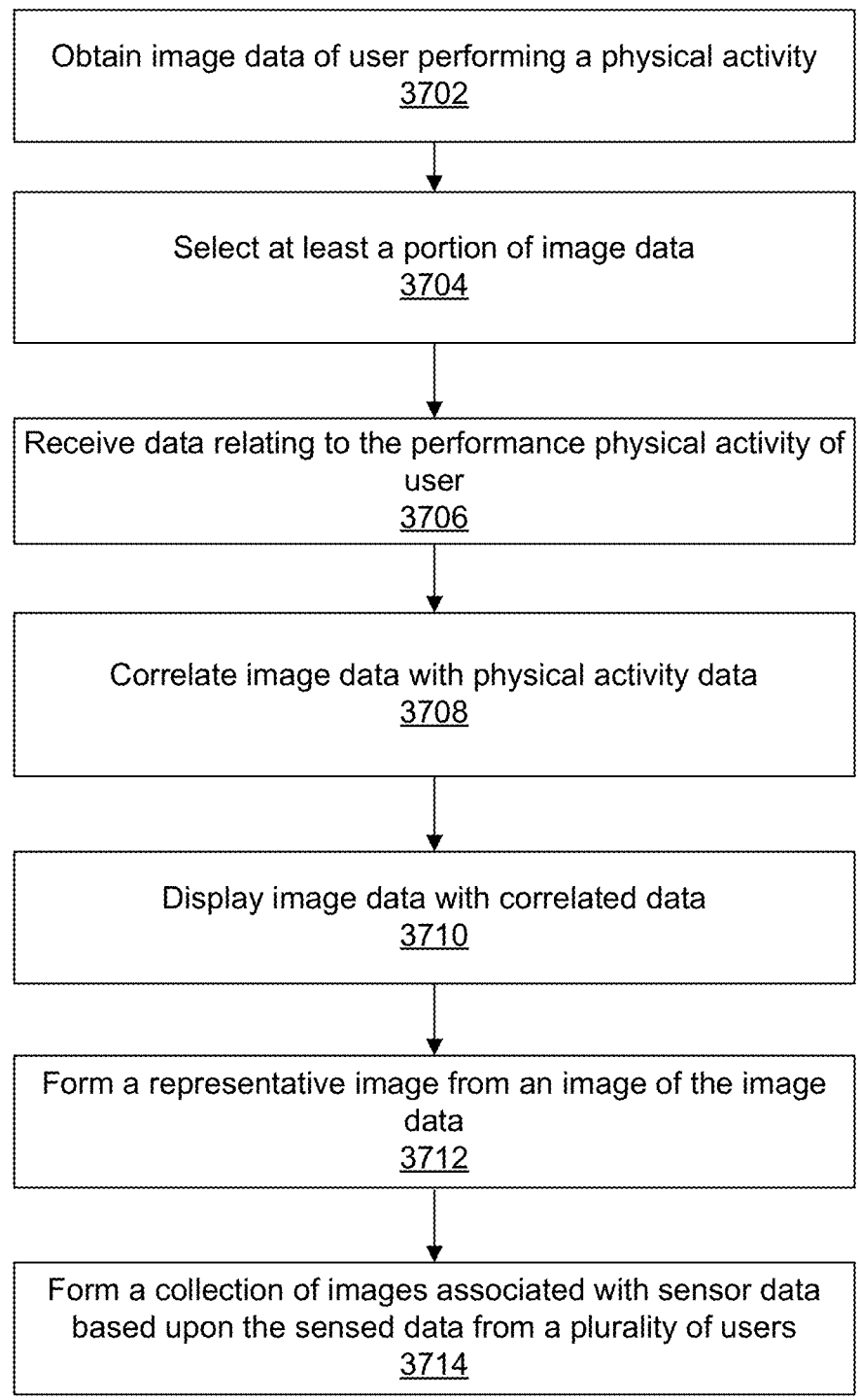
FIG. 37 is a flowchart of an example method of processing image data that may be utilized in accordance with various embodiments.

FIG. 37 is a flowchart of an example method that may be utilized in accordance with various embodiments. At exemplary block 3702, image data may be obtained. Image data may be captured from one or more image-capturing devices, such as a camera located on a mobile terminal device (see, element 138 of FIG. 1A), a video camera, a still-image camera, and/or any apparatus configurable to detect wavelengths of energy, including light, magnetic fields, and/or thermal energy. As used herein, "image data" may encompass raw and/or compressed data, either in a physical tangible form or stored on a computer-readable medium as electronic information. Further, a plurality of images may form part of a video. Thus, references to images and/or pictures encompass videos and the like.

In one embodiment, image data, such as information obtained during the user's performance of physical activity (e.g., participating in a basketball game and/or performing a specific action, such as dunking a ball in a basket), may be captured from one or more devices. For example, a computer-readable medium may comprise computer-executable instructions that, when executed, may perform obtaining a plurality of images (e.g. a video) of the athlete playing a sport. For example, mobile terminal 138 may comprise an application that permits user 124 (or another user) to use an image capturing device (either part of the mobile terminal 138 or provide an input to an external image-capturing device, such as camera 126) to capture the image data.

In one embodiment, upon the user activating a record function (which may be a hard or soft button) on a host device (e.g., the mobile terminal 138), the simultaneous capturing of the video and physical activity sensor data may be initiated. In certain embodiments, multiple cameras may be utilized simultaneously. Multiple cameras may be used, for example, based upon the user's location, (e.g., through detection of the user by way of GPS, triangulation, or motion sensors). Image data may be obtained in response to a user operating a camera on a device, such as a camera of mobile terminal 138. In one embodiment, user 124 may provide mobile terminal 138 to another individual who can capture video of the user 124 playing a sport or performing a fitness activity. However, in further embodiments, one or more cameras may be in a fixed position, angle, focus, and/or combinations thereof. In certain embodiments, image data may be obtained from a broadcast source not directly controllable by user 124 (and/or individuals or entities under user's 124 direction), such as for example a content source provider. For example, a content source provider may broadcast (either live and/or delayed) a sporting event. In one embodiment, the event may comprise a scheduled basketball game. However in another embodiment, sporting event may comprise an unscheduled event, such as a pickup game. In certain embodiments, multiple camera feeds may be utilized to determine which feed(s) or sources of images to use.

In one embodiment, image data may only be captured based on sensor data. In one embodiment, sensor data may be physical activity data. For example, in certain implementations, image data may only be captured upon determining that user is within a "performance zone." In another embodiment, at least one physical attribute value must meet a threshold. Other embodiments may indiscriminately capture image data of user 124, and optional block 3704 or another process may be performed to select a portion of the captured image data. For example, block 3702 may capture over 20 minutes of image data of user 124, however, block 3704 may only select those portions in which the user 124 was in a performance zone. Those skilled in the art will readily appreciate that other selection criteria are within the scope of this disclosure.

The image data obtained in block 3702 (and/or selected at block 3704) may be stored on one or more non-transitory computer-readable mediums, such as on server 134, network 132, mobile terminal 138, and/or computer 102. The type and/or form of the image data may depend on a myriad of factors, including but not limited to: physical activity data (for example, as obtained from a sensor), user selection, calibration parameters, and combinations thereof. Image data may be time stamped. Time stamping of image data may be performed as part of the image data's collection and/or storage. The time stamp information may comprise a "relative" time stamp that does not depend on the actual time of capture, but rather is tied to another event, such as a data point of activity data, start time, and/or any other events. In another embodiment, an "actual" time stamp may be utilized in which the time of capture may or may not be related to another event. Those skilled in the art will appreciate that both types of stamps may be utilized, including the utilization of a single actual time stamp that is also correlated to another event.

At block 3706, physical activity data may be received. As discussed above in relation to image data, activity data may also be time stamped. In one embodiment, sensor data may be received, which may comprise raw and/or processed information relating to the user's 124 activity. Activity data may be obtained from one or more sensors described herein. For example, in one embodiment, the user's footwear may comprise at least one sensor. In certain embodiments, at least a portion of the athletic data may remain on the sensory device or another device operatively connected to the user (e.g., wrist-worn device and/or shoe-mounted sensors) until the capturing time period is over. The data may then be joined as a single file using time stamps. Certain implementations may store a single file, but transmit a first portion of the data (such as the image data) separate from a second portion (such as the activity data). In another embodiment, a first portion of data (such as the image data) may be stored separate from a second portion (such as the activity data), yet may be transmitted to a first tangible computer-readable medium as a single file.

Multiple sensors (from one or more devices) may be utilized. In one embodiment, raw accelerometer and/or gyroscope data may be obtained and processed. In another embodiment, force sensor data may be received. In yet another embodiment, physical activity parameters may be calculated based upon one or more raw parameters from a plurality of sensors. As one example, FIG. 9 shows a plurality of data parameters that may be obtained in accordance with certain implementations. In certain embodiments, user 124, the sensor data and/or sensors utilized to obtain the data (and/or the calculations for providing any processed data) may be selectable. For example, user 124 (or another input received from another source, either manually or automatically) may select a sensor 140 associated with shoes and/or other apparel. In this regard, inputs may not limited to user 124, for example, a coach, trainer, parent, friend, broadcast personnel, and/or any other individual may select one or more sources for activity data. Further embodiments may calibrate one or more sensors before utilization of corresponding data. In yet other embodiments, if calibration parameters are not obtained, data from one more sensors may be excluded from use. FIG. 10 shows an exemplary embodiment of calibration; however this disclosure is not limited to this embodiment. As discussed above in relation to image data, at least a portion of the physical activity data may be selected for processing and/or utilization.

At block 3708, image data and physical activity data may be correlated. The correlation may be based on the time stamps of the data, such that physical activity data is matched to the image data corresponding to the timing of capture. In yet other embodiments, data may be filtered, processed or otherwise adjusted to be matched with each other. For example, each image of a first video, of user 124 performing athletic activity, may represent ⅟20th of a second of the first video, however, data from a first sensor may provide activity data values every ⅕th of a second, therefore, in one embodiment; four consecutive "frames" of image data during the ⅟20th of a second may be associated with the sensor data captured during that ⅕ second increment. In yet other embodiments, a plurality of physical activity values may be weighted, averaged, or otherwise adjusted to be associated with a single "frame" or collective image. Correlation of the data may be implemented on one or more computer-readable mediums.

Correlation of at least a portion of the data may be implemented on a real-time basis, and/or later in time. Correlation may not occur until a selection of a portion of data is selected. In certain embodiments, the data may not be correlated until a specific user is selected. For example, image and/or physical activity data may be correlated upon the determination of a winner of a game, or upon the occurrence of an event (e.g., a user dunking a basketball). Further the type and amount of data to be correlated may also be selectable. For example, upon determining a user dunked a basketball, correlation may be performed on image and/or activity data that occurred 10 seconds prior to the dunk and continues to 3 seconds after the dunk. In one embodiment, upon determining that a player won a game or event, a larger portion of their data would be correlated. For example, data covering an entire time frame of a game or event may be utilized. Further, the data correlated may depend on the event, data collected, or other variables. For example, for a basketball dunk, activity data collected or derived from one or more force sensors within user's shoes may be utilized, yet in a soccer match, arm swing data may be utilized, alone or in combination with other data, to determine steps per second, speed, distance, or other parameters. Correlation data may include, but is not limited to: identification of the sensing unit, specific sensor, user, time stamp(s), calibration parameters, confidence values, and combinations thereof.

In further embodiments, system 100 may receive and/or process data generated by a sensor, such as a force sensor, to determine a weight distribution during a performance of an exercise task (e.g., shooting a jump shot in basketball). System 100 may associate a detected weight distribution, at a time preceding the user input, to determine an initiation point and/or cessation point for correlation of specific data. At a subsequent time, system 100 may also process additional user input indicating unsuccessful completion of the exercise task.

System 100 may process sensor data, such as for example, data received from the pod sensor 304 and/or the FSR sensor 206 over a session to determine which data may be classified and/or correlated. For example, a user's hustle during a session may be categorized into two or more categories. With reference to hustle display 1902B, system 100 may divide hustle into four categories: walking, jogging, running, and sprinting. With reference to hustle display 1902C, system 100 may divide hustle into three categories: low, medium and high. More or fewer categories of hustle may be defined. System 100 may process the data to identify a category based on a rate of steps taken by a user per interval of time (e.g., steps per minute). The correlated physical activity data may comprise information indicative of when and/or how often a user was in each category during a session. In certain embodiments, only physical activity indicative of being within one or more specific categories may be correlated with the corresponding image data.

In certain embodiments, data may be transmitted and displayed on one or more devices. In certain embodiments, the display device may be physically distinct from the device which is capturing the image(s) (see, e.g., block 3710). For example, in one embodiment, an individual may utilize a portable device, such as a mobile terminal, to capture a video of user 124 performing physical activity, such as participating in a basketball game. Information regarding the captured images may be transmitted (either before or after being correlated with data relating to the physical activity of user 124) via wired and/or wireless mediums.

FIG. 13, which was discussed above, shows an illustrative example GUI providing performance metrics during an event, game, or session in accordance with example embodiments. One or more of these metrics may relay information about a length of a current or previous session in field 1304, various performance metrics (e.g., top vertical, total airtime, tempo, etc.) for the user in field 1308, as well as who the user played with during the session in field 1310. One or more of these metrics may be overlaid with the corresponding imaging data in accordance with certain embodiments. The image data may be joined to form a video, which may be stored as a single file such that the data overlay is part of the video and is displayed with the corresponding video portion to which that data was captured. In further embodiments, a second file may store the data separate from video data.

In one embodiment, image data (and/or the physical activity) data may be transmitted in real-time. One or more images (with the corresponding activity data) may be displayed on one or more display devices, such as a display at the location of the basketball game, or any other display medium, including but not limited to being multi-casted to multiple display devices. The images (and correlated data) may be viewed via televisions, computing devices, web interfaces, and a combination thereof. In certain embodiments, user 124 and/or other individuals may selectively determine which activity data is displayed on one or more display devices. For example, a first viewer may selectively view the user's current speed and/or average speed, and a second viewer may selectively view the one or more different activity values, such as for example, highest vertical jump, number of sprints, average speed, and a combination thereof. In this regard, the data may be formed from, and/or be updated from a long duration, such as total play time during a game, portion of game (quarter, half, etc.). Thus, there is no requirement that the image data only be correlated to data obtained during capturing of the image data, but instead may further include (or be derived from) previously-obtained data. Further embodiments may present the image and/or physical activity data for sharing with friends and/or posting to a social networking website. The transmission of any data may be based on, at least in part, at least one criterion, such as for example, user-defined criteria that at least a portion of the data meets a threshold. For example, users may only want to upload their best performance(s).

Thus, certain embodiments may utilize historical data. As one example, leap data (such as that shown in leap display 1802B) may display a user's jumps chronologically over a session and may indicate a time when each jump occurred as well as vertical height for each jump during the session. The leap display 1802B may also display the user's current data and/or that user's personal best vertical leap during the event.

Further, as discussed above in relation to the correlation of data, the displaying of any data (and/or the selection of what physical activity data is displayed with the image data) may vary depending on one or more variables; including, for example, the type of game, event, user's 124 selection or input, a viewer's input, an indication that user's 124 performance has met a threshold; e.g., reached a performance zone, and/or a combination thereof. Further embodiments may determine, based on one or more computer-executable instructions on non-transitory computer readable mediums, which activity value(s) may be displayed to viewer(s) for a specific time period and the duration of displaying certain values.

In certain implementations, image data may not be correlated with at least a portion of activity data until a later time. Transmission and/or correlation of image data with activity data may be conducted on a routine basis, such as every 1 second, 10 seconds, 30 seconds, 1 minute, or any increment of time. In this regard, a system and/or user may determine to evaluate one or more metrics at a later time. These metrics may be based on, for example, a type of athletic activity performed in a session (e.g., basketball game, football game, running session, etc.). Certain embodiments may permit the evaluation and/or analysis of different metrics than initially viewed and/or desired upon capturing the image(s). For example, user 124 and/or a coach may be initially interested in evaluating a user's quantity of vertical jumps that meet a first threshold (e.g., about 4 inches), yet at a later time, the coach or user 124 may want to evaluate the image(s) with an overlay of a quantity of steps per unit time (e.g., number of steps per minute). In certain embodiments, computer 102 may prompt the user to indicate which metrics to monitor for each type of session (e.g., baseball, soccer, basketball, etc.) and store the identified metrics in a user profile. In yet another embodiment, the type of session may be derived from collected data, inclusive, but not limited to, activity data or the image data.

Computer 102 may also prompt the user for desired metrics at the beginning of each session for what data to collect—inclusive of data that may not be overlaid over the image. Further embodiments may adjust the image data collected and/or utilized. For example, variations may include the resolution, frame rate, storage format protocol, and combinations thereof. At the beginning of a session, sensors, such as sensors within a shoe (see device sensor 140) and/or other sensors, may be calibrated. Yet in other embodiments, sensors may be calibrated during, or after, a session or event. In certain embodiments, previously collected data may be utilized in determinations of whether to calibrate and/or parameters of calibration.

Block 3710 and/or other aspects of certain embodiments may relate to generating and/or displaying a summary segment with the image data. For example, the image data may be utilized to form a 25 second video. In certain embodiments, the video file may be formed to include a segment (e.g., 5 seconds), such as located at the end of the 25-seconds of image data, that provides a summary of certain statistics. In those embodiments, in which the video is a single file, this segment may also form part of the same single file. In certain embodiments, this summary screen (or another summary) may be presented to the user while the video file is being created (e.g., during the time in which the image data is being properly aligned with the sensor data). Further information may be displayed with the image data. For example, in one embodiment, an overlay may display the origination of the data; such as by a wrist-worn or shoe-mounted sensor, and/or specific manufactures or models of sensors.

Further aspects relate to creating and/or displaying a "representative image" that is formed from an image within the collection of images (see, e.g., block 3712). The representative image may be utilized as a "thumbnail" image or a cover image. In further embodiments, the representative image may be used to represent a specific video among a plurality of videos, in which each may have their own representative image. In one embodiment, the representative image may be selected based upon it being correlated in time with a data value that represents the highest value of at least one athletic parameter. For example, the highest value of a jump (e.g., vertical height) may be utilized to select an image. Yet in other embodiments, the highest value relating to velocity, acceleration, and/or other parameters may be utilized in selecting an image. Those skilled in the art will appreciate that the "best" data value may not be the highest, thus this disclosure is not limited to image data associated with the "highest" value, but rather is inclusive of any data.

In further embodiments, a user (or any individual) may select which parameter(s) are desired. In yet other embodiments, computer-executable instructions on a tangible computer-readable medium may select a parameter based upon the data collected. In yet further embodiments, a plurality of images may be selected based upon the correlated physical activity data, and allow the user to select one. Any physical activity data and/or image data may be associated with location data, such as GPS or a specific court.

Further embodiments relate to creating a collection of image data from a plurality of users, based upon sensed data (see, e.g., block 3714). In one embodiment, a "highlight reel" may be formed which comprises image data of a plurality of users. In one example, a highlight reel may be created from data obtained from a sporting event. For example, a plurality of players on one or more teams may be recorded, such as during a televised sporting event. Based upon sensed athletic data, images (e.g., video) obtained during performance of that data may be aggregated to create a highlight reel for the sporting event or a portion thereof (e.g., the first quarter and/or the final two minutes). For example, sensors may obtain athletic data from the players during the sporting event, and based upon at least one criterion (i.e., jumps higher than 24 inches and/or paces greater than 3 steps per second), correlated image data may be utilized in forming the highlight reel.

Certain embodiments relate to generating a feed or a plurality of image collections based upon at least one criterion. For example, viewers of sporting events often do not have the time to watch every game or competition, such as during playoffs of sporting events. Thus, in one embodiment, a feed may be selectively limited to physical activity of friends, teams or athletes followed, basketball games in which certain team(s) played and a specific player(s) that achieves a specific parameter value(s). Thus, in some embodiments of the invention, image data may comprise image data captured during a first time period and image data captured during a second time period that is different than the first time period. These feeds may also be categorized based upon activity type and/or sensors utilized to capture the activity. In certain embodiments, the highlight reels and/or feeds may be based, at least in part, on whether the player(s) are within a performance zone.

In one embodiment, the image data captured during the first time period is at a first geographic location and image data captured during the second time period is at a second geographic location. In certain implementations, images from two or more locations that are obtained during two different time periods, may be combined into a single image. In one embodiment, a user's physical performance may be captured with a mobile phone or other device and merged with image data corresponding to a historical athletic performance or known venue. For example, a video of a user shooting a basketball shot may be merged with a video of a famous athlete shooting a last minute three-point shot. In some embodiments, a user may capture an image of a scene prior to recording a video of a user performing an athletic move at the same location. A mobile phone, or other device, may then remove the scene data from the video to isolate the user. The isolated video of the user may then be merged with, or overlay, an image or video of another location or event. Similarly, selected portions of captured image data may be replaced. For example, a video of a user slam dunking a tennis ball may be edited to replace the tennis ball with a basketball. Various other features and devices may be used in accordance with the aspects described herein. Additional or alternative features may also be incorporated into the device and/or applications associated therewith.

CONCLUSION

While the invention has been described with respect to specific examples including presently preferred modes of carrying out the invention, those skilled in the art will appreciate that there are numerous variations and permutations of the above described systems and methods. For example, various aspects of the invention may be used in different combinations and various different sub-combinations of aspects of the invention may be used, together, in a single system or method without departing from the invention. In one example, software and applications described herein may be embodied as computer readable instructions stored in computer readable media. Also, various elements, components, and/or steps described above may be changed, changed in order, omitted, and/or additional elements, components, and/or steps may be added without departing from this invention. Thus, the invention should be construed broadly.

I claim:

1. A mobile computing device comprising:
    a touch sensitive display;
    a processor;
    a computer-readable memory containing computer-executable instructions that when executed cause the processor to:
        receive, from a sensor system, activity data relating to a performance of an athletic activity by a user;
        process the received activity data to generate weight distribution data for the user;
        receive input data from the touch sensitive display indicating a number of fingers used to input athletic performance data to the touch sensitive display;
        process the input data to distinguish between at least one of an outcome of the athletic activity and a type of the athletic activity performed by the user;
        determine a plurality of performance metrics based at least in part on the activity data and the input data;
        present athletic training session data to the user, wherein the athletic training session data includes one or more performance metrics in the plurality of performance metrics, wherein the athletic training session data comprises basketball training data and the input data represents point values of shots attempted; and
        associate, at a time preceding a first user input, a first weight distribution of the user with a first outcome of the athletic activity performed by the user.

2. The mobile computing device of claim 1, wherein one finger represents a one point shot.

3. The mobile computing device of claim 2, wherein two fingers represents a two point shot.

4. The mobile computing device of claim 1, wherein a tap represents one of a made shot or a missed shot.

5. The mobile computing device of claim 1, a performance metric in the plurality of performance metrics comprises an average vertical leap for a plurality of successful outcomes of the athletic activity performed by the user.

6. The mobile computing device of claim 1, wherein the computer-executable instructions, when executed, further cause the processor to:
    generate an activity recommendation for the user to perform a successful outcome of the athletic activity based at least in part on the weight distribution data.

7. The mobile computing device of claim 6, wherein the computer-executable instructions, when executed, further cause the processor to:
    (i) determine a duration of a touch on the touch sensitive display;
    (ii) determine if a first region of the touch sensitive display initially contacted by the user differs from a second region of the touch sensitive display at an end of the touch; and
    (ii) distinguish between a tap and a swipe based on the determinations made in (i) and (ii).

8. The mobile computing device of claim 1, wherein a swipe in a first direction represents one of a made shot or a missed shot.

9. The mobile computing device of claim 8, wherein a swipe in a second direction different from the first direction represents the other of a made shot or a missed shot.

10. The mobile computing device of claim 1, wherein the computer-executable instructions, when executed, further cause the processor to calculate a number of shots made and a number of shots missed.

11. The mobile computing device of claim 1, wherein the computer-executable instructions, when executed, further cause the processor to calculate a number of shots made and a number of shots missed based on shot type.

12. The mobile computing device of claim 1, wherein processing the input data further comprises:
   determining an amount of area of the touch sensitive display covered by fingers to distinguish inputs of one finger, two fingers and three fingers.

13. The mobile computing device of claim 1, wherein the mobile computing device comprises a mobile phone.

14. A computer implemented method of providing training information to a user, the method comprising:
   receiving, from a sensor system, activity data relating to a performance of an athletic activity by a user;
   processing, at a processor of a mobile computing device, the received activity data to generate weight distribution data for the user;
   displaying athletic training session information on a touch sensitive display of a mobile computing device;
   receiving input data at the touch sensitive display from a variable number of fingers used to input athletic performance data to the touch sensitive display;
   processing the input data to distinguish between at least one of an outcome of the athletic activity and a type of the athletic activity performed by the user;
   determining, at the processor of the mobile computing device, a plurality of performance metrics based, at least in part, upon the received input data and the activity data,
   wherein the athletic training session information comprises basketball training data and the input data represents point values of shots attempted; and
   associating, at a time preceding a first user input, a first weight distribution of the user with a first outcome of the athletic activity performed by the user.

15. The computer implemented method of claim 14, wherein input data corresponding to one finger indicates a one point shot.

16. The computer implemented method of claim 15, wherein input data corresponding to two fingers indicates a two point shot.

17. The computer implemented method of claim 16, wherein input data corresponding to a tap indicates one of a made shot or a missed shot, and wherein input data corresponding to a swipe indicates the other of a made shot or a missed shot.

* * * * *